(12) United States Patent
Comee et al.

(10) Patent No.: US 12,161,292 B2
(45) Date of Patent: Dec. 10, 2024

(54) DEVICES, SYSTEMS, AND METHODS FOR ENDOSCOPE FLUIDICS

(71) Applicant: Boston Scientific Scimed, Inc., Maple Grove, MN (US)

(72) Inventors: Shaun D. Comee, Fiskdale, MA (US); Nathan T. Cummings, Worcester, MA (US); Paula R. Limberg, Northborough, MA (US); Brian Luis, Worcester, MA (US); Kyle Patrick Moore, Hopkinton, MA (US); Laura E. Richards, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 135 days.

(21) Appl. No.: 17/208,818

(22) Filed: Mar. 22, 2021

(65) Prior Publication Data

US 2021/0298570 A1 Sep. 30, 2021

Related U.S. Application Data

(60) Provisional application No. 62/994,024, filed on Mar. 24, 2020, provisional application No. 62/994,015, (Continued)

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61B 1/12* (2013.01); (Continued)

(58) Field of Classification Search
CPC ............ A61B 1/00068; A61B 1/00082; A61B 1/00091; A61B 1/00094; A61B 1/00119; (Continued)

(56) References Cited

U.S. PATENT DOCUMENTS 4,061,250 A * 12/1977 Tada .................... B05B 11/1014
251/321
4,694,821 A * 9/1987 Kondo ............... A61B 1/00068
600/158
(Continued)

FOREIGN PATENT DOCUMENTS

EP 2431062 A1 3/2012
JP 2000217777 A 8/2000
(Continued)

OTHER PUBLICATIONS

International Search Report and Written Opinion for the International Patent Application No. PCT/US2021/023479, mailed Jul. 9, 2021, 12 pages.
(Continued)

*Primary Examiner* — Ryan N Henderson
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve
(Continued)

control motions. In one or more embodiments, the valve sets and/or valve interface mechanisms may be disposable.

13 Claims, 61 Drawing Sheets

Related U.S. Application Data filed on Mar. 24, 2020, provisional application No. 62/994,018, filed on Mar. 24, 2020, provisional application No. 62/994,008, filed on Mar. 24, 2020, provisional application No. 62/994,019, filed on Mar. 24, 2020, provisional application No. 62/994,021, filed on Mar. 24, 2020.

(51) Int. Cl.
*A61B 1/018* (2006.01)
*A61B 1/12* (2006.01)
*F16K 21/20* (2006.01)

(52) U.S. Cl.
CPC .......... *F16K 21/20* (2013.01); *A61B 1/00082* (2013.01); *A61B 1/018* (2013.01)

(58) Field of Classification Search
CPC . A61B 1/00128; A61B 1/00137; A61B 1/015; A61B 1/018; A61B 1/12; A61B 1/126; A61B 1/127; F16K 21/20
See application file for complete search history.

(56) References Cited

U.S. PATENT DOCUMENTS

| | | | | |
|---|---|---|---|---|
| 4,736,732 | A * | 4/1988 | Shimonaka | A61M 1/7413 600/158 |
| 4,794,913 | A * | 1/1989 | Shimonaka | A61M 1/7413 600/154 |
| 4,800,869 | A * | 1/1989 | Nakajima | A61B 1/00068 600/158 |
| 6,334,844 | B1 * | 1/2002 | Akiba | A61B 1/00068 600/156 |
| 6,346,075 | B1 | 2/2002 | Arai et al. | |
| 8,273,014 | B2 * | 9/2012 | Ushijima | G02B 23/2476 600/152 |
| 8,568,303 | B2 * | 10/2013 | Yamane | A61B 1/12 600/156 |
| 2010/0049001 | A1 * | 2/2010 | Yamane | A61B 1/015 600/159 |
| 2011/0208003 | A1 * | 8/2011 | Yamane | A61B 1/12 600/159 |
| 2011/0298169 | A1 * | 12/2011 | Nguyen | A61B 1/125 269/86 |
| 2012/0088973 | A1 * | 4/2012 | Morimoto | A61B 1/00068 600/156 |
| 2012/0088975 | A1 * | 4/2012 | Morimoto | A61B 1/00068 600/159 |
| 2015/0305599 | A1 * | 10/2015 | Murayama | A61B 1/00119 600/159 |
| 2016/0302646 | A1 * | 10/2016 | Hamazaki | A61B 1/00 |
| 2018/0361034 | A1 * | 12/2018 | Tobien | F16K 31/5245 |
| 2019/0125167 | A1 * | 5/2019 | Taniguchi | A61B 1/015 |
| 2019/0350441 | A1 * | 11/2019 | Saiga | A61B 1/00068 |
| 2019/0350444 | A1 * | 11/2019 | Saiga | A61B 1/00068 |
| 2019/0350445 | A1 * | 11/2019 | Saiga | G02B 23/2476 |
| 2019/0350446 | A1 * | 11/2019 | Saiga | A61B 1/00068 |
| 2020/0016637 | A1 * | 1/2020 | Still | A61B 1/125 |
| 2020/0187756 | A1 * | 6/2020 | Maurice | A61B 1/126 |
| 2020/0355281 | A1 * | 11/2020 | Harris | F16K 11/0712 |
| 2020/0375434 | A1 * | 12/2020 | Scutti | A61B 1/00137 |
| 2020/0386330 | A1 * | 12/2020 | Stanton | F16K 11/0712 |
| 2021/0007586 | A1 * | 1/2021 | Gavalis | A61B 1/00068 |
| 2021/0076910 | A1 * | 3/2021 | Saiga | A61B 1/00137 |
| 2021/0076914 | A1 * | 3/2021 | Arai | G02B 23/24 |

FOREIGN PATENT DOCUMENTS

| | | |
|---|---|---|
| JP | 2007111266 A | 5/2007 |
| WO | 2019225562 A1 | 11/2019 |

OTHER PUBLICATIONS

International Search Report and Written Opinion for the International Patent Application No. PCT/US2021/023482, mailed Jul. 9, 2021, 12 pages.

International Search Report and Written Opinion for the International Patent Application No. PCT/US2021/023484, mailed Jul. 9, 2021, 12 pages.

International Search Report and Written Opinion for the International Patent Application No. PCT/US2021/023478, mailed Jun. 10, 2021, 49 pages.

* cited by examiner

100

SUCTION VALVE ASSEMBLY 102

SUCTION VALVE WELL 104

| SUCTION CHANNEL 106 | WORKING CHANNEL 108 |
| BALLOON CHANNEL 114 | ATMOSPHERIC CHANNEL 116 |

SUCTION VALVE SET 118

| WORKING CHANNEL VALVE 120 | BALLOON VALVE 122 | ATMOSPHERIC VALVE 124 |

VALVE INTERFACE MECHANISM 126

| BIASING MEMBER SET 128 | USER INTERFACE MECHANISM 130 |

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
|---|---|---|
| AIR OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |
|---|---|---|

VALVE INTERFACE MECHANISM 226

| BIASING MEMBER SET 228 | USER INTERFACE MECHANISM 230 |
|---|---|

PRIMARY VALVE WATER OUTPUT STATE 1215-2

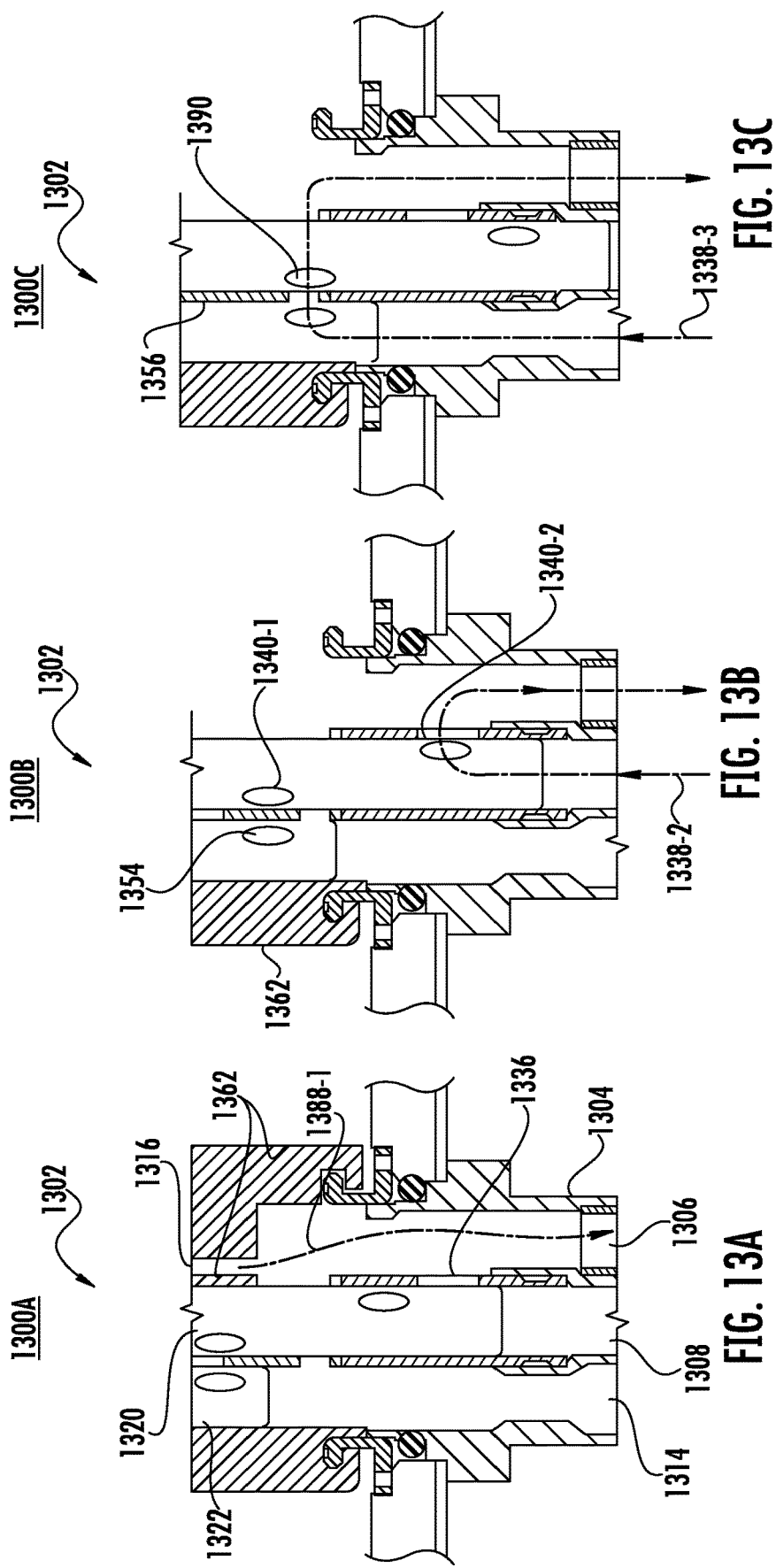

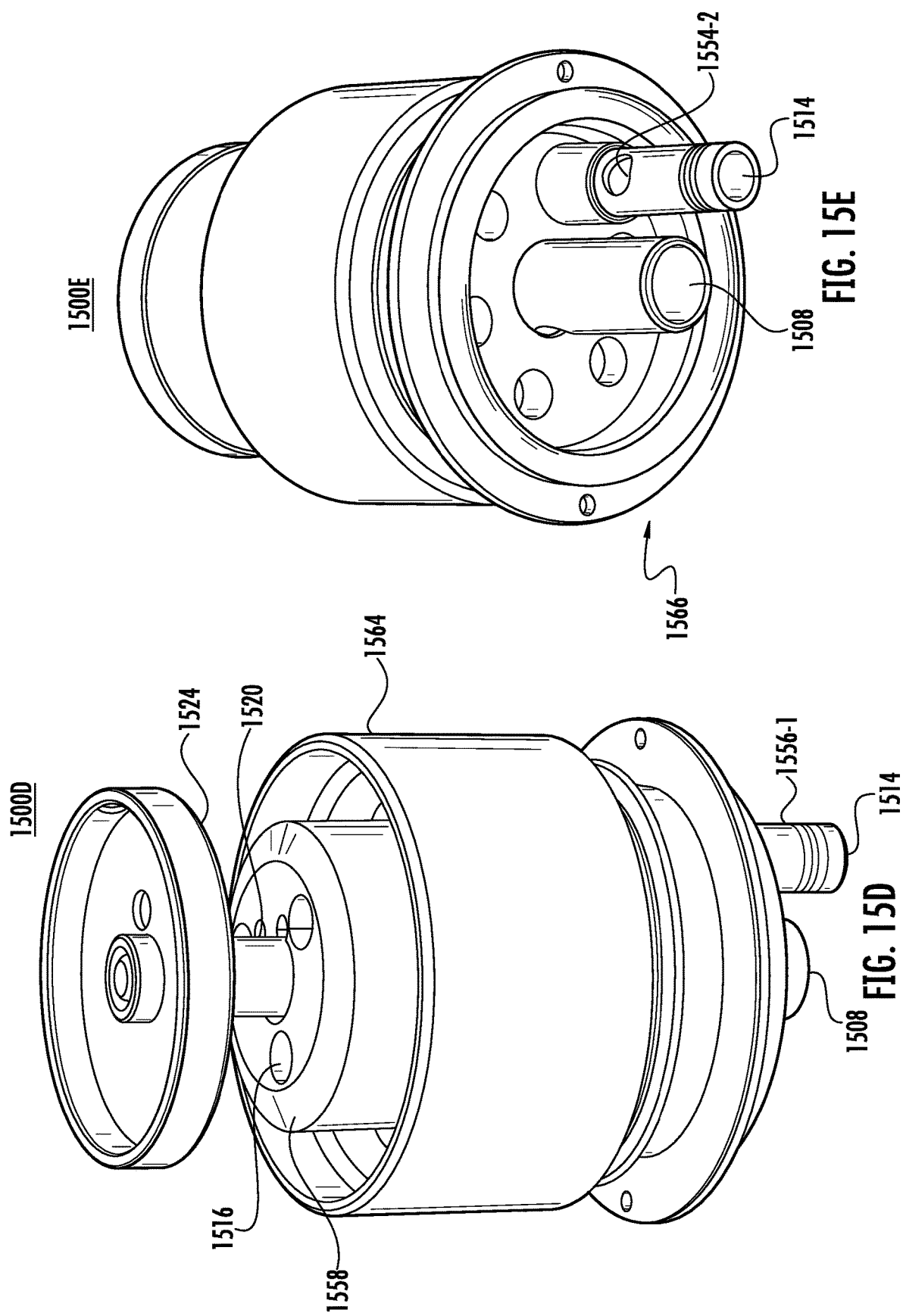

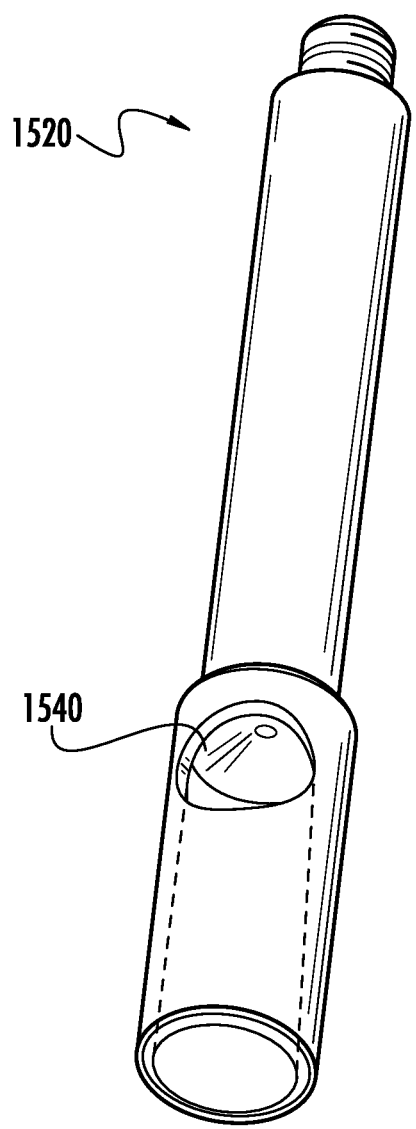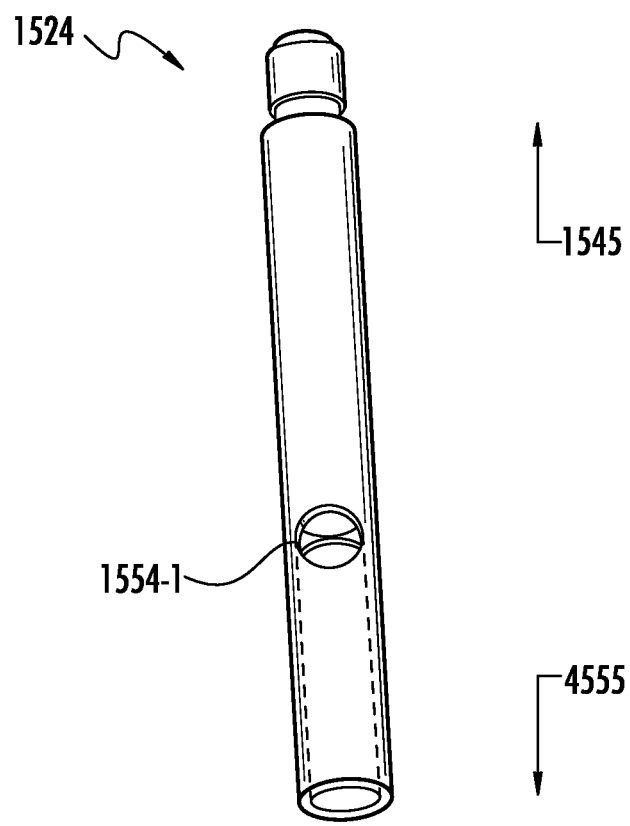
FIG. 15H
FIG. 15I

DEVICES, SYSTEMS, AND METHODS FOR ENDOSCOPE FLUIDICS

PRIORITY

The present application claims the benefit of priority under 35 U.S.C. § 119 to U.S. Provisional Application Ser. Nos. 62/994,008, 62/994,015, 62/994,018, 62/994,019, 62/994,021, and 62/994,024, each filed Mar. 24, 2020, the disclosures of which are incorporated herein by reference in their entirety.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems and methods of the present disclosure.

SUMMARY

In one aspect, the present disclosure relates to a medical device comprising a suction valve set and a valve interface mechanism. The suction valve set may include a working channel valve, a balloon valve, and an atmospheric valve. The working channel valve may control flow through a working channel of a valve well. The balloon valve may control flow through a balloon channel of the valve well. The atmospheric valve may control flow through an atmospheric channel of the valve well. The suction valve set may be configurable between a first state, a second state, and a third state. The first state is to place a suction channel of the valve well in fluid communication with the atmospheric channel, the second state is to place the suction channel in fluid communication with the working channel, and the third state is to place the suction channel in fluid communication with the balloon channel. The valve interface mechanism may include a set of one or more biasing members, a bowl, and a linkage. The bowl may include a top, a bottom, and a cylindrical portion with an interior. The linkage may extend from the bottom of the bowl and comprise a top, a bottom, and a tubular structure with an interior. In various embodiments, at least a portion of the tubular structure of the linkage is configured for insertion into the balloon channel of the valve well. In several embodiments, the balloon valve is configured to extend through at least a portion of the interior of the bowl and at least a portion of the interior of the linkage. In many embodiments, the valve interface mechanism may be configured to displace at least a portion of the balloon valve toward the bottom of the linkage to place the suction channel in fluid communication with the balloon channel. In several embodiments, the balloon valve may include a first radial hole and the linkage may comprise a second radial hole. In many such embodiments, the valve interface mechanism may be configured to align the first radial hole and the second radial hole to place the suction channel in fluid communication with the balloon channel. In some such embodiments, the valve interface mechanism may be configured to misalign the first radial hole and the second radial hole to block flow through the balloon channel. In various such embodiments, the set of one or more biasing members may be configured to bias the first radial hole out of alignment with the second radial hole. In one or more embodiments, the tubular structure of the linkage is nonconcentric with the cylindrical portion of the bowl. In some embodiments, the balloon valve is concentric with the linkage and nonconcentric with the bowl when extended through at least a portion of the interior of the bowl and at least a portion of the interior of the linkage. In many embodiments, the set of one or more biasing members may be configured to bias the balloon valve to block flow through the balloon channel. In various embodiments, the linkage may comprise at least a portion of the balloon channel. In several embodiments, the valve interface mechanism may be configured to displace at least a portion of the balloon valve out of the bottom of the linkage to place the suction channel in fluid communication with the balloon channel. In many such embodiments, the balloon valve may include a plunger valve. In various such embodiments, the linkage may comprise a radial slot. In one or more embodiments, the valve interface mechanism may comprise a lever to configure the balloon valve to place the suction channel in fluid communication with the balloon channel. In many embodiments, the valve interface mechanism may be configured to displace at least a portion of the balloon valve toward the top of the bowl to place the suction channel in fluid communication with the balloon channel.

In another aspect, the present disclosure relates to a method. The method may include placing a suction channel of a valve well in fluid communication with an atmospheric channel of the valve well based on operation of a user interface mechanism to a first state. The method may include, placing the suction channel of the valve well in fluid communication with a working channel of the valve well based on operation of the user interface mechanism to a second state. The method may include placing the suction channel of the valve well in fluid communication with a balloon channel of the valve well based on operation of the user interface mechanism to a third state. In some embodiments, the method may include rotating an interface member in a first direction to operate the user interface mechanism to the second state and rotating the interface member in a second direction to operate the user interface mechanism to the third state. In many embodiments, the method may include rotating the interface member adjust one or more valves in a suction valve set via a cam. In several embodiments, the method may include operating one or more of a lever, a rocker switch, and an interface member to adjust between one or more of the first state, the second state, and the third state.

In still another aspect, the present disclosure relates to a method. The method may include configuring a suction valve set to place a suction channel of a valve well in fluid communication with an atmospheric channel of the valve well based on operation of a valve interface mechanism to a first state, the suction valve set comprising a working channel valve, a balloon valve, and an atmospheric valve. The method may include configuring the suction valve set to place the suction channel of the valve well in fluid communication with a working channel of the valve well based on operation of the valve interface mechanism to a second state, the valve interface mechanism including a bowl comprising a top, a bottom, and a cylindrical portion with an interior, and a linkage extending from the bottom of the bowl, the linkage comprising a top, a bottom, and a tubular structure with an interior, wherein the balloon valve is configured to extend through at least a portion of the interior of the bowl and at least a portion of the interior of the linkage. The method may include configuring the suction valve set to place the suction channel of the valve well in fluid communication with a balloon channel of the valve well based on operation of the valve interface mechanism to a third state. In some embodiments, the method may include displacing at least a portion of the balloon valve toward the bottom of the linkage to place the suction channel in fluid communication with the balloon channel. In various embodiments, the method may include displacing at least a portion of the balloon valve toward the top of the bowl to place the suction channel in fluid communication with the balloon channel. In many embodiments, the method may include inserting at least a portion of the tubular structure of the linkage into the balloon channel of the valve well. In several embodiments, the method may include displacing at least a portion of the balloon valve out of the bottom of the linkage to place the suction channel in fluid communication with the balloon channel. In one embodiment, the method may include biasing the first radial hole out of alignment with the second radial hole with a set of one or more biasing members. In various embodiments, the method may include aligning a first radial hole included in the balloon valve with a second radial hole included in the linkage to place the suction channel in fluid communication with the balloon channel. In some embodiments, the method may include misaligning a first radial hole included in the balloon valve with a second radial hole included in the linkage to block flow through the balloon channel.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

FIGS. 13A-13C illustrate various aspects of an exemplary suction valve assembly, according to one or more embodiments described herein.

FIGS. 15A-15I illustrate various aspects of an exemplary suction valve assembly, according to one or more embodiments described herein.

DETAILED DESCRIPTION

Figure 3A:
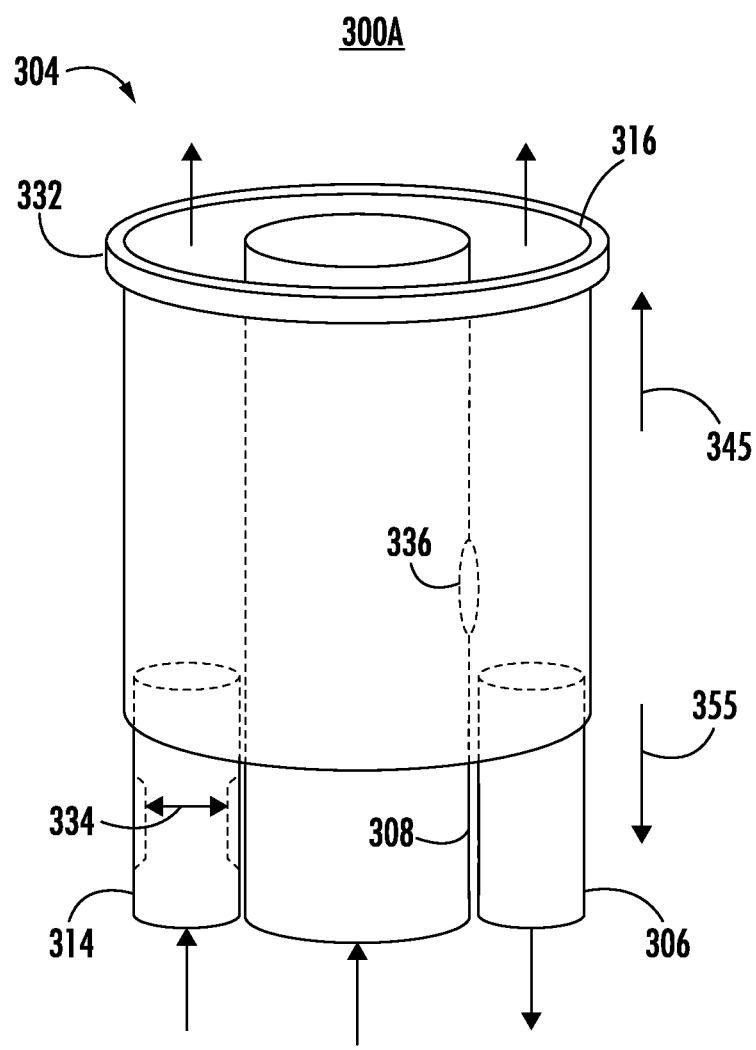
FIGS. 3A-3D illustrate various aspects of an exemplary suction valve well, according to one or more embodiments described herein.

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked and/or the flow of water may be controlled from water input channel 208 to one of water output channel 212 and balloon channel 214.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to facilitate capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a levers, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve wells block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
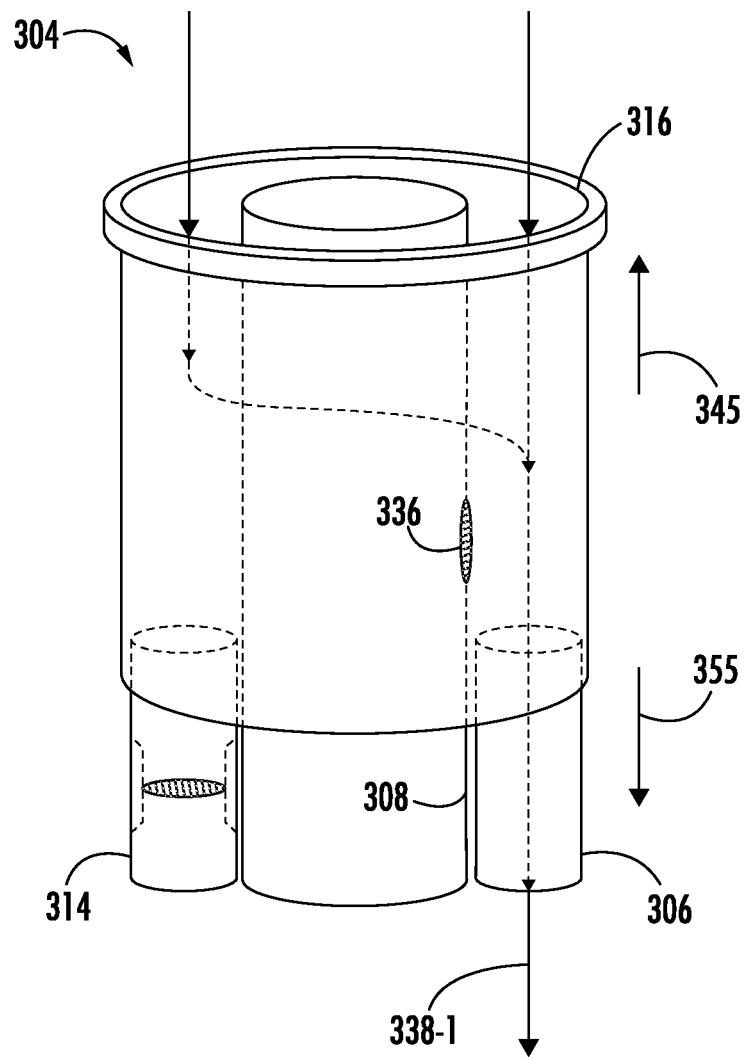

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Figure 3C:
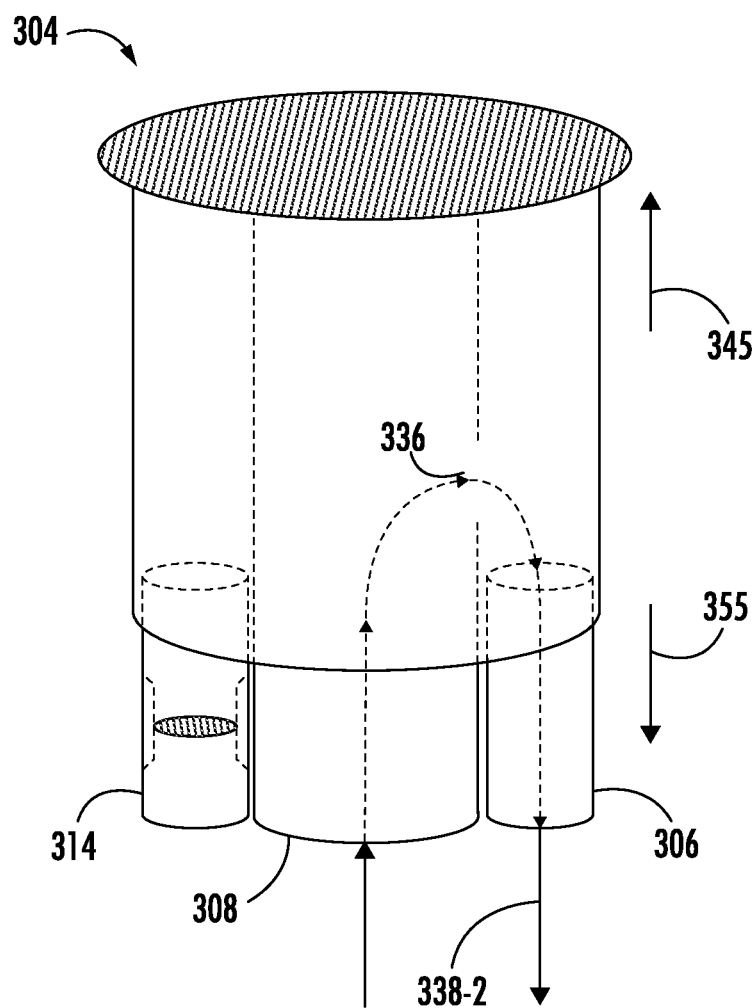

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
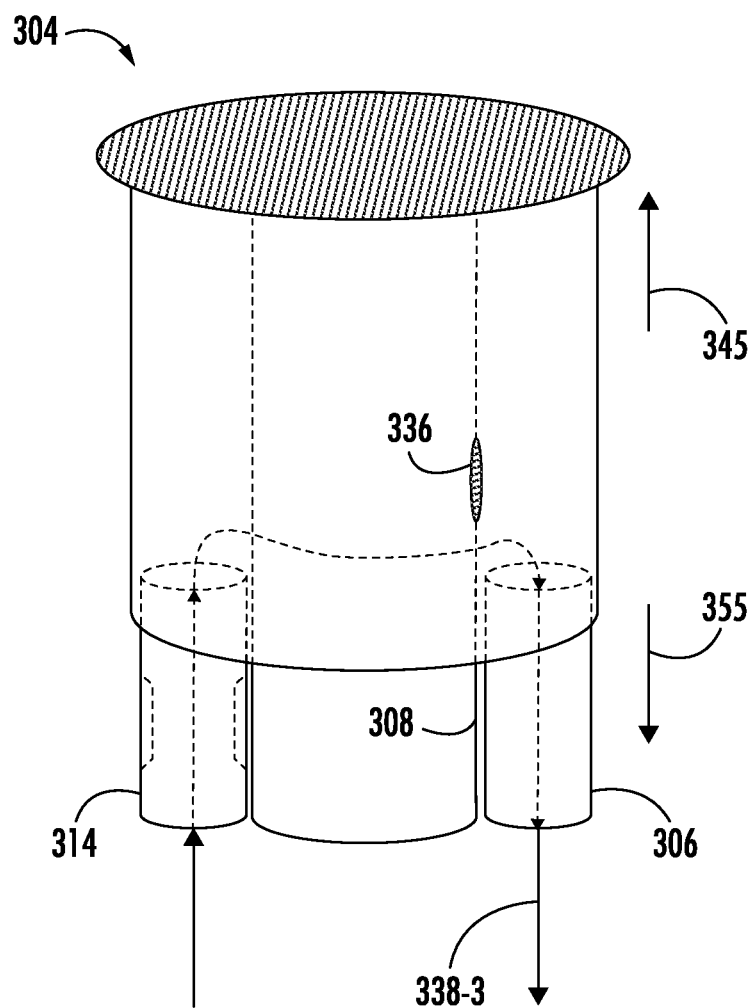

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
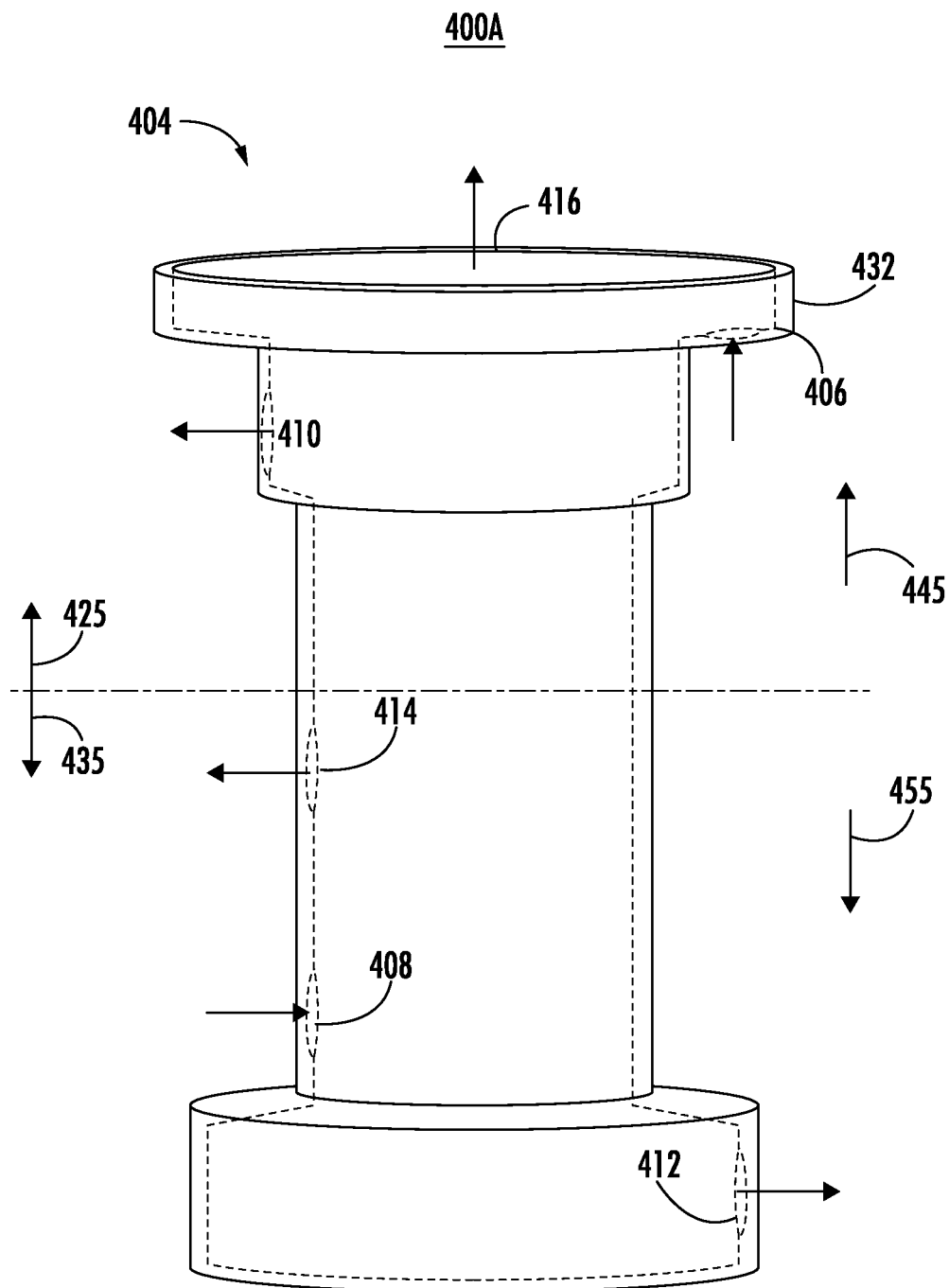
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
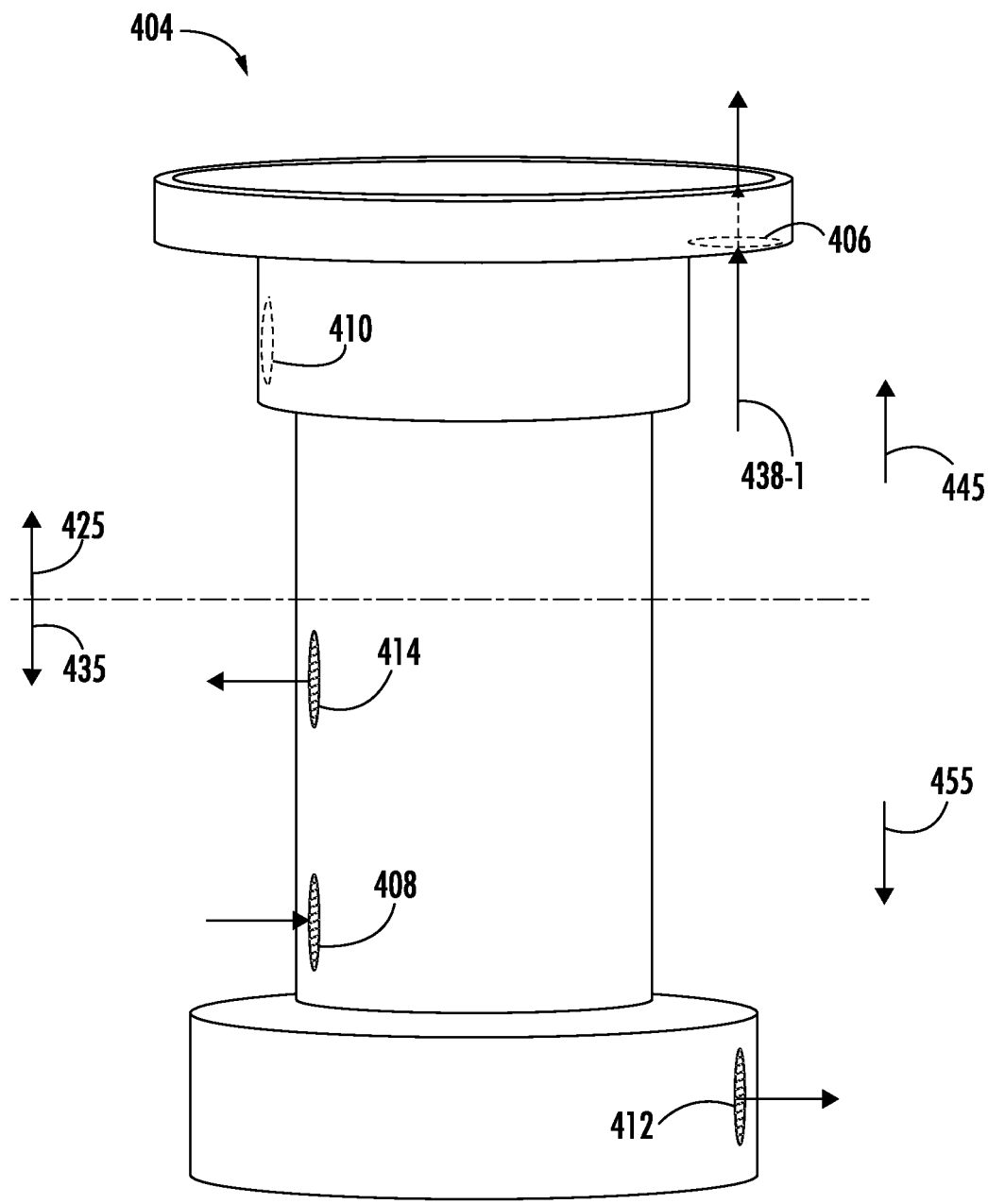

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
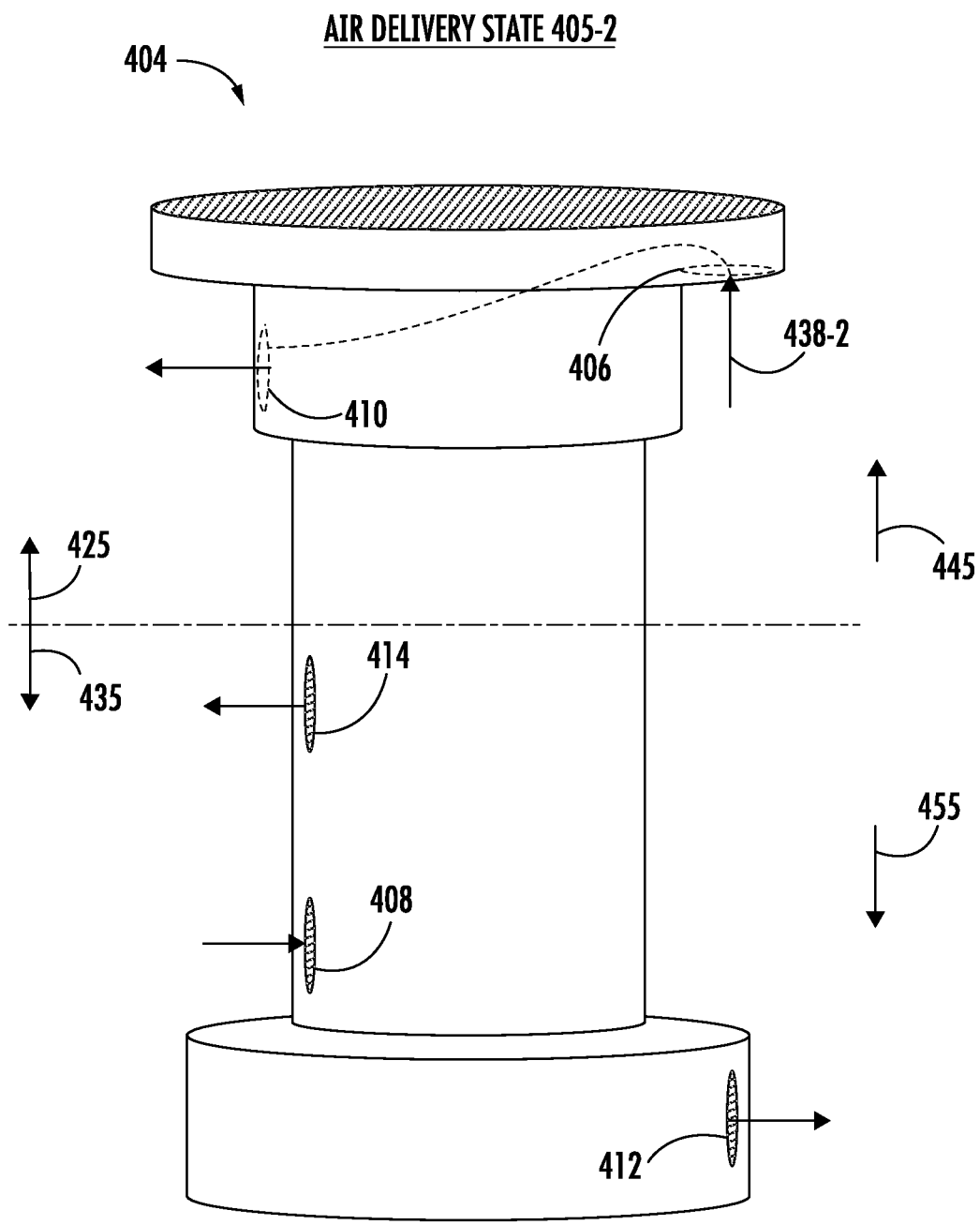

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
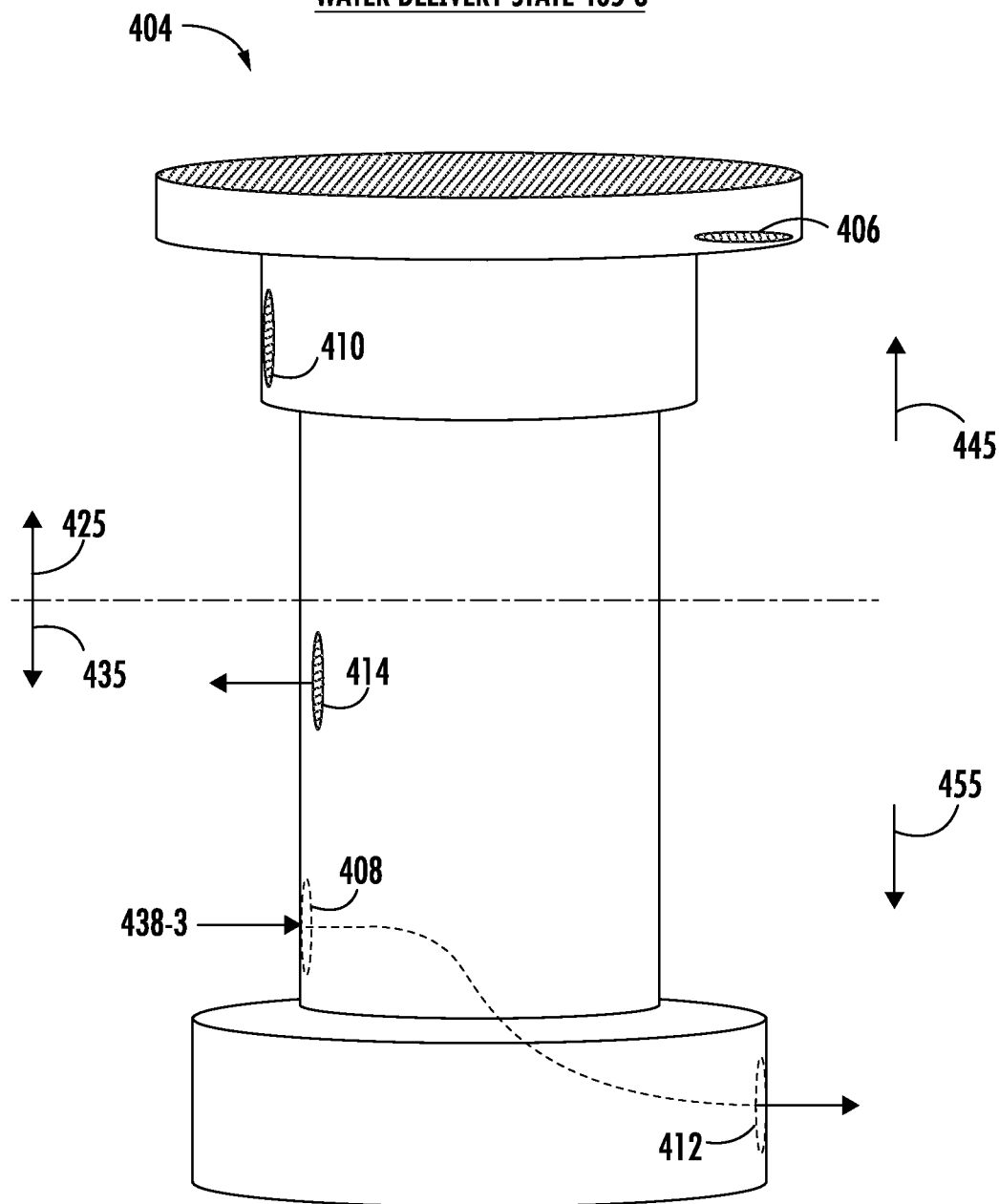

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
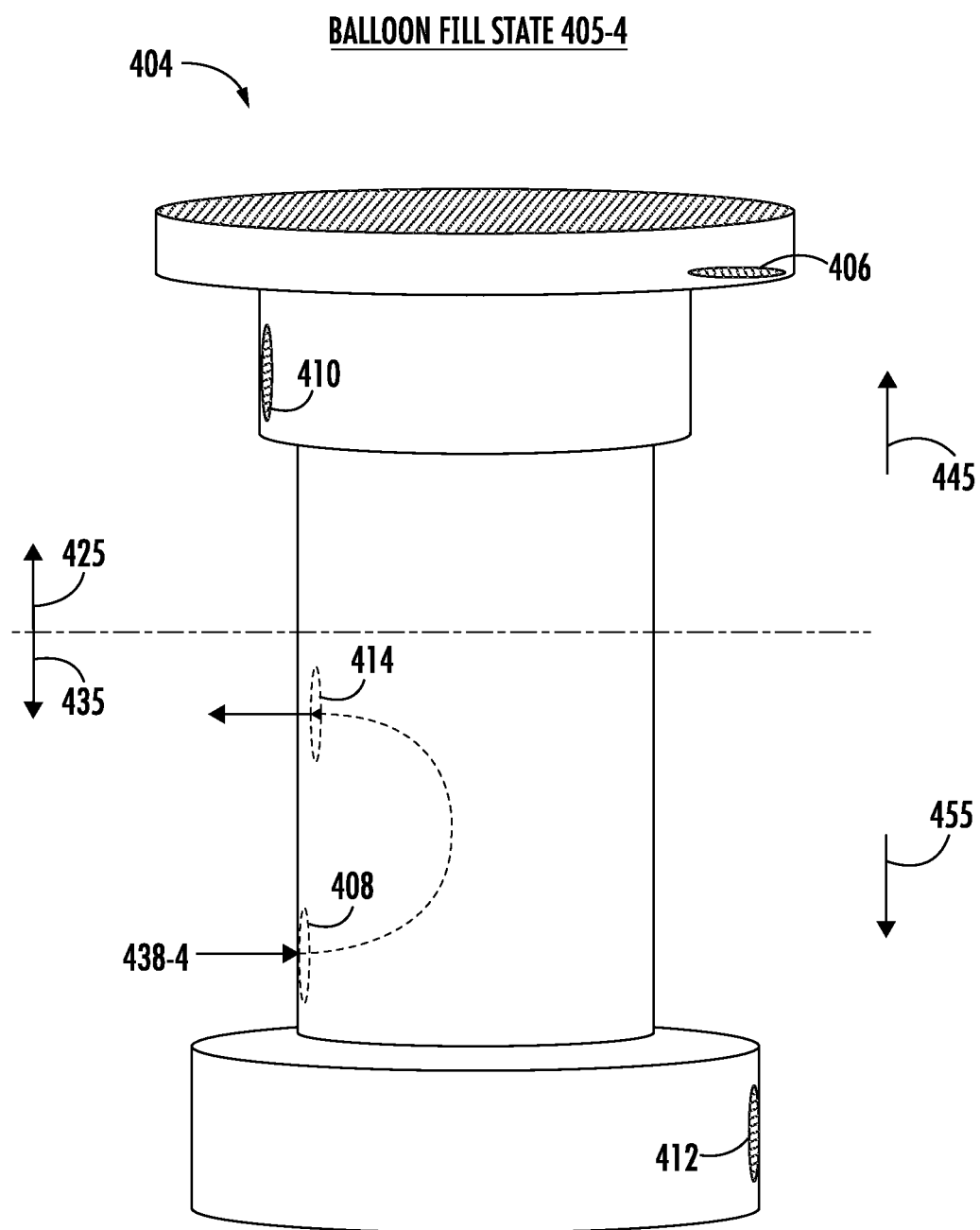

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
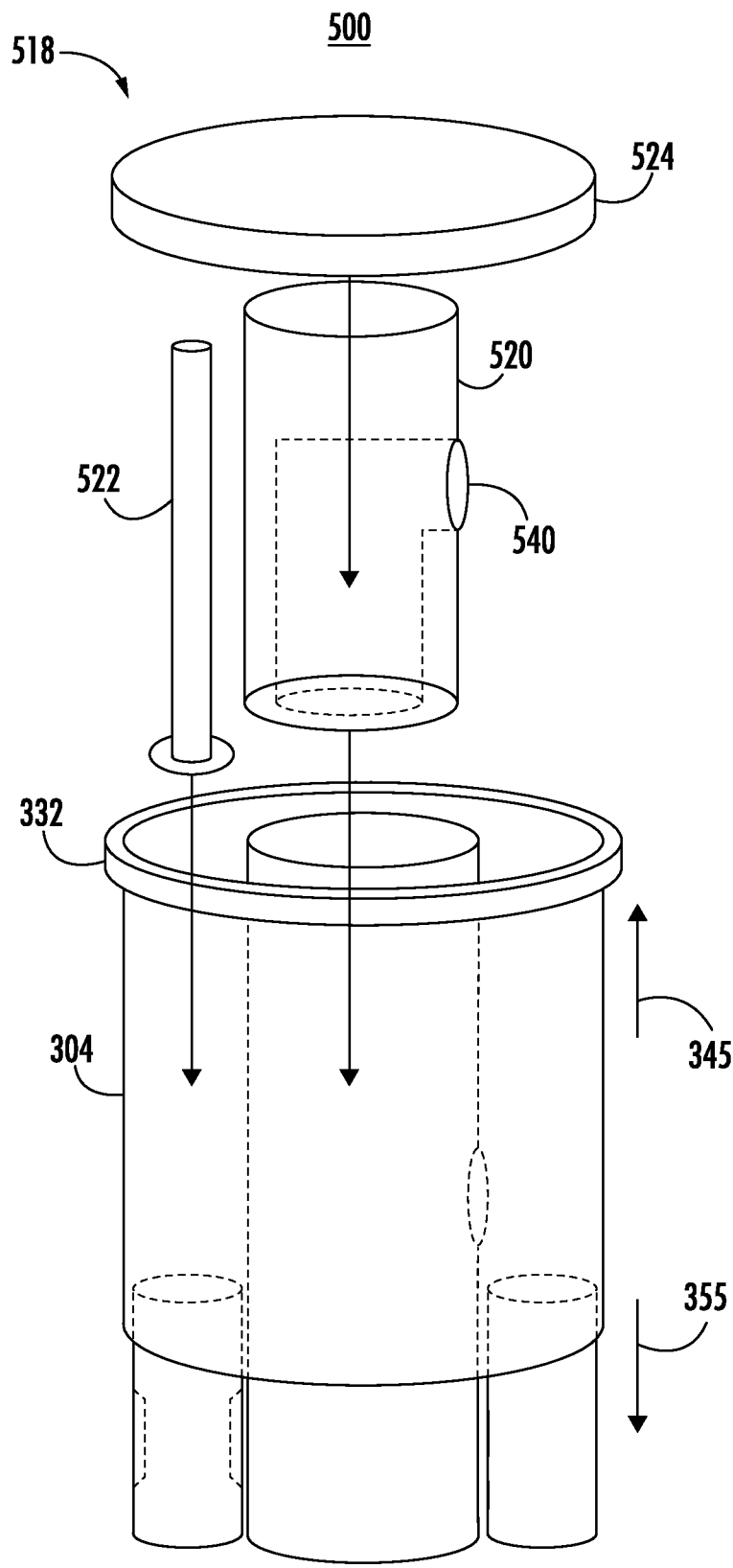
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
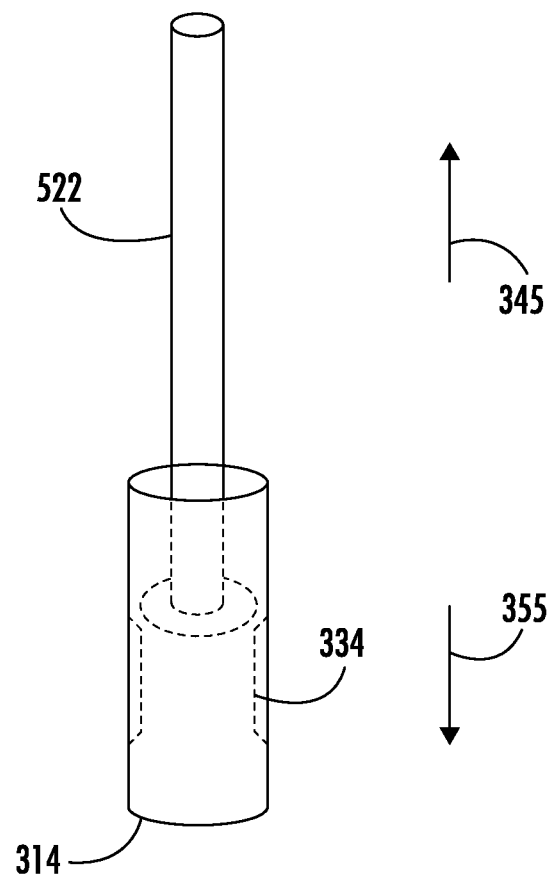
FIGS. 6A-8C illustrate various aspects of exemplary valves in suction valve sets, according to one or more embodiments described herein.
Figure 6B:
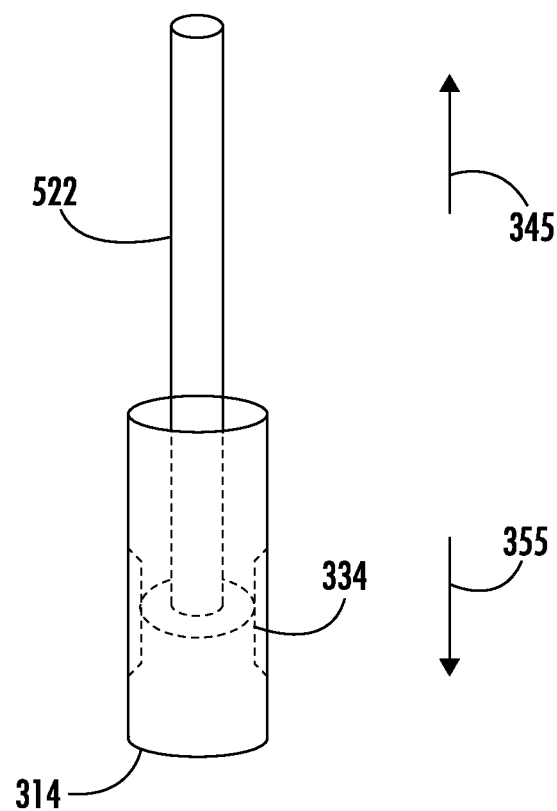

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
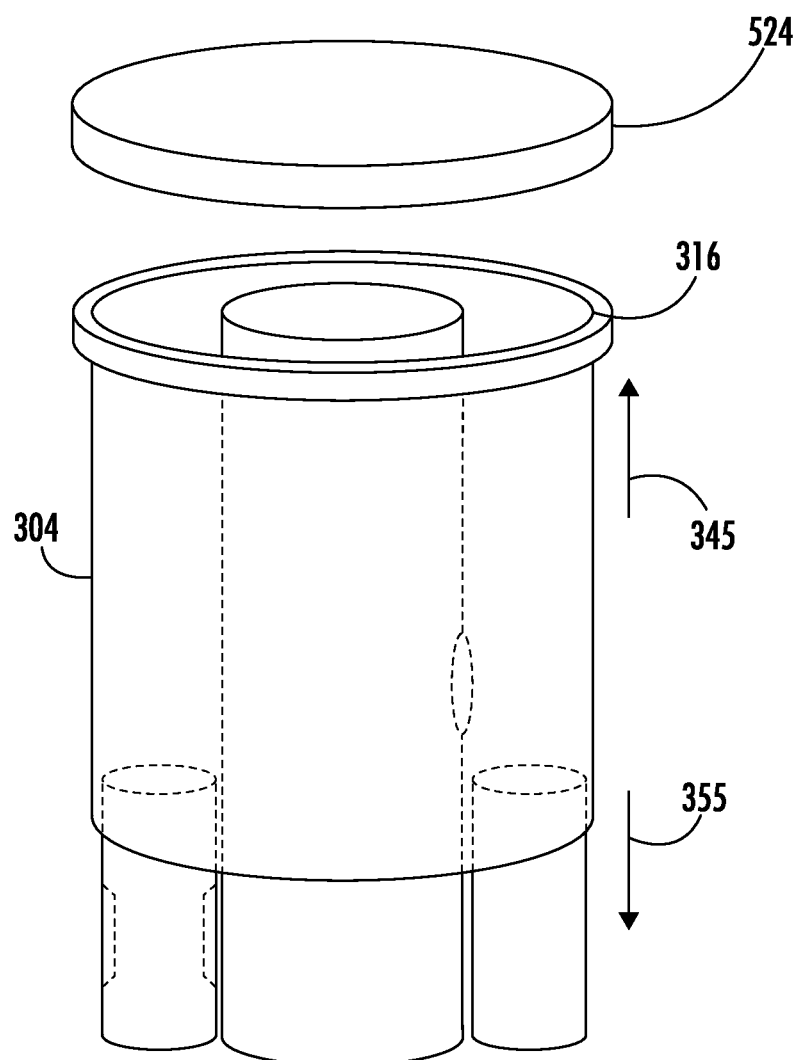
Figure 7B:
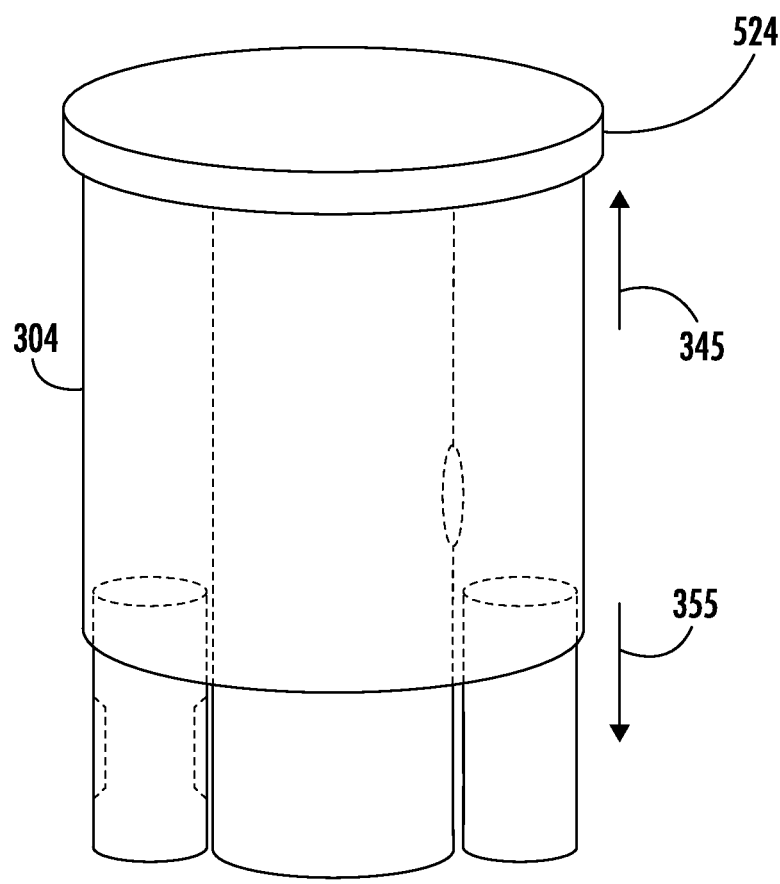

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
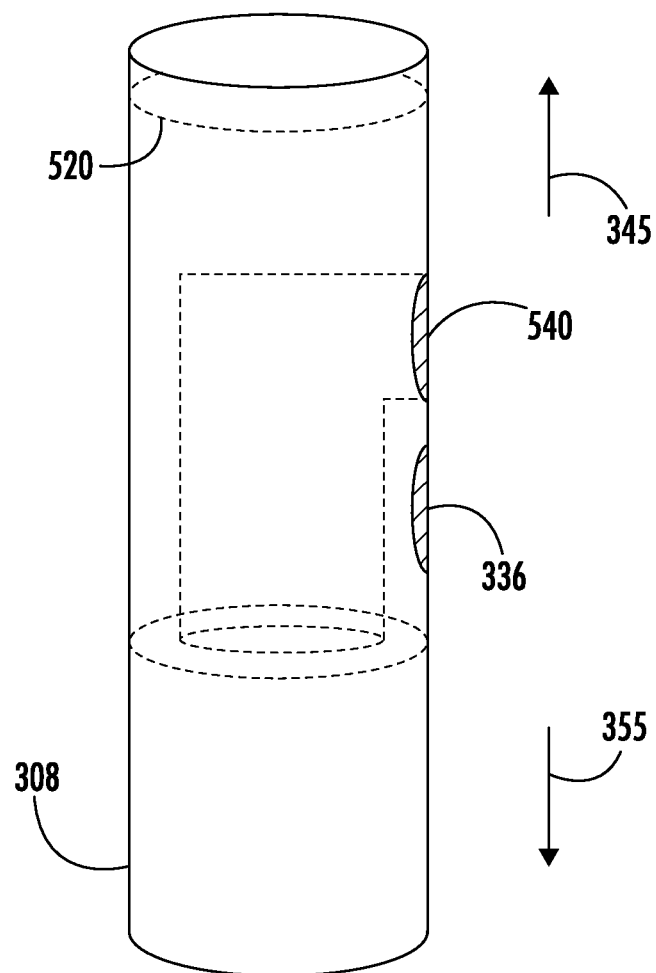
Figure 8B:
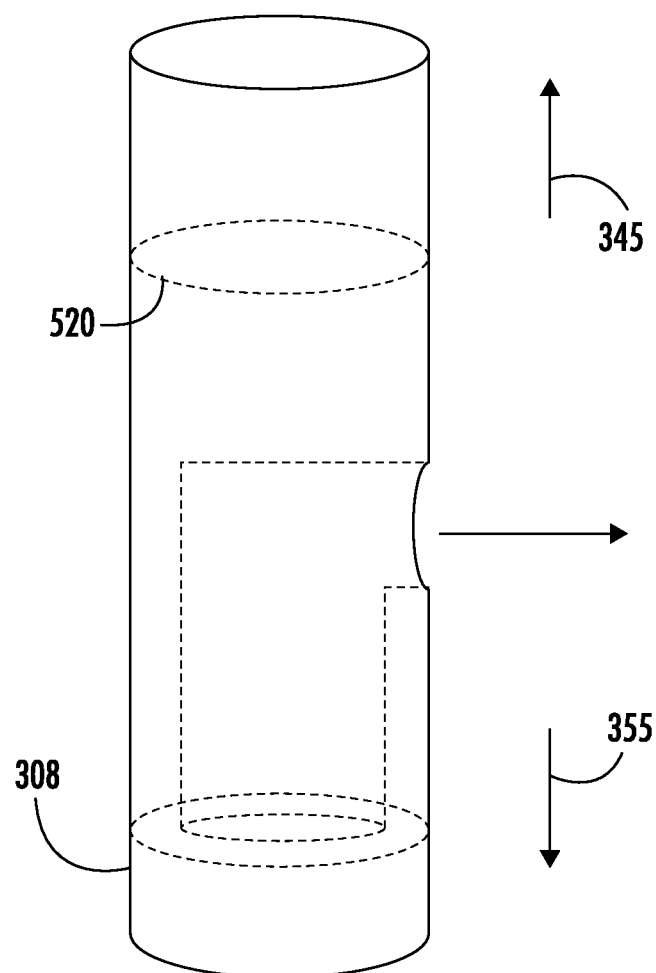
Figure 8C:
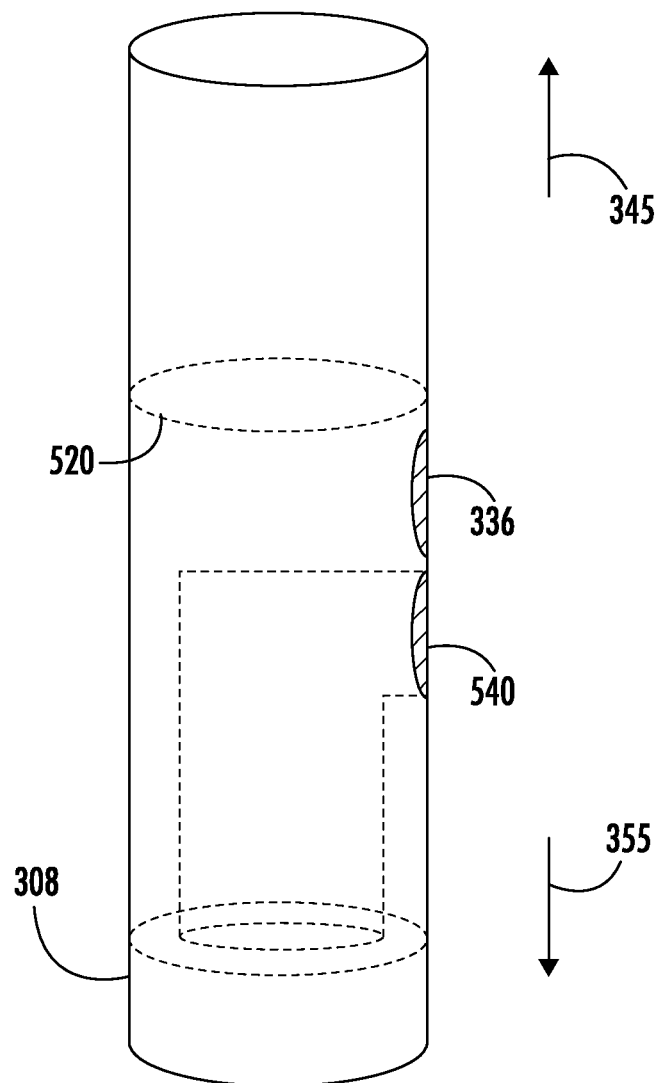

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit flow through working channel 308. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel valve radial hole 440 is below well radial hole 336.

Figure 9:
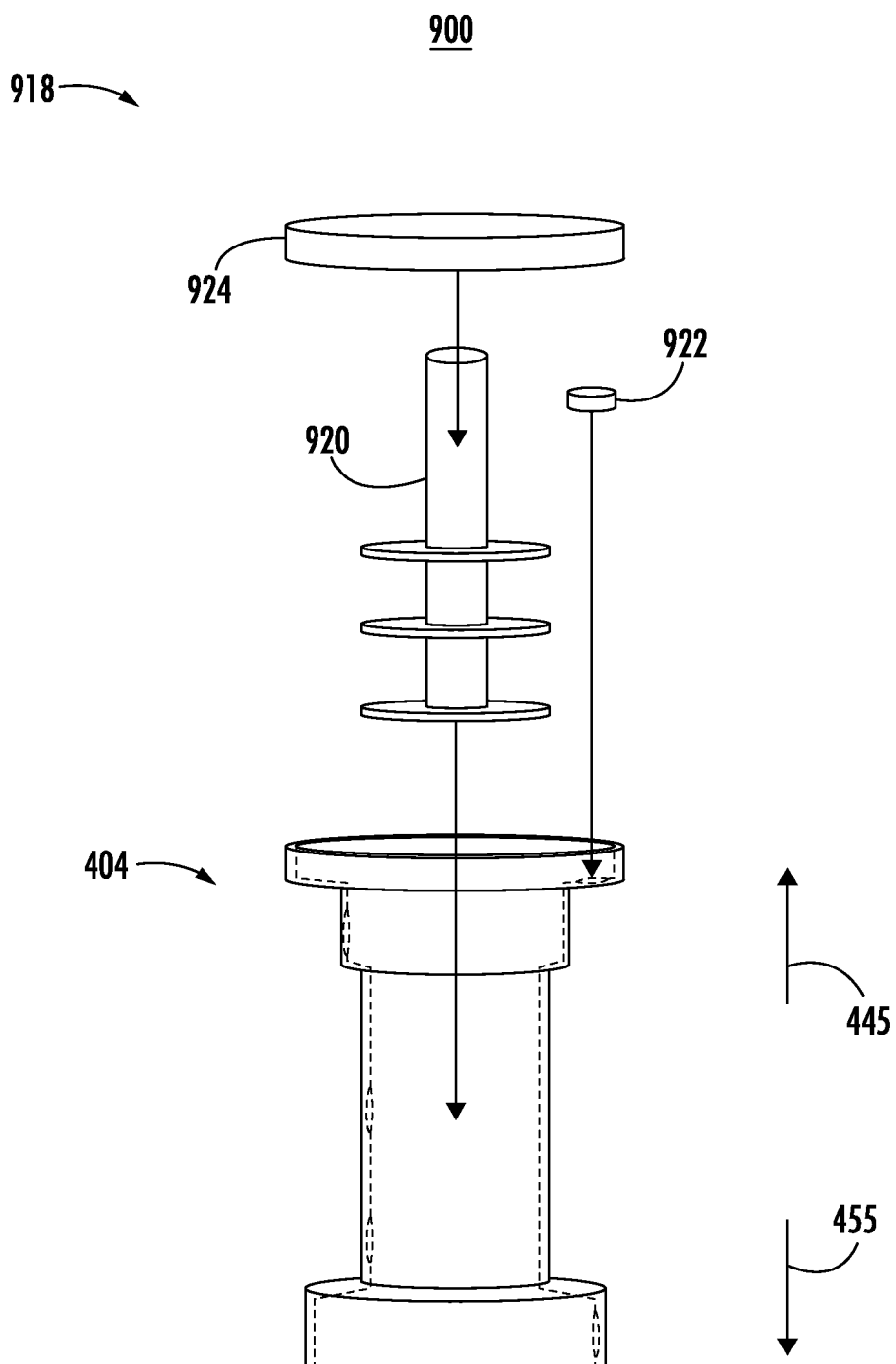
FIG. 9 illustrates an exemplary AW valve set, according to one or more embodiments described herein.

Referring to FIG. 9, environment 900 illustrates AW valve set 918 in conjunction with Aw valve well 404. Aw valve set 918 may include primary control valve 920, air input valve 922, and atmospheric valve 924. In several embodiments, the primary control valve 920 may be inserted into the AV valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel valve radial hole 440 is below well radial hole 336.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
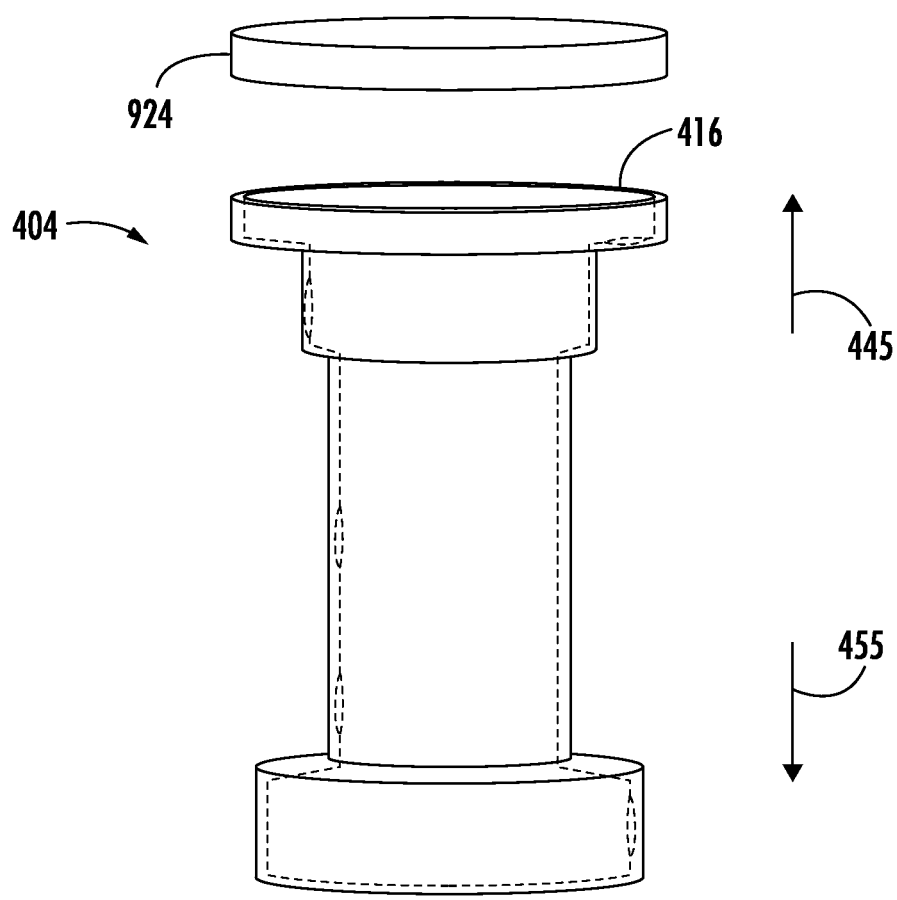
FIGS. 10A-12C illustrate various aspects of exemplary valves in AW valve sets, according to one or more embodiments described herein.
Figure 10B:
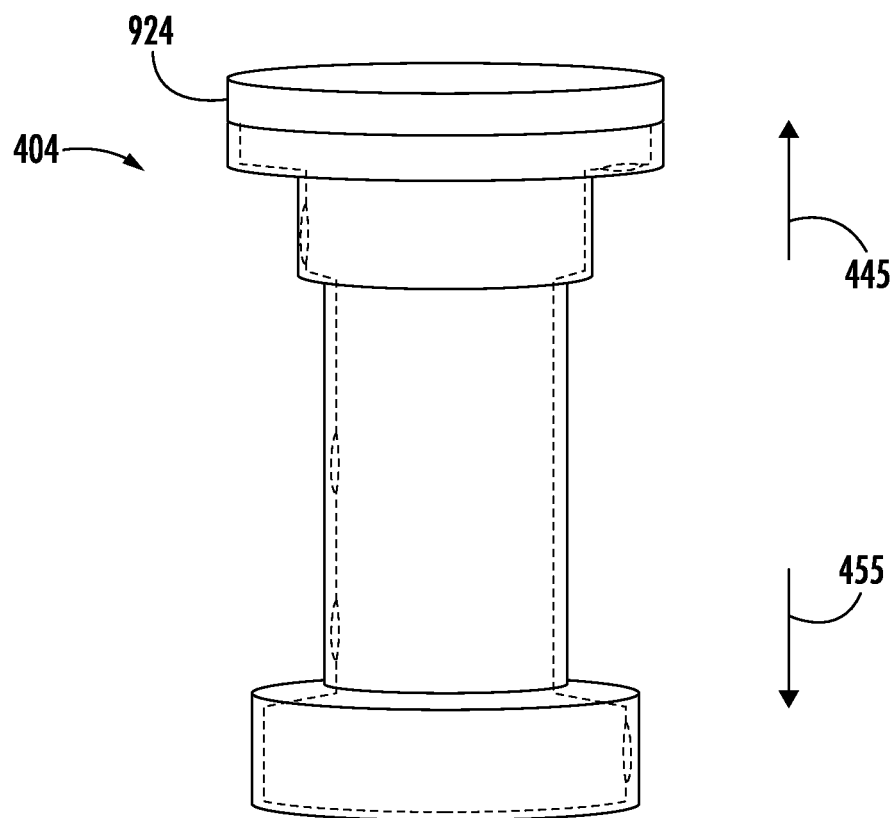

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
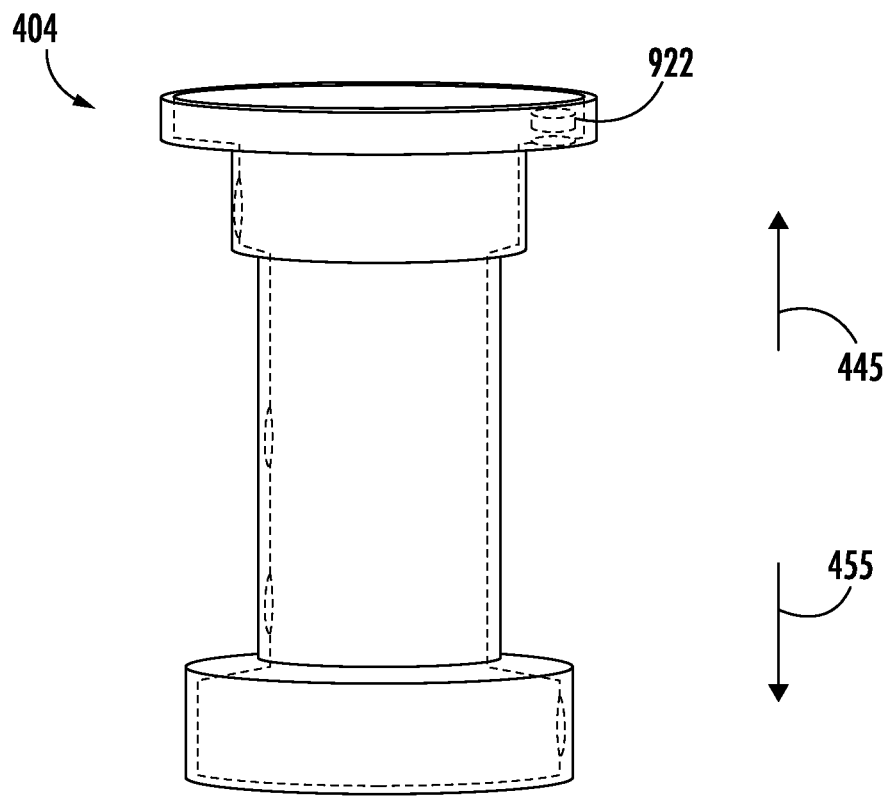
Figure 11B:
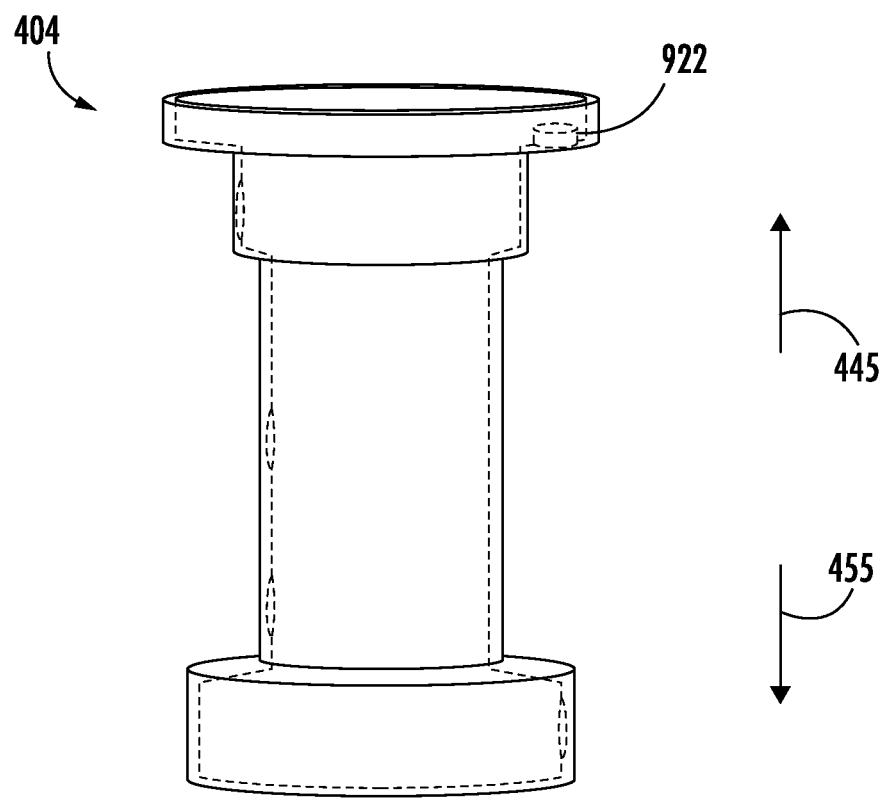

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
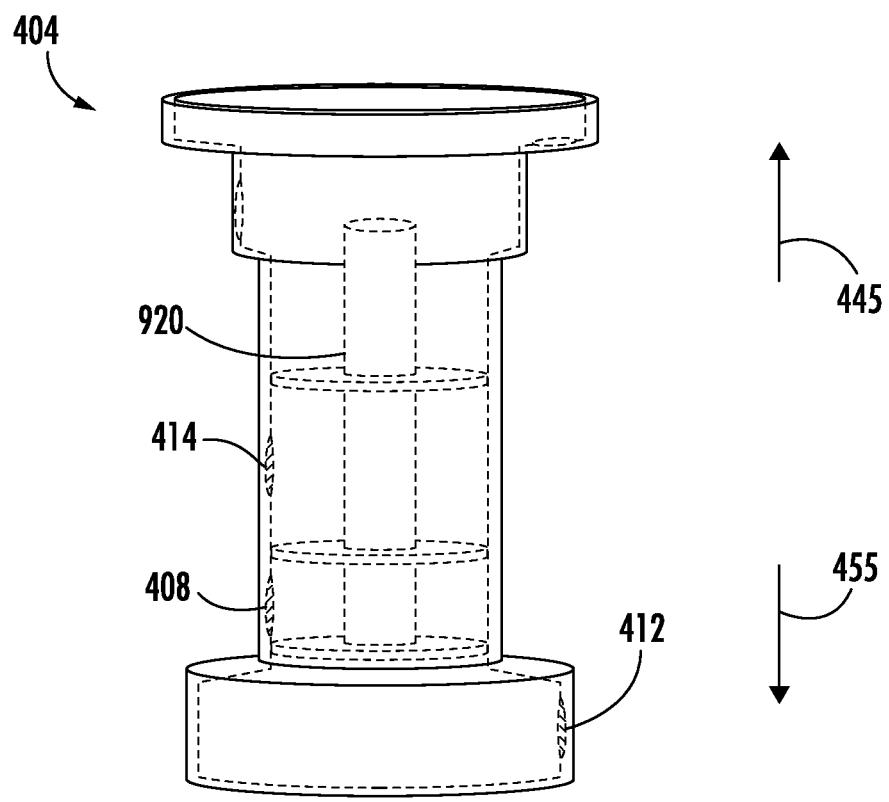
Figure 12B:
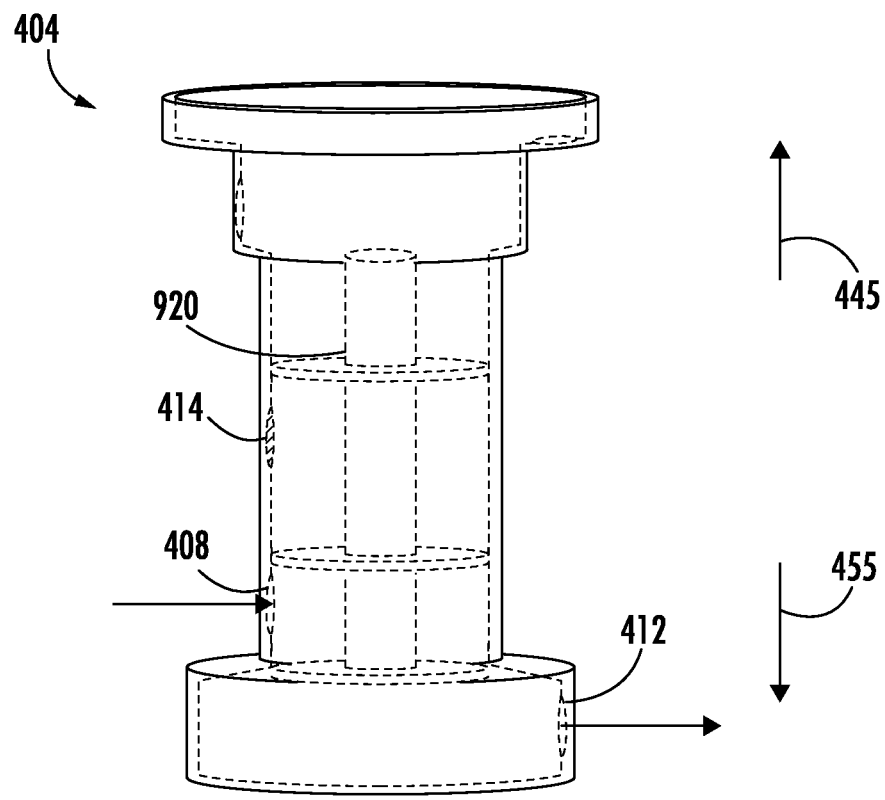
Figure 12C:
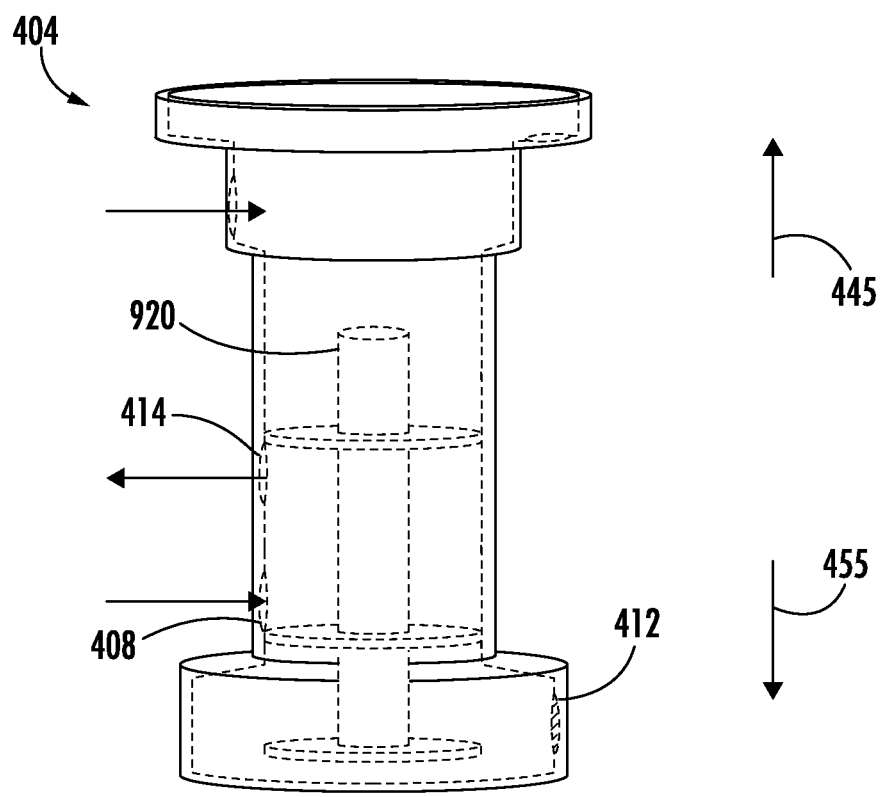

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416.

FIGS. 13A-13C illustrate various aspects of an exemplary suction valve assembly 1302 in environments 1300A, 1300B, 1300C according to one or more embodiments described herein. In many embodiments, a cross section of one or more components may be illustrated in environments 1300A, 1300B, 1300C. In some embodiments, one or more components of FIGS. 13A-13C may be the same or similar to one or more other components described herein. Environments 1300A, 1300B, 1300C may include a suction valve assembly 1302. The illustrated portion of suction valve assembly 1302 includes a working channel valve 1320, a balloon valve 1322, an atmospheric channel 1316, a housing 1362, a linkage 1356, and a suction valve well 1304. The balloon valve 1322 may include a balloon valve radial hole 1354 and the working channel valve may include working channel valve radial holes 1340-1, 1340-2. The linkage 1356 may include a linkage hole 1390. The suction valve well 1304 may include a balloon channel 1314, a suction channel 1306 and a working channel 1308 with a well radial hole. In one or more embodiments described herein, working channel valve 1320 and balloon valve 1322 may each include one or more channels to place one or more holes (radial, top, and/or bottom holes) in fluid communication. For simplicity, a portion of the housing 1362 in environment 1300A is not illustrated in environments 1300B, 1300C. Embodiments are not limited in this context.

In various embodiments, one or more holes may be aligned by the valve interface mechanism in response to user input to control flow through the suction valve well 1304. For example, balloon valve radial hole 1354, linkage hole 1390, and working channel valve radial hole 1340-1 may be aligned to permit flow 1338-3. In some embodiments, vertical motion/displacement may be utilized to enable each of flows 1338-1, 1338-2, 1338-3. For instance, an interface member comprising a button may be depressed to cause the valve interface mechanism to align two or more holes. In such instances, the interface member may be depressed to a first stop to align working channel valve radial hole 1340-2 with well radial hole 1336 and depressed to a second stop to align balloon valve radial hole 1354 and working channel valve radial hole 1340-1 with linkage hole 1390. In some embodiments, the suction valve assembly may utilize three states.

In environment 1300A, suction valve assembly 1302 may be in a first state (e.g., atmospheric suction state) comprising flow 1388-1 from atmospheric channel 1316 to suction channel 1306. In various embodiments, the balloon valve 1322 and/or the working channel valve 1320 may block flow through the linkage hole 1390 in the first state. In some embodiments, the working channel valve 1320 may block flow through one or more of the well radial hole 1336, the working channel 1308 and the balloon channel 1314 in the first state. In several embodiments, the balloon valve 1322 may block flow through the balloon channel 1314 in the first state.

In environment 1300B, suction valve assembly 1302 may be in a second state (e.g., working channel suction state) comprising flow 1388-2 from working channel 1308 to suction channel 1306 via a hole in the bottom of working channel valve 1320, working channel valve radial hole 1340-2, and well radial hole 1336. In various embodiments, the balloon valve 1322 and/or the working channel valve 1320 may block flow through the linkage hole 1390 and/or the balloon channel 1314 in the second state.

In environment 1300C, suction valve assembly 1302 may be in a third state (e.g., balloon channel suction state) comprising flow 1388-3 from balloon channel 1314 to suction channel 1306 via a hole in the bottom of balloon valve 1322, linkage hole 1390, and working channel valve radial hole 1340-1. In various embodiments, the balloon valve 1322 and/or the working channel valve 1320 may block flow through the working channel 1308 in the third state.

Figure 14:
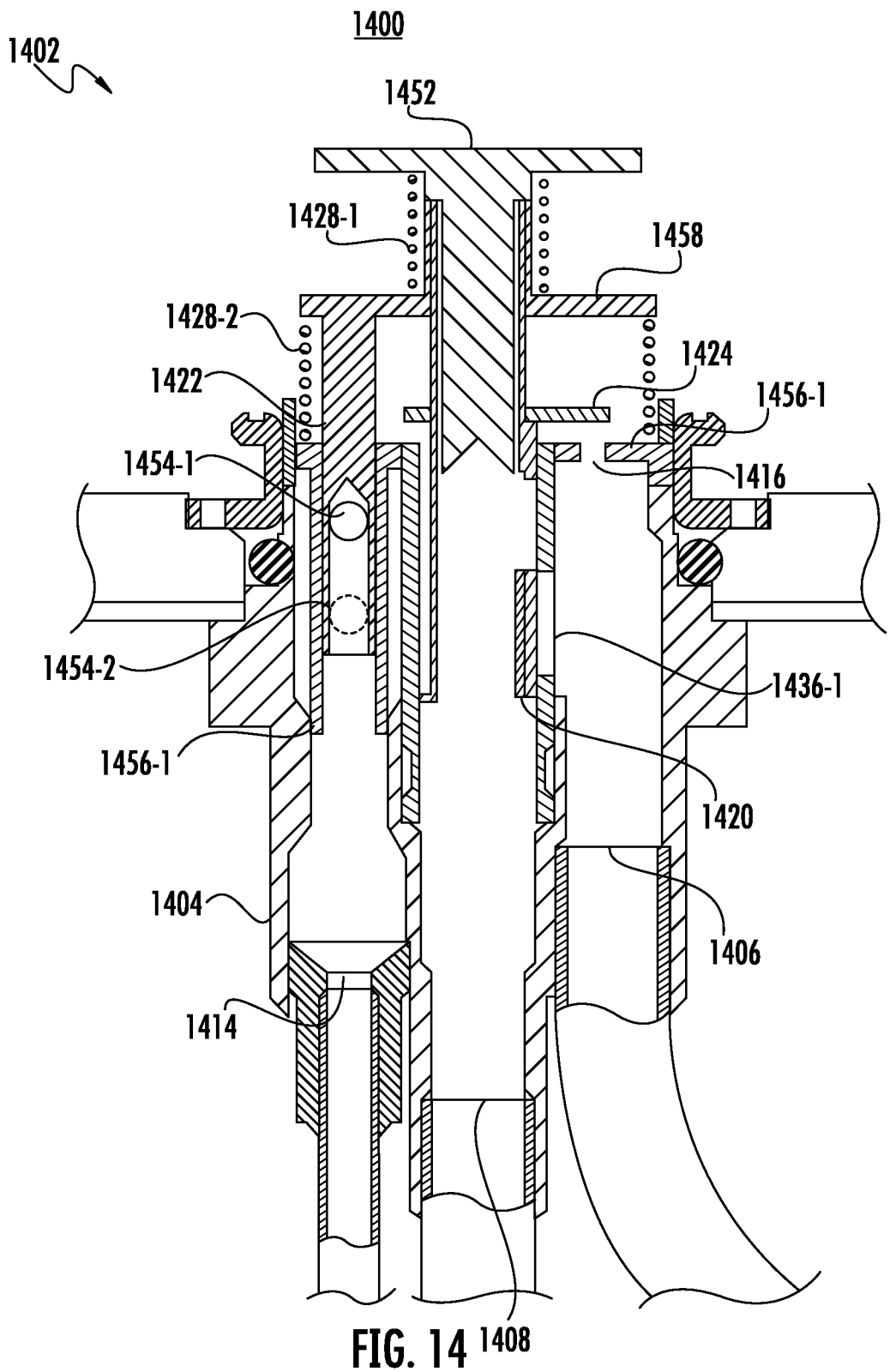
FIG. 14 illustrates various aspects of an exemplary suction valve assembly, according to one or more embodiments described herein.

FIG. 14 illustrates various aspects of an exemplary suction valve assembly 1402 in environment 1400, according to one or more embodiments described herein. In many embodiments, a cross section of one or more components may be illustrated in environment 1400. In some embodiments, one or more components of FIG. 14 may be the same or similar to one or more other components described herein. In environment 1400, the suction valve assembly 1402 may include interface 1452, biasing members 1428-1, 1428-2, hat 1458, balloon valve 1422 with balloon valve radial hole 1454-1, atmospheric valve 1424, working channel valve 1420, linkage 1456-1 with linkage radial hole 1454-2, linkage 1456-2 with atmospheric channel 1416, and suction valve well 1404. The suction valve well may include balloon channel 1414, working channel 1408 with well radial hole 1436-1 and suction channel 1408. In one or more embodiments described herein, interface 1452 may be depressed to cause balloon valve radial hole 1454-1 to align with linkage radial hole 1454-2 to place the balloon channel 1414 in fluid communication with the suction channel 1406. Embodiments are not limited in this context.

In some embodiments, the suction valve assembly 1402 may utilize the three states previously described (e.g., atmospheric suction state, working channel suction state, and balloon channel suction state). In various embodiments, interface 1452 may be depressed to cause the atmospheric valve 1424 to block flow through the atmospheric channel 1416 during transition from the first state to the second state. In many embodiments, interface 1452 may be depressed, thereby compressing biasing member 1428-1, to place working channel 1408 in fluid communication with suction channel 1406 during transition from the first state to the second state.

In several embodiments, interface 1452 may be depressed further, thereby compressing biasing member 1428-2, to place balloon channel 1414 in fluid communication with suction channel 1406 during transition from the second state to the third state. In many embodiments, interface 1452 may depress hat 1458 which in turn depresses balloon valve 1422 to place balloon channel 1414 in fluid communication with suction channel 1406 during transition from the second state to the third state. In various embodiments, depressing balloon valve 1422 may align balloon valve radial hole 1454-1 and linkage radial hole 1454-2 to place balloon channel 1414 in fluid communication with suction channel 1406 during transition from the second state to the third state.

FIGS. 15A-15I illustrate various aspects of an exemplary suction valve assembly 1502 in environments 1500A-1500I, according to one or more embodiments described herein. In many embodiments, a cross section of one or more components may be illustrated in environments 1500A-1500I. In some embodiments, one or more components of FIGS. 15A-15I may be the same or similar to one or more other components described herein. For instance, suction valve assembly 1502 may be the same or similar to suction valve assembly 1402. Environments 1500A-1500I may include one or more portions of the suction valve assembly 1502. In one or more embodiments described herein, suction valve assembly may include a linkage 1556-1 to operate in conjunction with a balloon valve 1522 to control flow through a balloon channel 1514. Embodiments are not limited in this context.

Figure 15A:
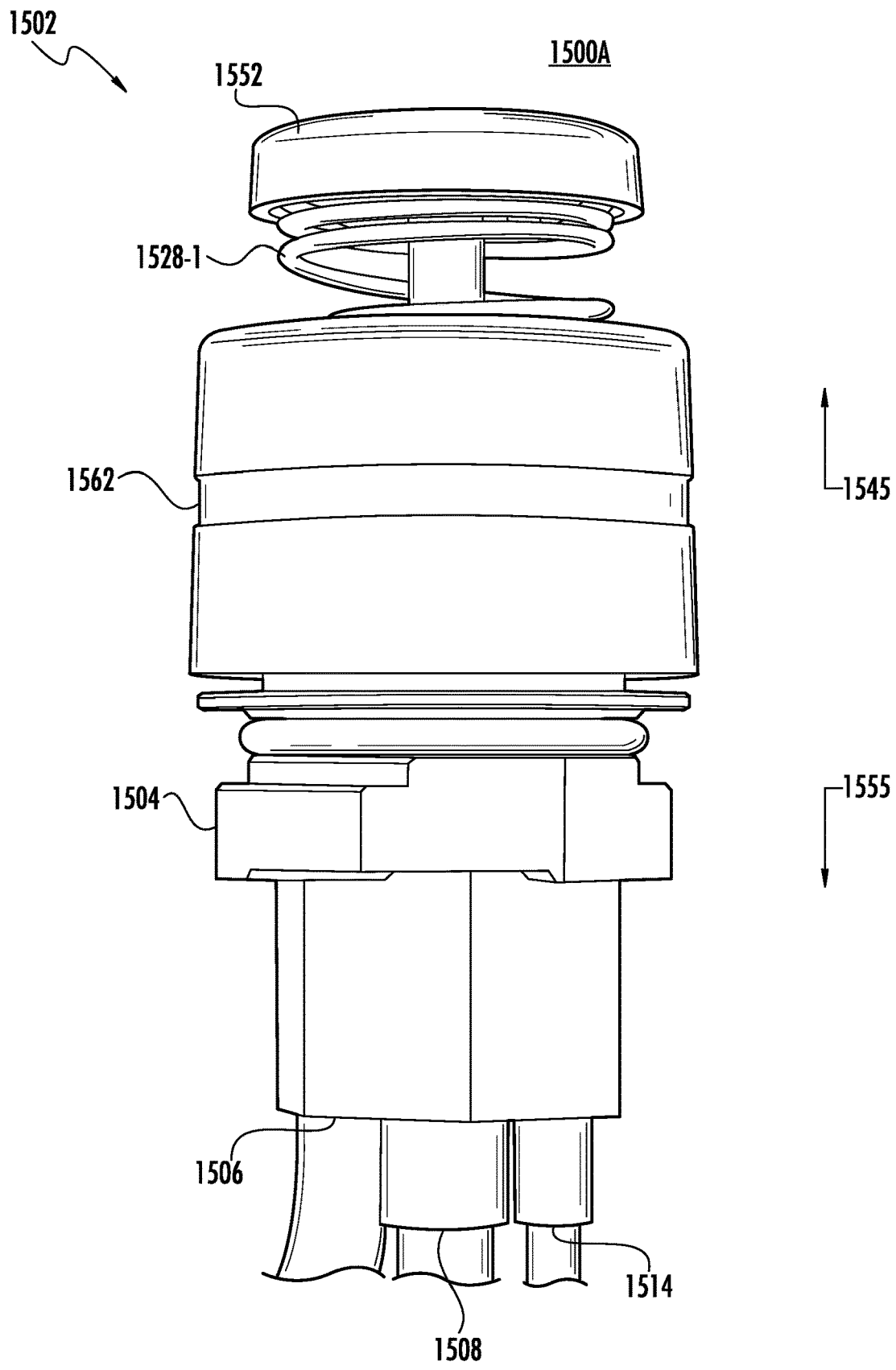
Figure 15B:
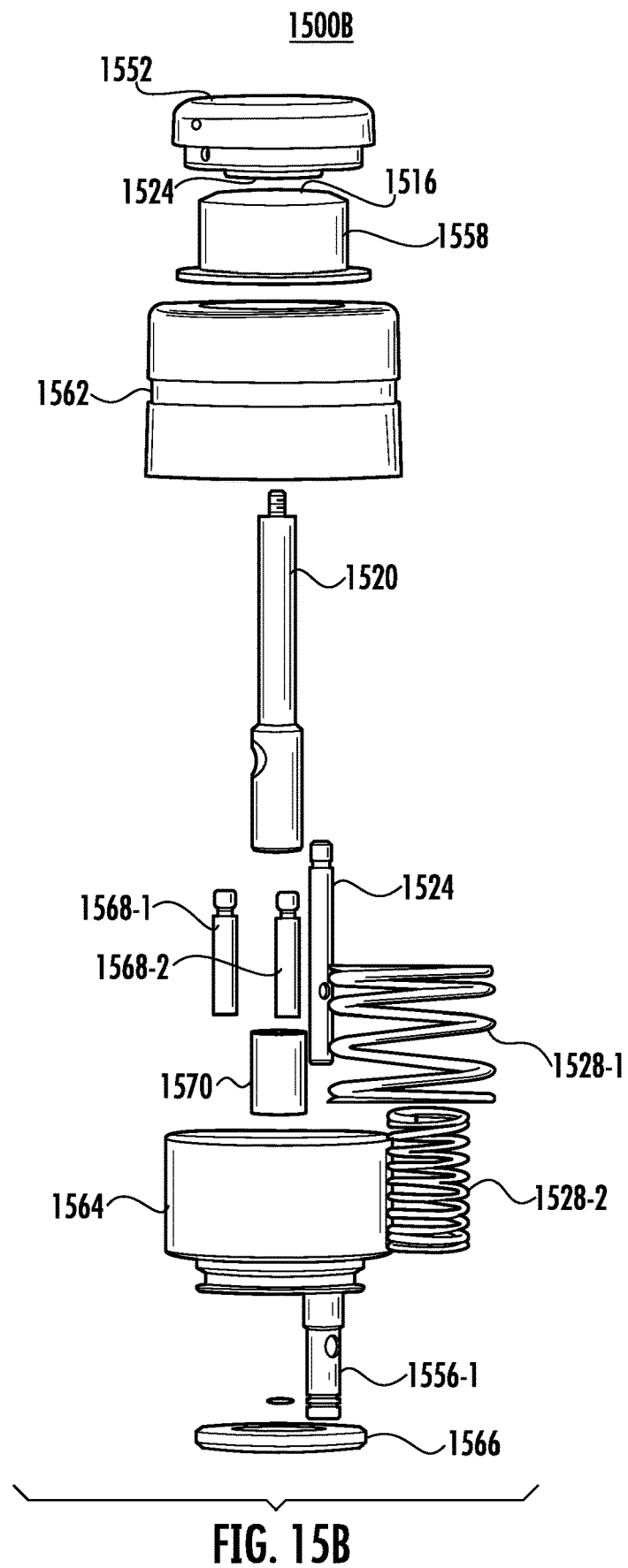

Referring to FIG. 15A, environment 1500A illustrates a perspective view of suction valve assembly 1502. In the illustrated embodiment, suction valve assembly 1502 may include an interface 1552, biasing member 1528-1, housing 1562, and suction valve well 1504 with suction channel 1506, working channel 1508, and balloon channel 1514. Referring to FIG. 15B, environment 1500B illustrates an exploded view of various components of suction valve assembly 1502. The illustrated embodiment may include interface 1552, atmospheric valve 1524, atmospheric channel 1516, hat 1558, housing 1562, working channel valve 1520, pins 1568-1, 1568-2, balloon valve 1522, bowl 1564, collar 1570, biasing members 1528-1, 1528-2, linkage 1556-1, and seal 1566.

Figure 15C:
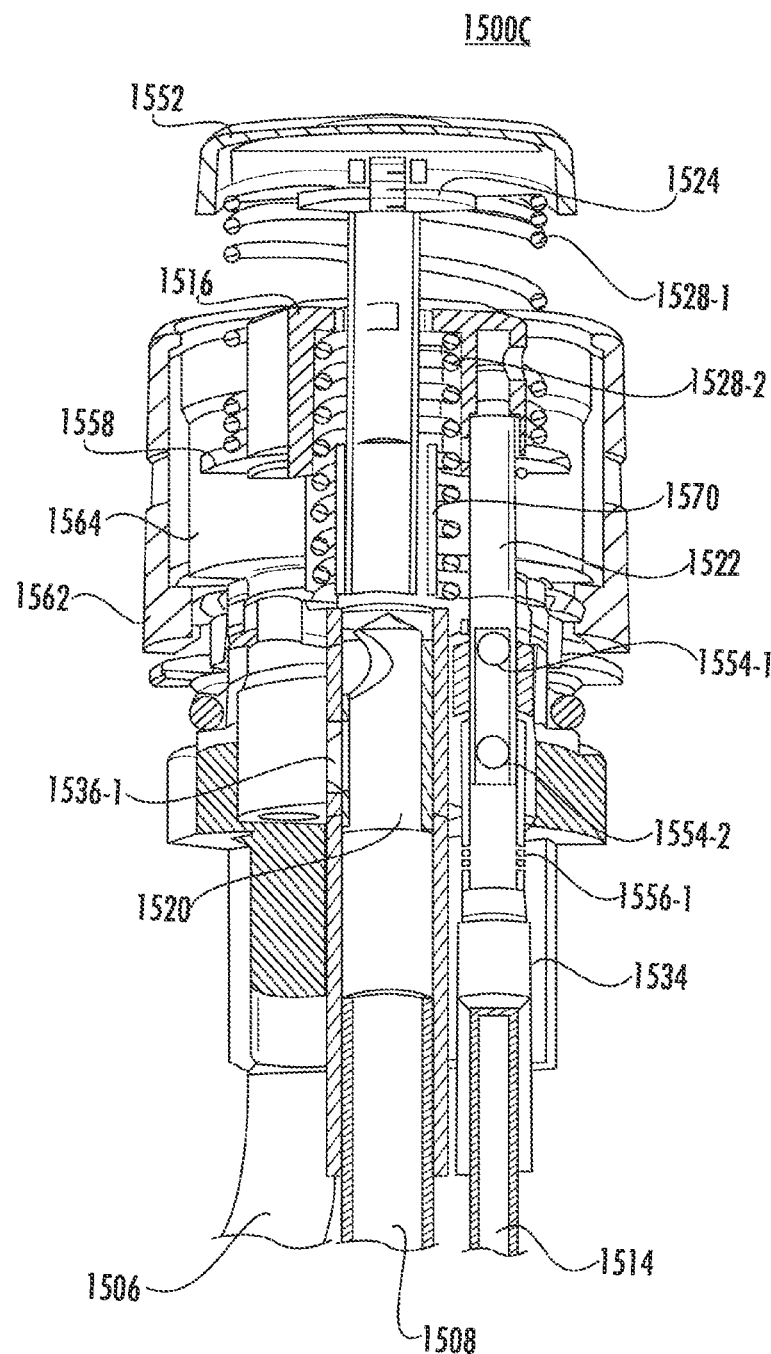

Referring to FIG. 15C, environment 1500C illustrates a cross-sectional view of suction valve assembly 1502. In the illustrated embodiment, suction valve assembly 1502 may include interface 1552, atmospheric valve 1524, atmospheric channel 1516, biasing members 1528-1, 1528-2, housing 1562, hat 1558, bowl 1564, collar 1570, balloon valve 1522 with balloon valve radial hole 1554-1, seal 1566, linkage 1556-1 with linkage radial hole 1554-2, working channel valve 1520, and suction valve well 1504 with suction channel 1506, working channel 1508, and balloon channel 1514 with necking portion 1534.

Referring to FIGS. 15D and 15E, environments 1500D, 1500E may illustrate top and bottom perspective views, respectively, of a portion of the suction valve assembly 1502. Environment 1500D may include atmospheric channel 1516, atmospheric valve 1524, working channel valve 1520, working channel 1508, balloon channel 1514 and linkage 1556-1. Environment 1500E may include seal 1566, working channel 1508, balloon channel 1514 and linkage radial hole 1544-2. In various embodiments, linkage 1556-1 may include at least a portion of the balloon channel 1514. In several embodiments, at least a portion of linkage 1556-1 may be disposed within the balloon channel.

Figure 15G:
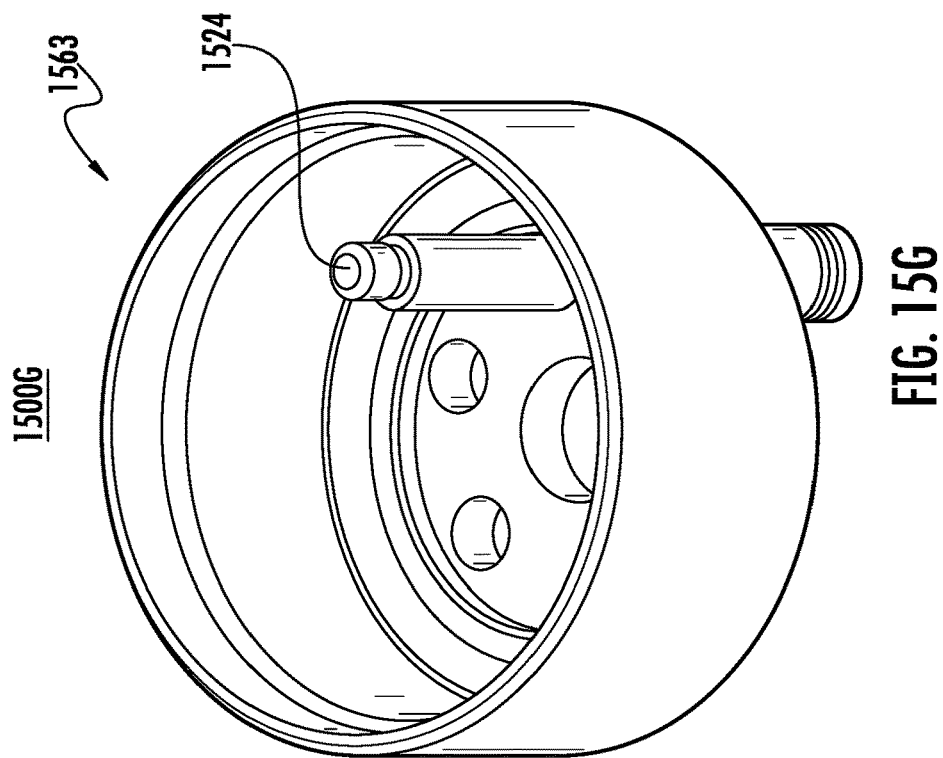
Figure 15F:
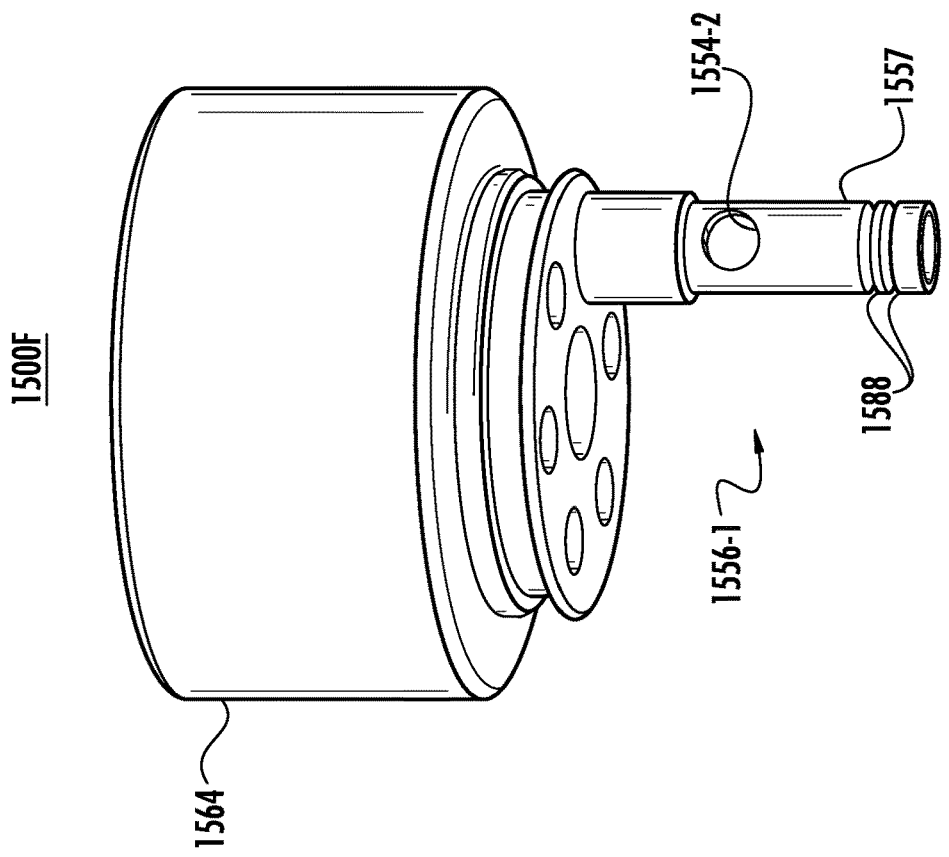

Referring to FIGS. 15F and 15G, environments 1500F, 1500G may illustrate top and bottom perspective views, respectively, of a portion of the suction valve assembly 1502. Environment 1500F includes bowl 1564 and linkage 1556-1 with linkage radial hole 1554-2, tubular structure 1557, and one or more features 1588. In many embodiments, the linkage 1556-1 may extend from the bottom of the bowl 1564. In some embodiments, the one or more features 1588 may facilitate creating a seal between linkage 1556-1 and the suction valve well 1504. For example, features 1558 may include radial slots around tubular structure 1557 for receiving an O-ring. In many embodiments, the balloon valve 1522 may be configured to extend through at least a portion of an interior of the bowl and at least a portion of an interior of the linkage 1556-1.

Referring to FIG. 15H, environment 1500H may illustrate a bottom perspective view of working channel valve 1520 with working channel valve radial hole 1540 in fluid communication with a hole in the bottom of the working channel valve 1520. Referring to FIG. 15I, environment 1500I may illustrate a bottom perspective view of balloon channel valve 1524 with balloon valve radial hole 1554-1.

In various embodiments, when balloon valve radial hole 1554-1 is aligned with the linkage radial hole 1554-2, the balloon channel may be placed in fluid communication with the suction channel. In many embodiments, the valve interface mechanism of valve assembly 1502 may be configured to displace at least a portion of the balloon valve 1522 toward the bottom of the linkage 1556-1 to place the suction channel 1506 in fluid communication with the balloon channel 1514. In some embodiments, the valve interface mechanism may be configured to align the balloon valve radial hole 1554-1 and the linkage radial hole 1554-2 to place the suction channel in fluid communication with the balloon channel. In some such embodiments, the valve interface mechanism may be configured to misalign the balloon valve radial hole 1554-1 and the linkage radial hole 1554-2 to block flow through the balloon channel. In several embodiments, the set of one or more biasing members may be configured to bias the balloon valve radial hole 1554-1 out of alignment with the linkage radial hole 1554-2.

In one or more embodiments, the tubular structure 1557 of the linkage 1556-1 may be nonconcentric with the cylindrical portion 1563 of the bowl 1564. In many embodiments, the balloon valve 1522 may be concentric with the linkage 1556-1 and nonconcentric with the bowl 1564 when extended through at least a portion of the interior of the bowl and at least a portion of the interior of the linkage. In some embodiments, the set of one or more biasing members may be configured to bias the balloon valve to block flow through the balloon channel.

Figure 16:
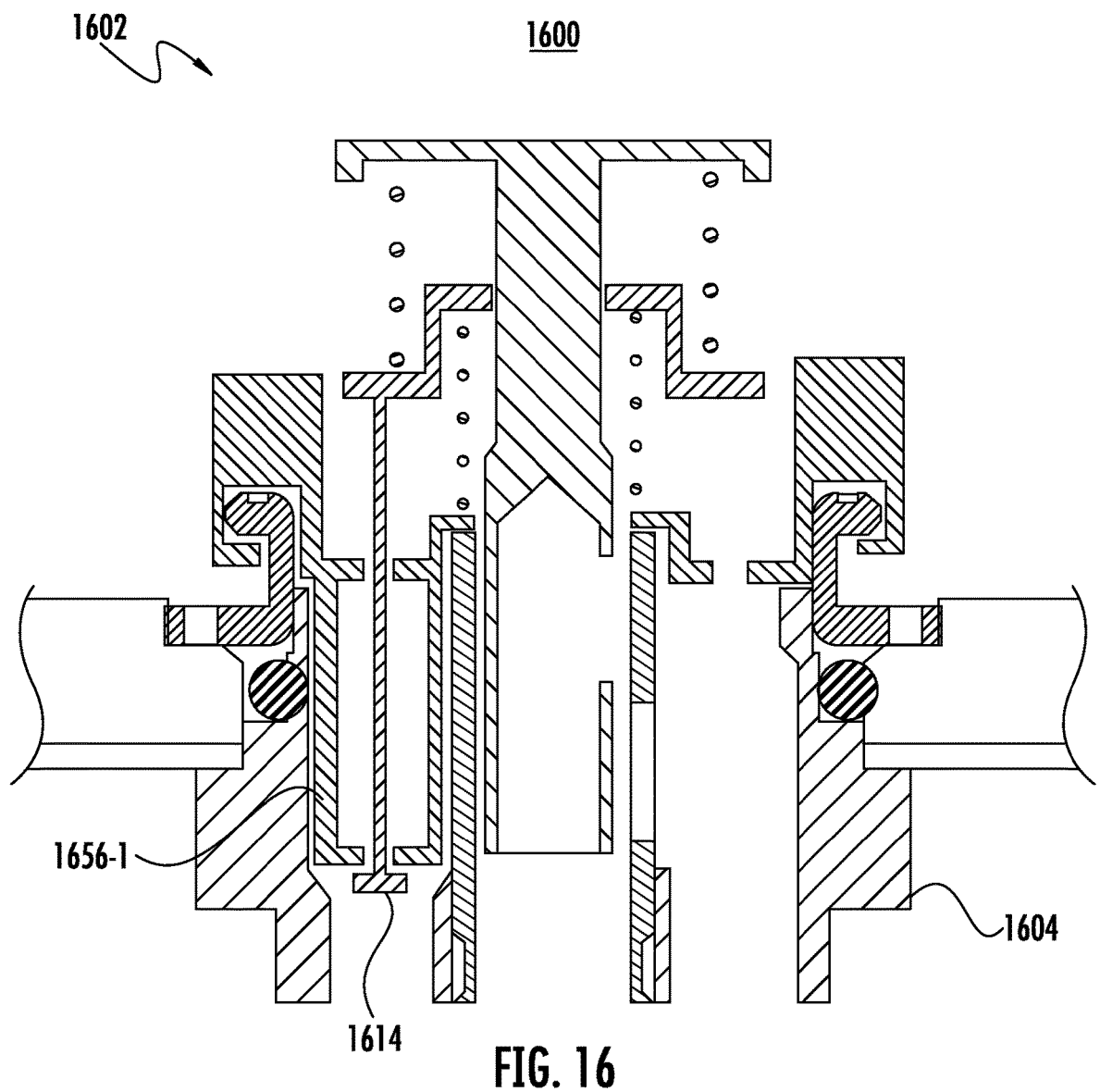
FIG. 16 illustrates various aspects of an exemplary suction valve assembly, according to one or more embodiments described herein.

FIG. 16 illustrates various aspects of an exemplary suction valve assembly 1602 in environment 1600, according to one or more embodiments described herein. In many embodiments, a cross section of one or more components may be illustrated in environment 1600. In some embodiments, one or more components of FIG. 16 may be the same or similar to one or more other components described herein. The suction valve assembly 1602 may include interface 1652, hat 1658, housing 1662, working channel valve 1620, and biasing members 1628-1, 1628-2 (or biasing members 1628). In many embodiments, the suction valve assembly 1602 may be the same or similar to suction valve assemblies 1402, 1502 with the exception of linkage 1656-1 and balloon valve 1614. In one or more embodiments described herein, the linkage 1656-1 and balloon valve 1614 may utilize a plunger seal configuration to control flow through the balloon channel of suction valve well 1604. Embodiments are not limited in this context.

In the atmospheric suction state, flow passes from the atmosphere, through the hat 1658, and out via the suction channel 1606. In various embodiments, biasing members 1628 may bias the suction valve assembly 1602 into the atmospheric suction state in the absence of external forces. To transition into the working channel suction state, biasing member 1628-1 may compress in response to the interface 1652 being depressed a first amount. In the working channel suction state, the bottom side of the interface 1652 may seal against hat 1658 to block off the atmosphere from passing into the suction valve assembly 1602. Additionally, the working channel valve aligns to permit flow between the working channel and the suction channel. To transition into the balloon channel suction state, biasing member 1628-1 may compress in response to the interface 1652 being depressed a first amount. Biasing member 1628-2 may compress while the hat 1658 and the balloon valve 1614 move down in response to interface 1652 being depressed a second amount past the first amount. In the working channel suction state, the bottom side of the interface 1652 may seal against hat 1658 to block off the atmosphere from passing into the suction valve assembly 1602. Additionally, the balloon valve 1614 opens and working channel valve misaligns to block flow between the working channel and the suction channel to permit flow from the balloon channel to the suction channel.

Figure 17A:
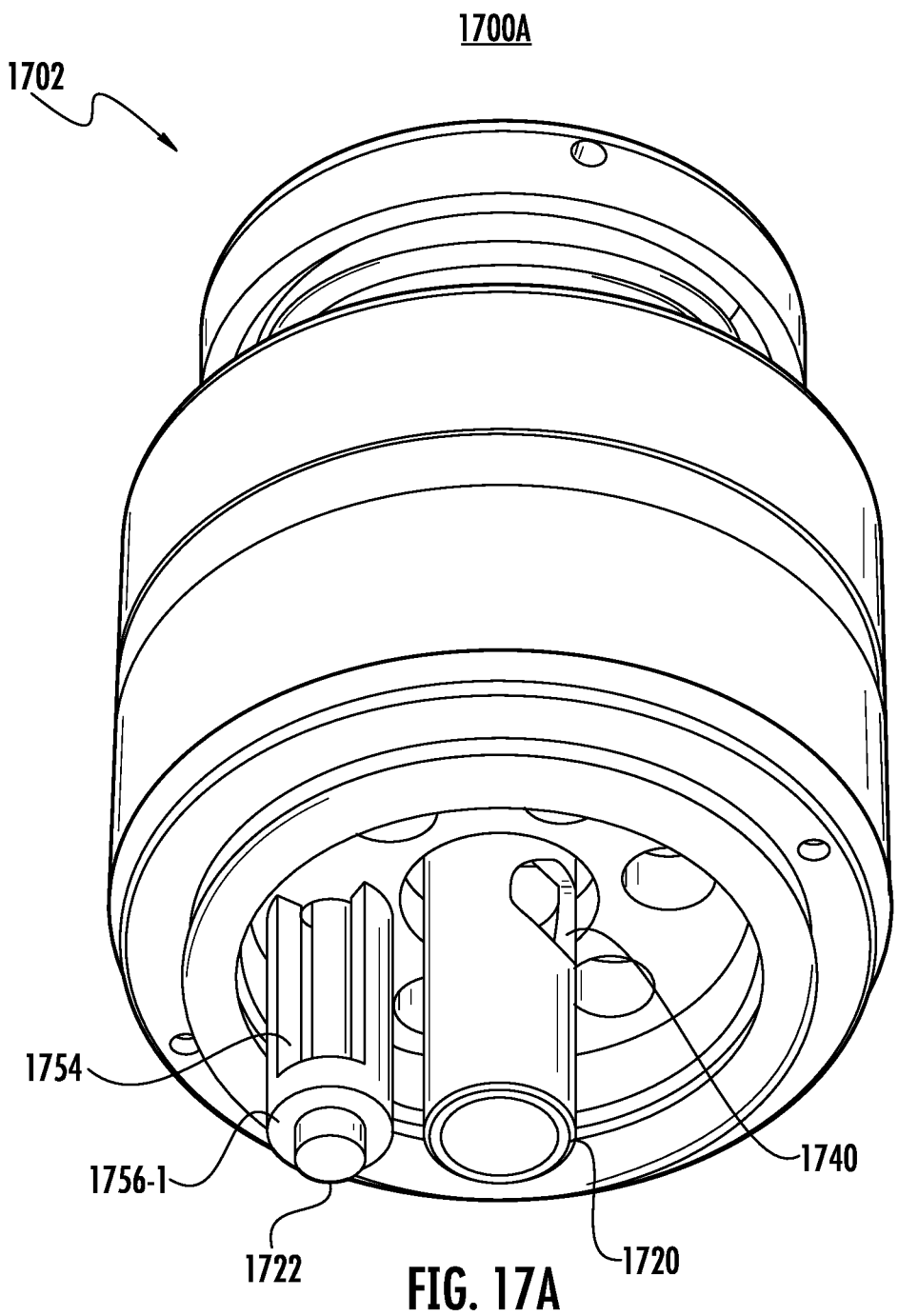
FIGS. 17A-17C illustrate various aspects of an exemplary suction valve assembly, according to one or more embodiments described herein.
Figure 17B:
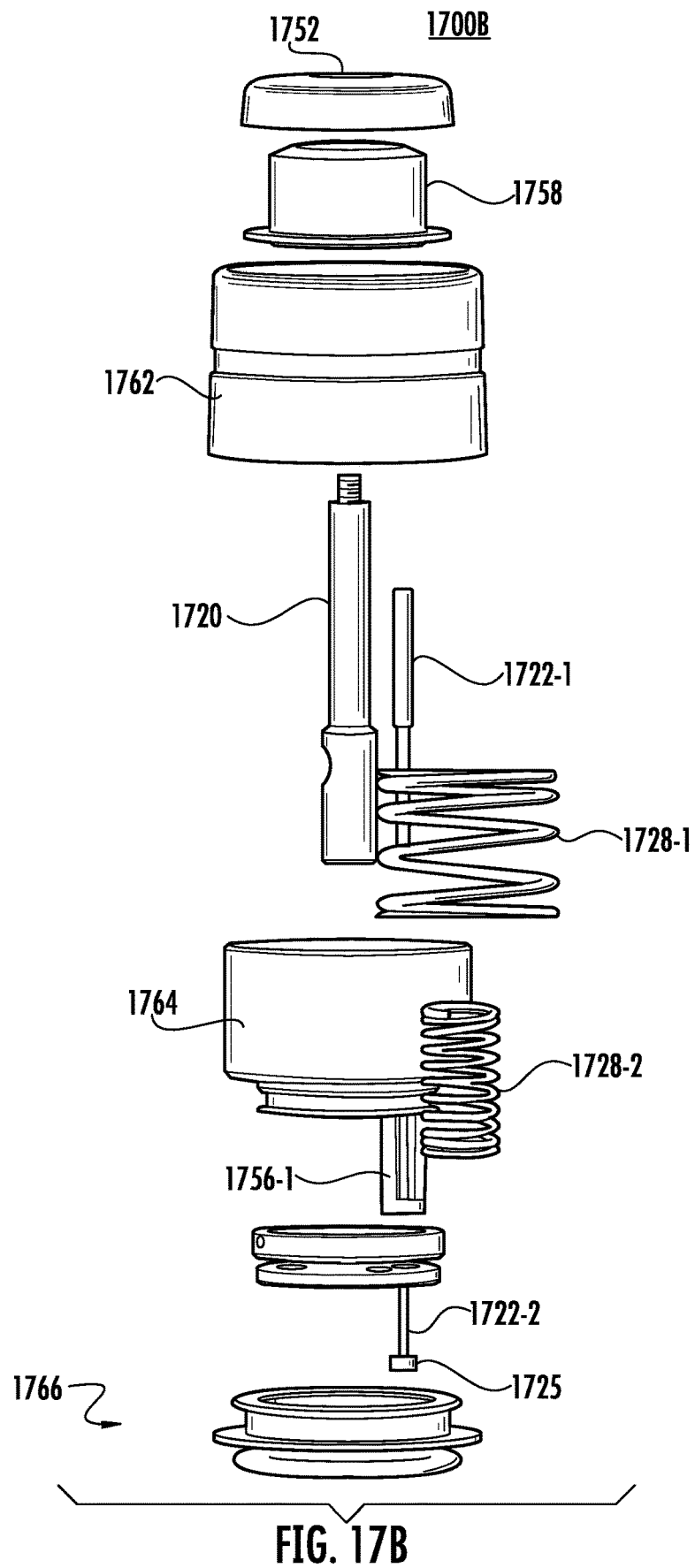
Figure 17C:
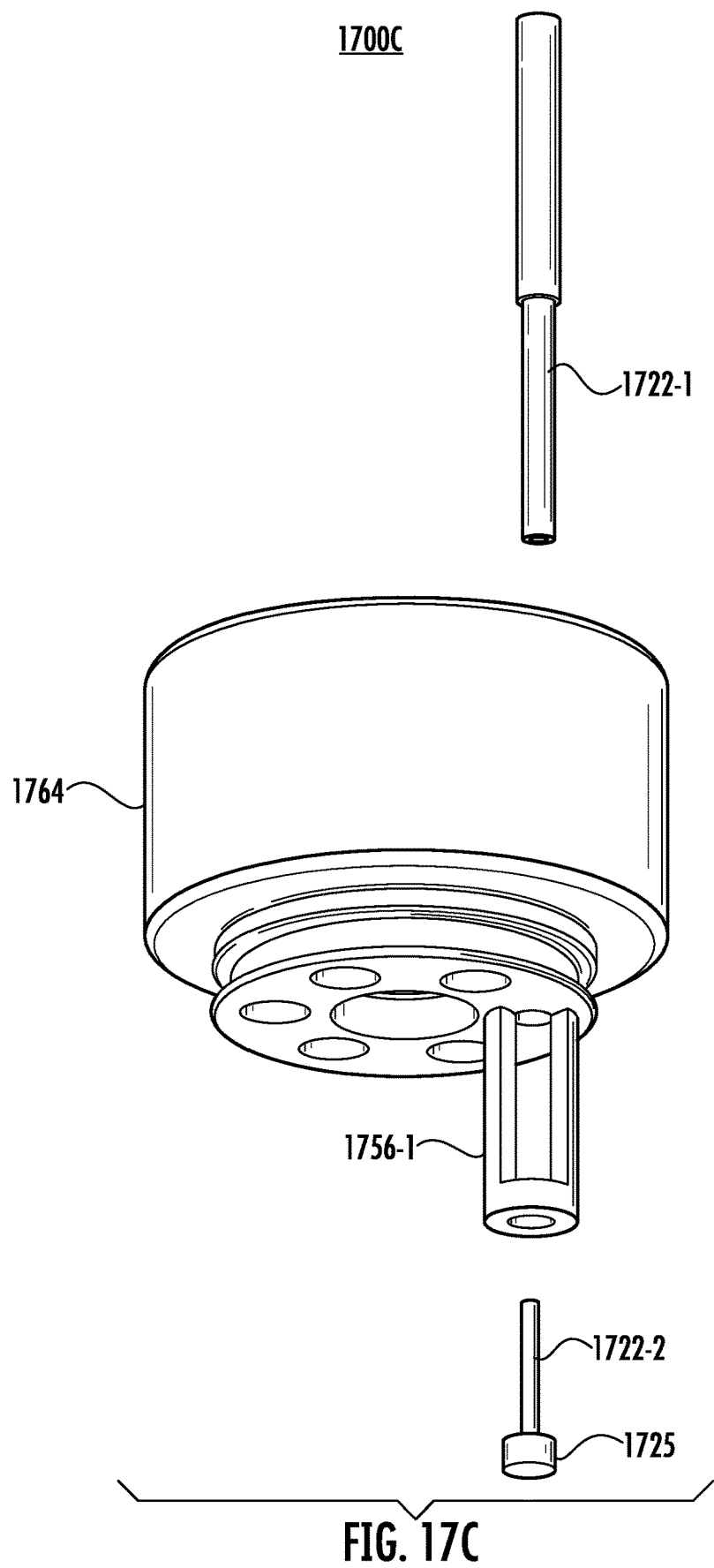

FIGS. 17A-17C illustrate various aspects of an exemplary suction valve assembly 1702 in environments 1700A-1700C, according to one or more embodiments described herein. In many embodiments, a cross section of one or more components may be illustrated in environments 1700A-1700C. In some embodiments, one or more components of FIGS. 17A-17C may be the same or similar to one or more other components described herein. For instance, suction valve assembly 1702 may be the same or similar to suction valve assembly 1602. Environments 1700A-1700C may include one or more portions of the suction valve assembly 1702. In one or more embodiments described herein, suction valve assembly may include a linkage 1756-1 to operate in conjunction with a balloon valve 1722 to control flow through a balloon channel. Embodiments are not limited in this context.

Referring to FIG. 17A, environment 1700A may include a bottom perspective view of suction valve assembly 1702. In the illustrated embodiment, suction valve assembly 1702 may include linkage 1756-1 with linkage radial slot 1754, and working channel valve 1720 with working channel valve radial hole 1740. Referring to FIG. 17B, environment 1700B may include an exploded view of suction valve assembly 1702. In the illustrated embodiments, suction valve assembly 1702 may include interface 1752, hat 1758, housing 1762, bowl 1764, working channel valve 1720, balloon valve 1722 including component 1722-1 and component 1722-2 with plunger 1725, biasing members 1728-1, 1728-2, and seal assembly 1766. In some embodiments, a suction valve well, a suction valve set, and/or a valve interface mechanism may comprise one or more portions of the seal assembly 1766.

Referring to FIG. 17C, environment 1700C may include a bottom perspective view of suction valve assembly 1702. In the illustrated embodiment, suction valve assembly 1702 may include bowl 1764 and balloon valve 1722 with component 1722-1 and component 1722-2 with plunger 1725 (or plunger valve). linkage 1756-1 with linkage radial slot 1754, and working channel valve 1720 with working channel valve radial hole 1740. In various embodiments, the valve interface mechanism may be configured to displace at least a portion of the balloon valve 1722 out of the bottom of the linkage 1756-1 to place the suction channel in fluid communication with the balloon channel. For example, plunger 1725 and a least a portion of balloon valve component 1722-2 may extend out the bottom of linkage 1756. In many embodiments, balloon valve component 1722-1 may include two or more different diameters. In some embodiments, balloon valve component 1722-2 may include two or more different diameters. In one or more embodiments, differing diameters may be utilized to control flow a valve well.

Figure 18:
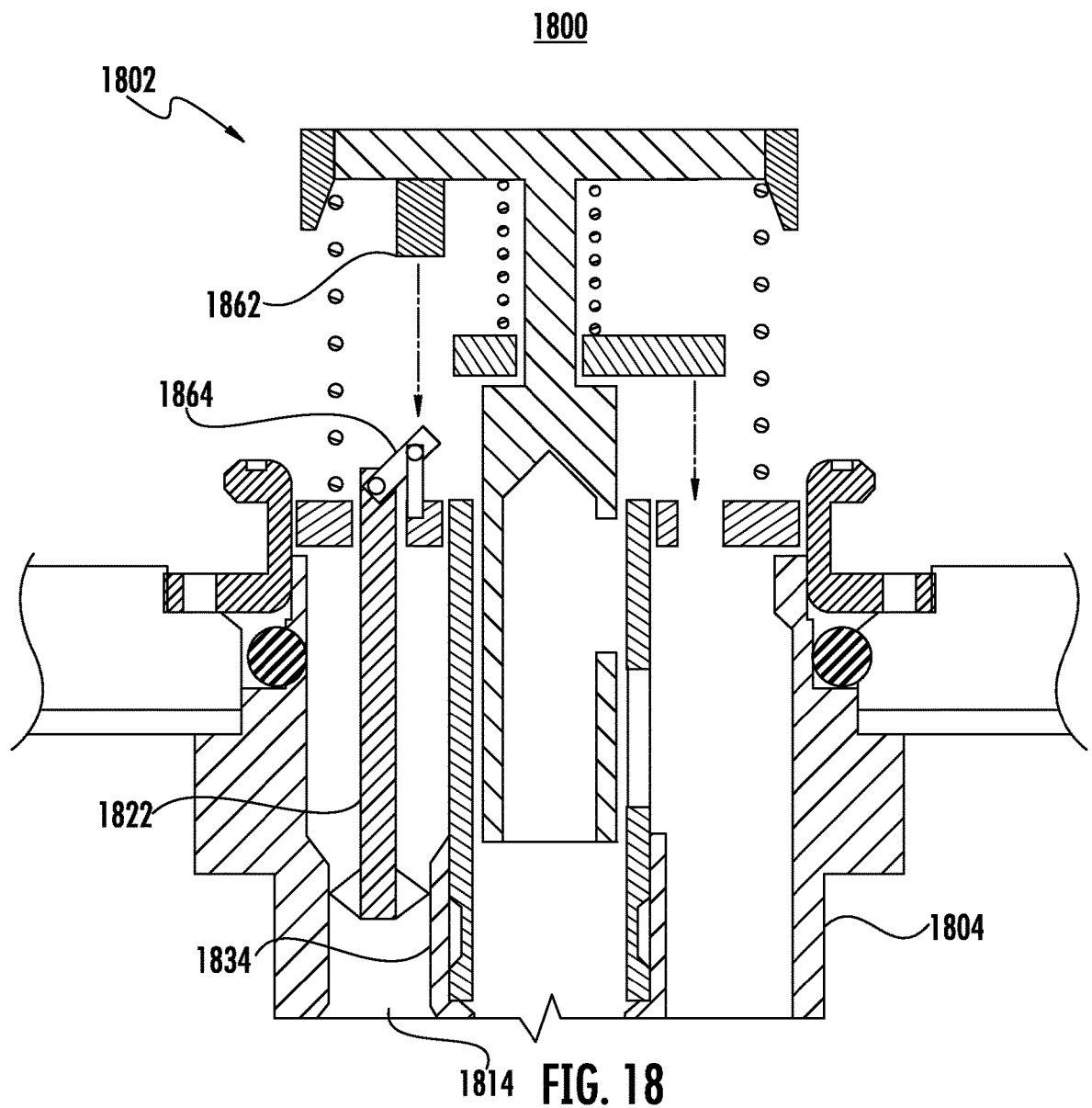
FIG. 18 illustrates various aspects of an exemplary suction valve assembly, according to one or more embodiments described herein.

FIG. 18 illustrates various aspects of an exemplary suction valve assembly 1802 in environment 1800, according to one or more embodiments described herein. In many embodiments, a cross section of one or more components may be illustrated in environment 1800. In some embodiments, one or more components of FIG. 18 may be the same or similar to one or more other components described herein. In many embodiments, the suction valve assembly 1802 may be the same or similar to other suction valve assemblies described herein with the exception of contact member 1862, lever mechanism 1864, and balloon valve 1822. In one or more embodiments described herein, the lever mechanism 1864 may cause the balloon valve 1822 to displace vertically up and out of the necking portion 1834 to enable flow through the balloon channel 1814. In many embodiments, the lever mechanism may be activated to lift the balloon valve out of the necking portion 1834 with contact member 1862. In various embodiments, the contact member 1862 and the lever mechanism may be coupled to/comprised in one or more portions of the valve interface mechanism, such as a linkage, an interface member, a hat, a bowl, a housing, and the like. Embodiments are not limited in this context.

Similar to other embodiments, in the first state, the suction channel may pull from the atmosphere (i.e., atmospheric channel in fluid communication with suction channel). Transitioning to the second state moves the working channel valve down and seals the suction channel from the atmosphere to place the working channel and the suction channel in fluid communication. Transitioning to the third state causes the contact member 1862 to activate the lever mechanism 1864 and move at least a portion of the balloon valve 1822 out of the necking portion 1834 to place the suction channel in fluid communication with balloon channel.

Figure 19:
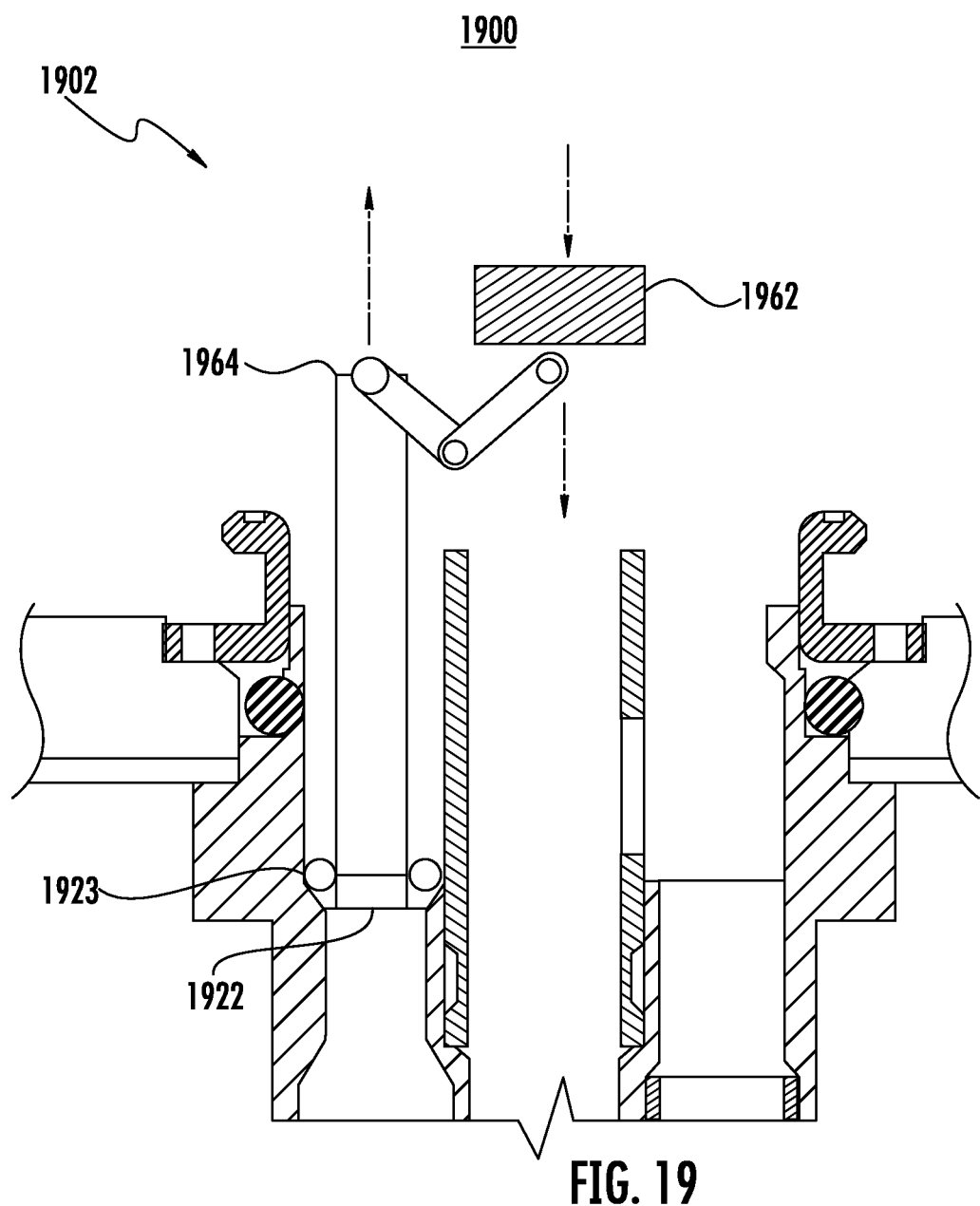
FIG. 19 illustrates various aspects of an exemplary suction valve assembly, according to one or more embodiments described herein.

FIG. 19 illustrates various aspects of an exemplary suction valve assembly 1902 in environment 1900, according to one or more embodiments described herein. In many embodiments, a cross section of one or more components may be illustrated in environment 1900. In some embodiments, one or more components of FIG. 19 may be the same or similar to one or more other components described herein. In many embodiments, the suction valve assembly 1902 may be the same or similar to other suction valve assemblies described herein with the exception of receiving seal 1923, lever mechanism 1964 and balloon valve 1922. As previously mentioned, not all components needed for operation may be illustrated (e.g., in FIG. 19) to focus on specific aspects (e.g., lever mechanism 1964) of an embodiment. However, components illustrated and/or described herein may be incorporated into and/or combined with any other components or embodiments without departing from the scope of this disclosure. Embodiments are not limited in this context.

In one or more embodiments described herein, lever mechanism 1964 may displace the balloon valve vertically downward into the receiving seal 1923 to block flow through the balloon channel, and displace the balloon valve vertically upward and out of the receiving seal 1923 to permit flow through the balloon channel. In one or more such embodiments, balloon valve may stop short of entering the necking portion when blocking flow through the balloon channel. In several embodiments, the lever mechanism 1964 may comprise a plurality of links connected to one or more portions of the suction valve assembly 1902, such as a linkage, an interface member, a hat, a bowl, a housing, and the like. In many embodiments, the lever mechanism 1964 may be configured to provide mechanical linkage between the balloon valve 1922 and one or more other components of the suction valve assembly 1902, such as an interface member.

Figure 20:
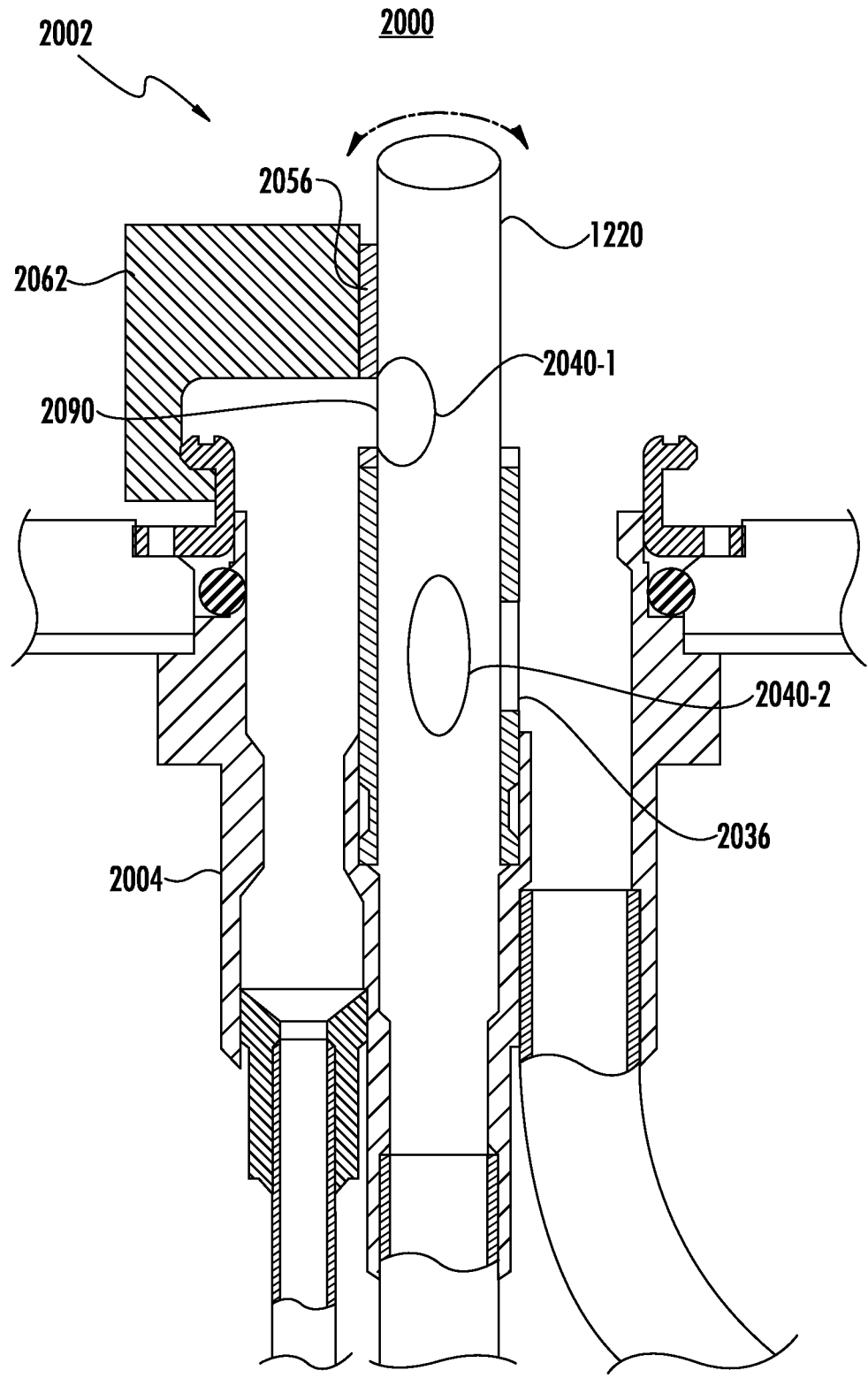
FIG. 20 illustrates various aspects of an exemplary suction valve assembly, according to one or more embodiments described herein.

FIG. 20 illustrates various aspects of an exemplary suction valve assembly 2002 in environment 2000, according to one or more embodiments described herein. In many embodiments, a cross section of one or more components may be illustrated in environment 2000. In some embodiments, one or more components of FIG. 20 may be the same or similar to one or more other components described herein. In many embodiments, the suction valve assembly 2002 may be the same or similar to other suction valve assemblies described herein, such as suction valve assembly 1300. In many embodiments, the working channel valve 1220 may include/replace the balloon valve. In many such embodiments, a seal may be created between the housing 2062, linkage 2056, and working channel valve 2020. As previously mentioned, not all components needed for operation may be illustrated (e.g., in FIG. 19) to focus on specific aspects (e.g., lever mechanism 1964) of an embodiment. However, components illustrated and/or described herein may be incorporated into and/or combined with any other components or embodiments without departing from the scope of this disclosure. Embodiments are not limited in this context.

In suction valve assembly 2002, working channel valve 2020 may have a plurality of radial holes (e.g., ports) connected by one or more internal channels. In many embodiments, the plurality of ports may be configured to transition the suction valve assembly 2002 between the atmospheric, working channel, and balloon channel suction states in response to rotational and/or vertical movements. In several embodiments, the working channel valve 2020 may make a first rotational movement to align the working channel valve radial hole 2040-2 with well radial hole 2036 to place the working channel 2008 in fluid communication with the suction channel 2006 and a second rotational movement to align the working channel valve radial hole 2040-1 with well radial hole 2090 to place the balloon channel 2014 in fluid communication with the suction channel 2006.

FIGS. 21A-21I illustrate various aspects of an exemplary suction valve assembly 2102 in environments 2100A-2100I, according to one or more embodiments described herein. In many embodiments, a cross section of one or more components may be illustrated in environments 2100A-2100I. In some embodiments, one or more components of FIGS. 21A-21I may be the same or similar to one or more other components described herein. Environments 2100A-2100I may include one or more portions of the suction valve assembly 2102. In one or more embodiments described herein, suction valve assembly 2102 may include a valve interface mechanism comprising a spiral pin 2212 configured to convert vertical displacement into a combination of rotational and vertical displacement. In one or more such embodiments, the combination of rotation and vertical displacement may be utilized to control flow through the suction valve body with suction channel 2106, working channel 2108, and balloon channel 2114. Embodiments are not limited in this context.

Figure 21A:
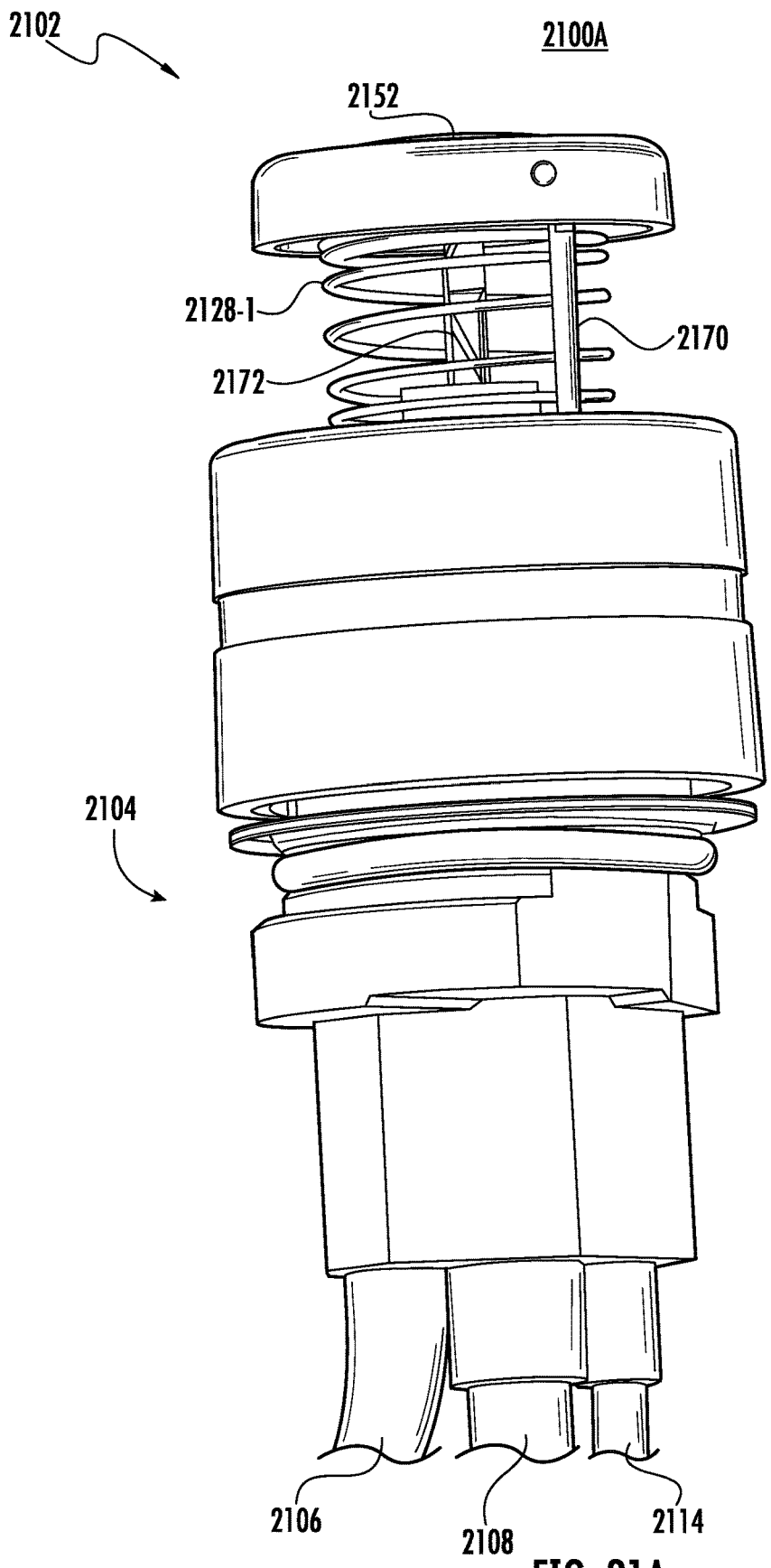
FIGS. 21A-21I illustrate various aspects of an exemplary suction valve assembly, according to one or more embodiments described herein.
Figure 21B:
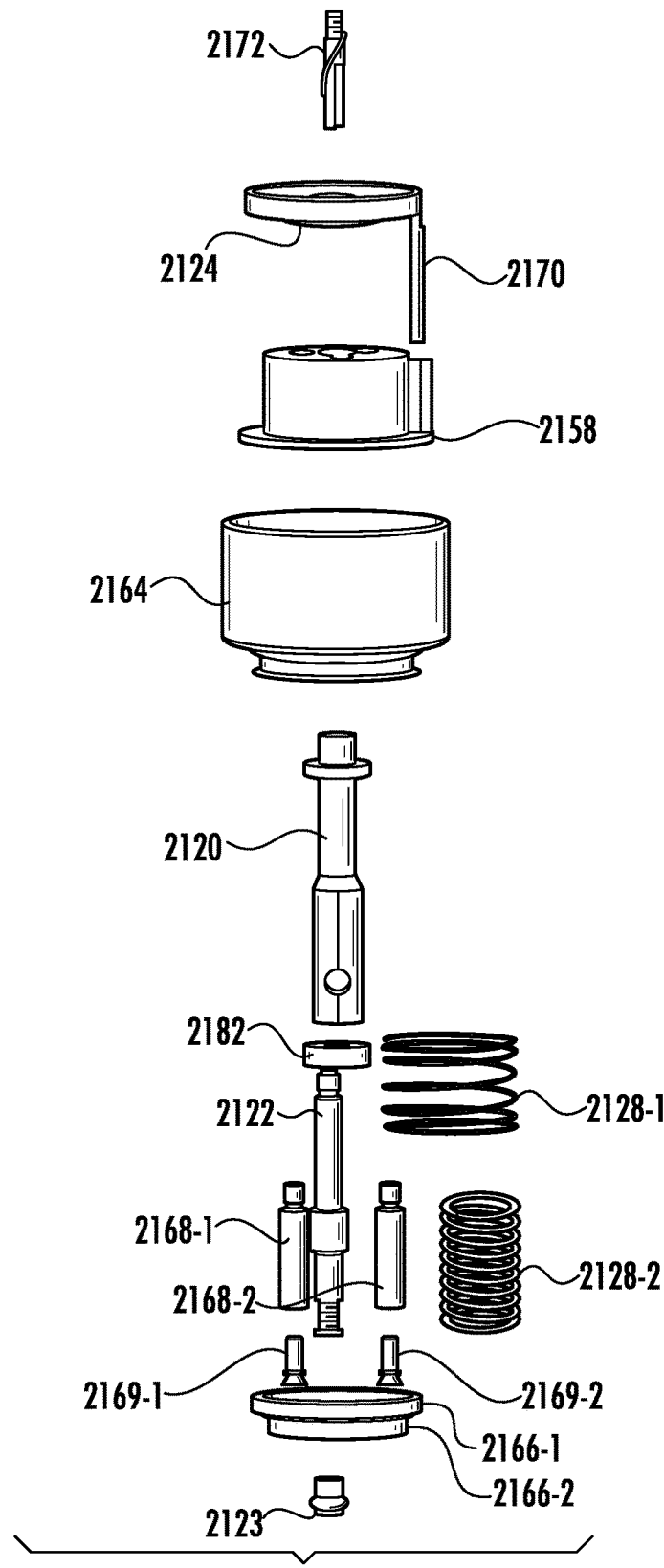

Referring to FIG. 21A, environment 2100A illustrates a perspective view of suction valve assembly 2102. In the illustrated embodiment, suction valve assembly 2102 may include an interface 2152, a spiral pin 2172, push rod 2170, biasing member 2128-1, housing, and suction valve well 2104 with suction channel 2106, working channel 2108, and balloon channel 2114. Referring to FIG. 21B, environment 2100B illustrates an exploded view of various components of suction valve assembly 2102. The illustrated embodiment may include spiral pin 2172, atmospheric valve 2124, hat 2158, working channel valve 2120, pins 2168-1, 2168-2, pin seals 2169-1, 2169-2, spiral guide 2182, balloon valve 2122, bowl 2164, biasing members 2128-1, 2128-2, balloon valve seal 2123, well seal 2166 and alignment feature 2167.

In many embodiments, push rod 2170 may comprise one or more alignment features. For example, the start of the helix may be positioned such that the radial hole of the working channel valve is properly positioned when inserted into the suction valve well 2104. In several embodiments, the spiral feature may be oriented relative to the position of the push rod 2170, and the balloon valve 2122 may be oriented relative to the hat 2158. In several such embodiments, the push rod 2170 may link the balloon valve 2122 and the hat 2158. This may cause the spiral pin 2172 to be oriented relative to the balloon channel 2114, and therefore the radial hole in the suction valve well 2104. As shown in the illustrated embodiment, push rod 2170 may align with complimentary features in different components of the suction valve assembly 2102. For instance, push rod 2170 may be received by a recess in hat 2158.

Figure 21C:
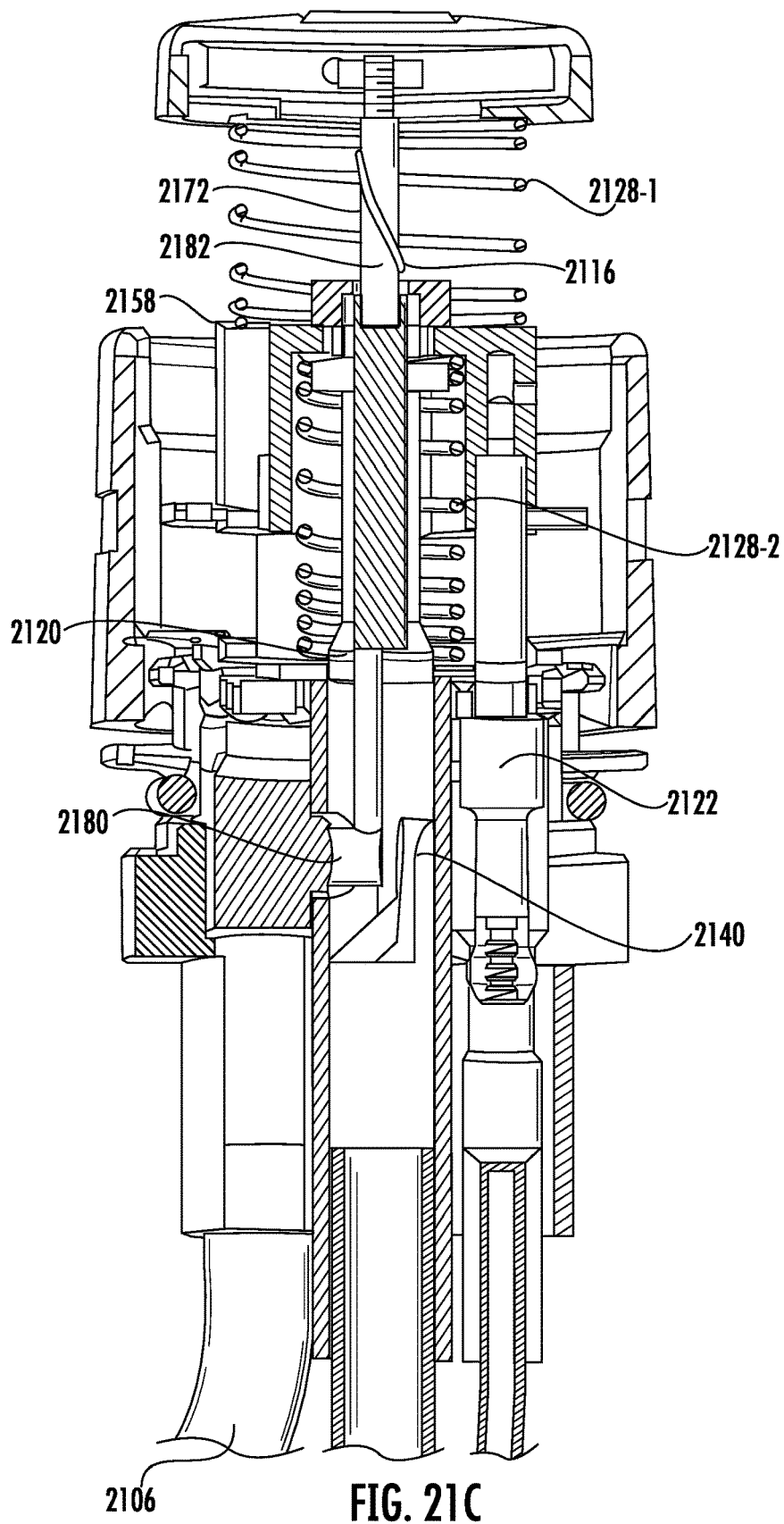

Referring to FIG. 21C, environment 2100C illustrates a cross-sectional view of suction valve assembly 2102. In the illustrated embodiment, suction valve assembly 2102 may include the interface, atmospheric valve, spiral pin 2172, spiral guide 2182, hat 2158, working channel valve 2120 with atmospheric access port 2180 and working channel access port 2140, atmospheric channel 2116, biasing members 2128-1, 2128-2, hat 2158, housing, balloon valve 2124 with balloon valve seal 2123, and suction valve well 2104 with suction channel 2106, working channel, and balloon channel with necking portion.

Figure 21E:
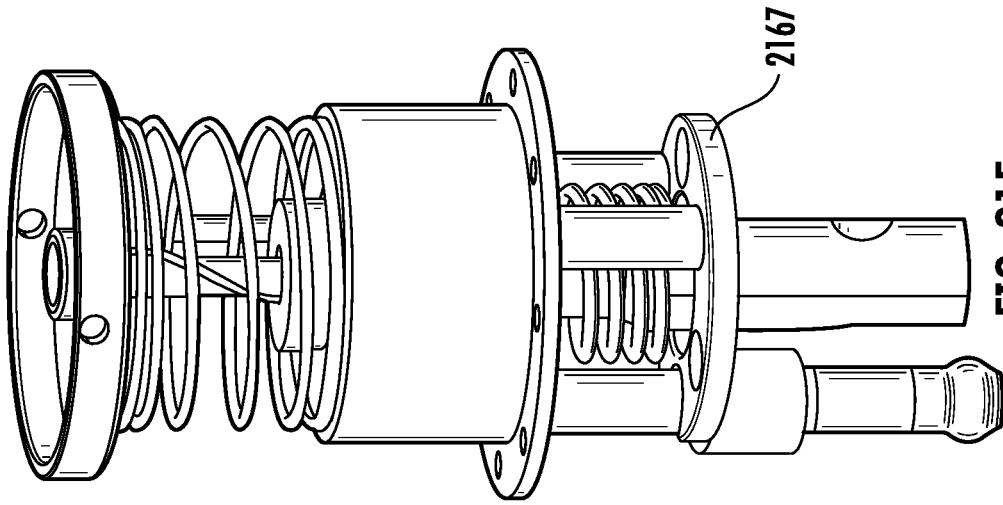
Figure 21D:
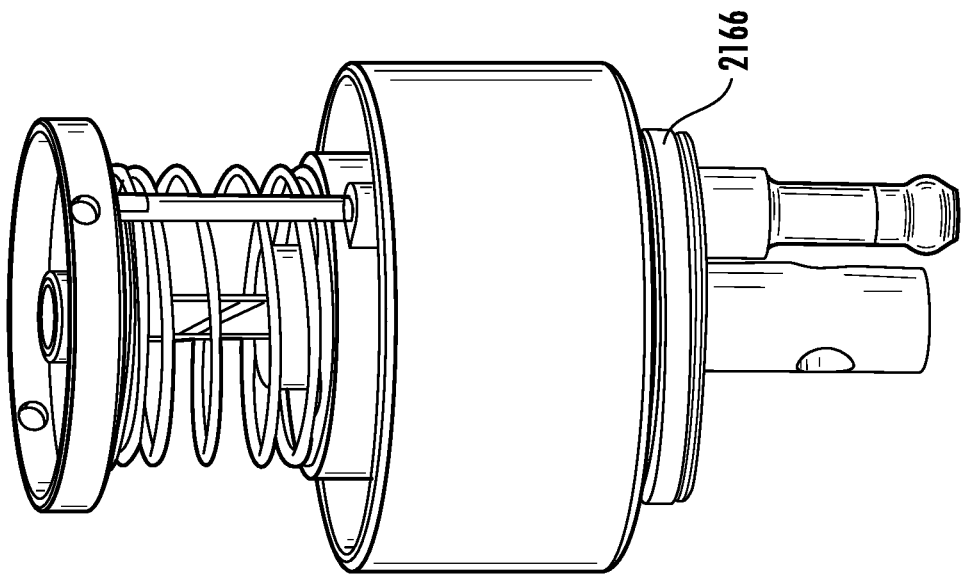
Figure 21F:
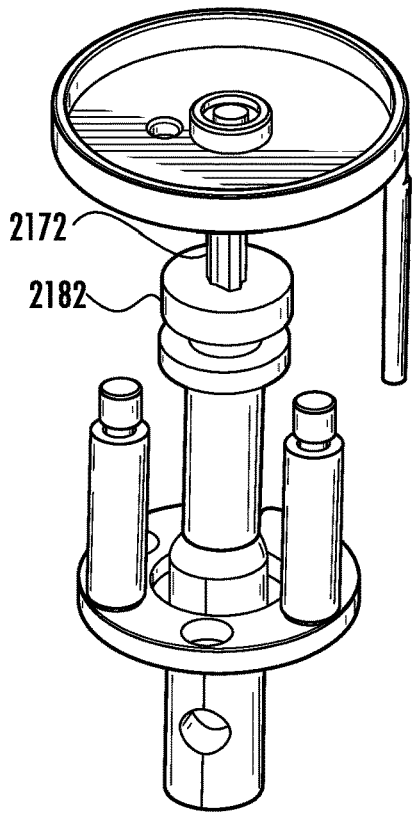

Referring to FIGS. 21D-21F, environments 2100D, 2100E, 2100F may illustrate perspective views of different assembly stages of the suction valve assembly 2102. Environment 2100D illustrates well seal 2166. In some embodiments, well seal 2166 may be included in the valve set and/or valve interface mechanism of suction valve assembly 2102 and utilized to create a seal with the suction valve well 2104. Environments 2100E, 2100F illustrate alignment feature 2167 of suction valve assembly 2102.

Figure 21G:
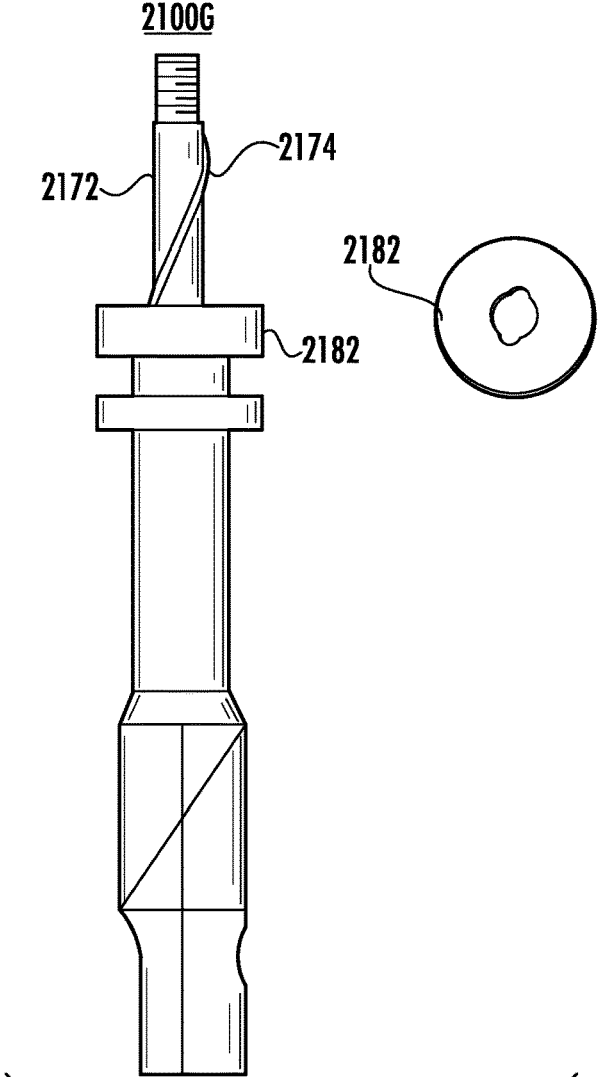
Figure 21H:
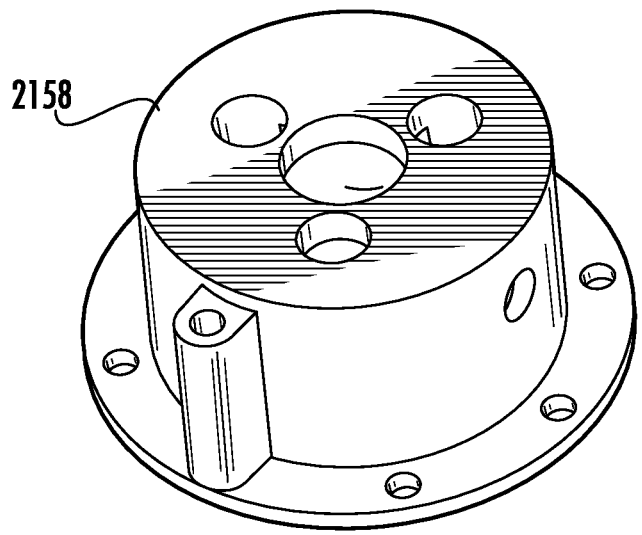
Figure 21I:
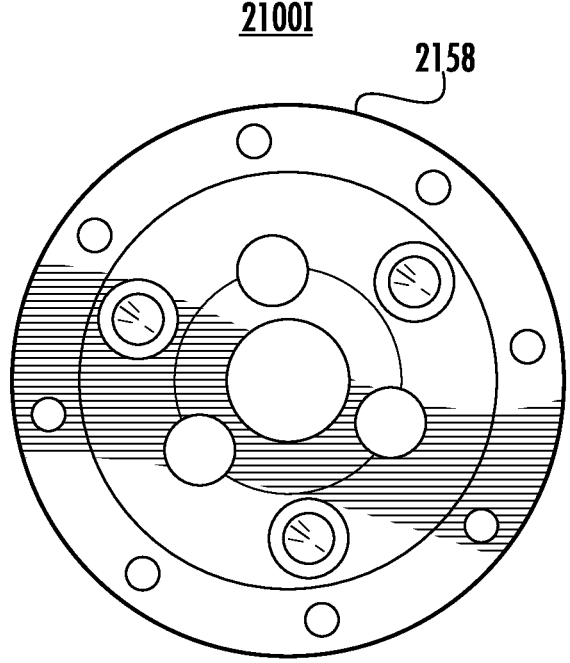

Referring to FIG. 21G, environment 2100G may include the spiral pin 2172 in conjunction with the working channel valve. In many embodiments, the working channel valve may include or couple to spiral guide 2182. In many such embodiments, the spiral 2174 may cause rotational displacement in the working channel valve with the spiral pin 2172 is moved vertically through the spiral guide 2182. Referring to FIG. 21H, environment 2100H may illustrate a perspective view of hat 2158. Referring to FIG. 21I, environment 2100I may illustrate a perspective view of hat 2158. As shown in the illustrated embodiment, hat 2158 may include a plurality of holes and/or recesses. In many embodiments, the holes/recesses may be disposed in concentric rings. In some embodiments, hat 2158 may include radial holes. In several embodiments, the holes/recesses may have different diameters.

FIGS. 22A-22H illustrate various aspects of an exemplary suction valve assembly 2202 in environments 2200A-2200H, according to one or more embodiments described herein. In many embodiments, a cross section of one or more components may be illustrated in environments 2200A-2200H. In some embodiments, one or more components of FIGS. 22A-22H may be the same or similar to one or more other components described herein. For instance, suction valve assembly 2202 may be the same or similar to suction valve assembly 1502 and/or suction valve assembly 2102. Environments 2200A-2200H may include one or more portions of the suction valve assembly 2202. In one or more embodiments described herein, suction valve assembly 2202 may include a set of components to control fluid flow (e.g., suction flow) through a suction valve well when assembled into the valve well. In one or more such embodiments, utilization of the set of components may provide reliable, intuitive, and ergonomic control of fluid through a suction valve well (e.g., suction valve well 1504). Additionally, or alternatively, utilization of suction valve assembly, or one or more components thereof, to control fluid flow through the valve well may simplify manufacturing and/or assembly. Embodiments are not limited in this context.

Figure 22A:
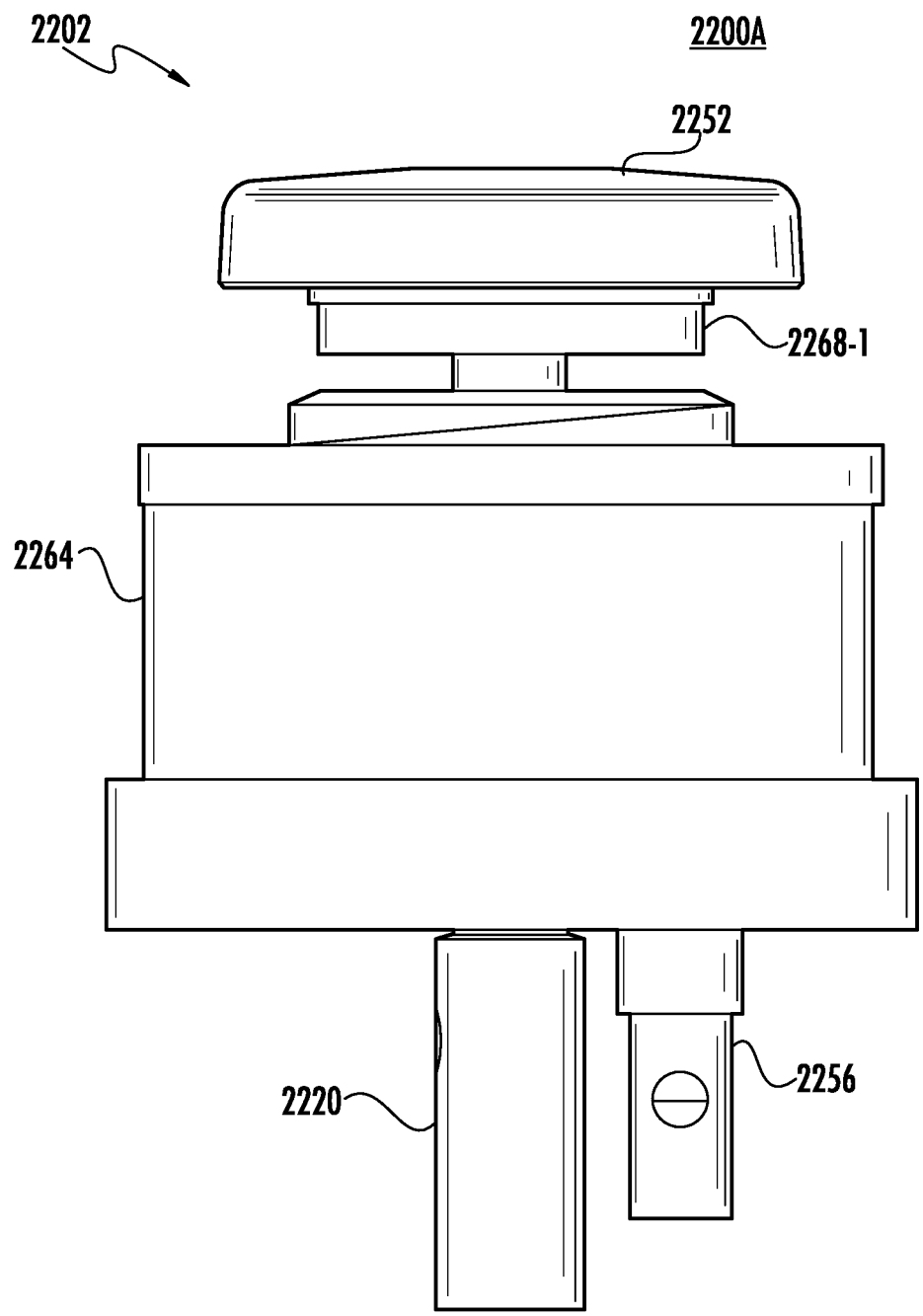
FIGS. 22A-22H illustrate various aspects of an exemplary suction valve assembly, according to one or more embodiments described herein.

Referring to FIG. 22A, environment 2200A illustrates a front view of suction valve assembly 2202. In the illustrated embodiment, suction valve assembly 2202 may include an interface member 2252, seal 2268-1, bowl 2264, working channel valve 2220, and linkage 2256. In various embodiments, the suction valve assembly 2202 may be inserted into a suction valve well (e.g., suction valve well 1504). In various such embodiments, the working channel valve 2220 may extend into the working channel of the suction valve well and/or the linkage 2256 may extend into the balloon channel of the suction valve well when the suction valve assembly 2202 is inserted into the suction valve well. In many embodiments, the suction valve assembly 2202 may be operated via interface member 2252 to control fluid flow through the suction valve well. Operation of the suction valve assembly 2202 via interface member 2252 may move the working channel valve 2220 up and/or down to control fluid flow through the suction valve well. In many embodiments, the suction valve assembly 2202 may include the suction valve well. In some embodiments, bowl 2264 may comprise a housing for one or more components of the suction valve assembly 2202. As will be discussed in more detail below, in many embodiments, the bowl 2264 may include one or more features to align and/or attach the suction valve assembly to a suction valve well.

Figure 22B:
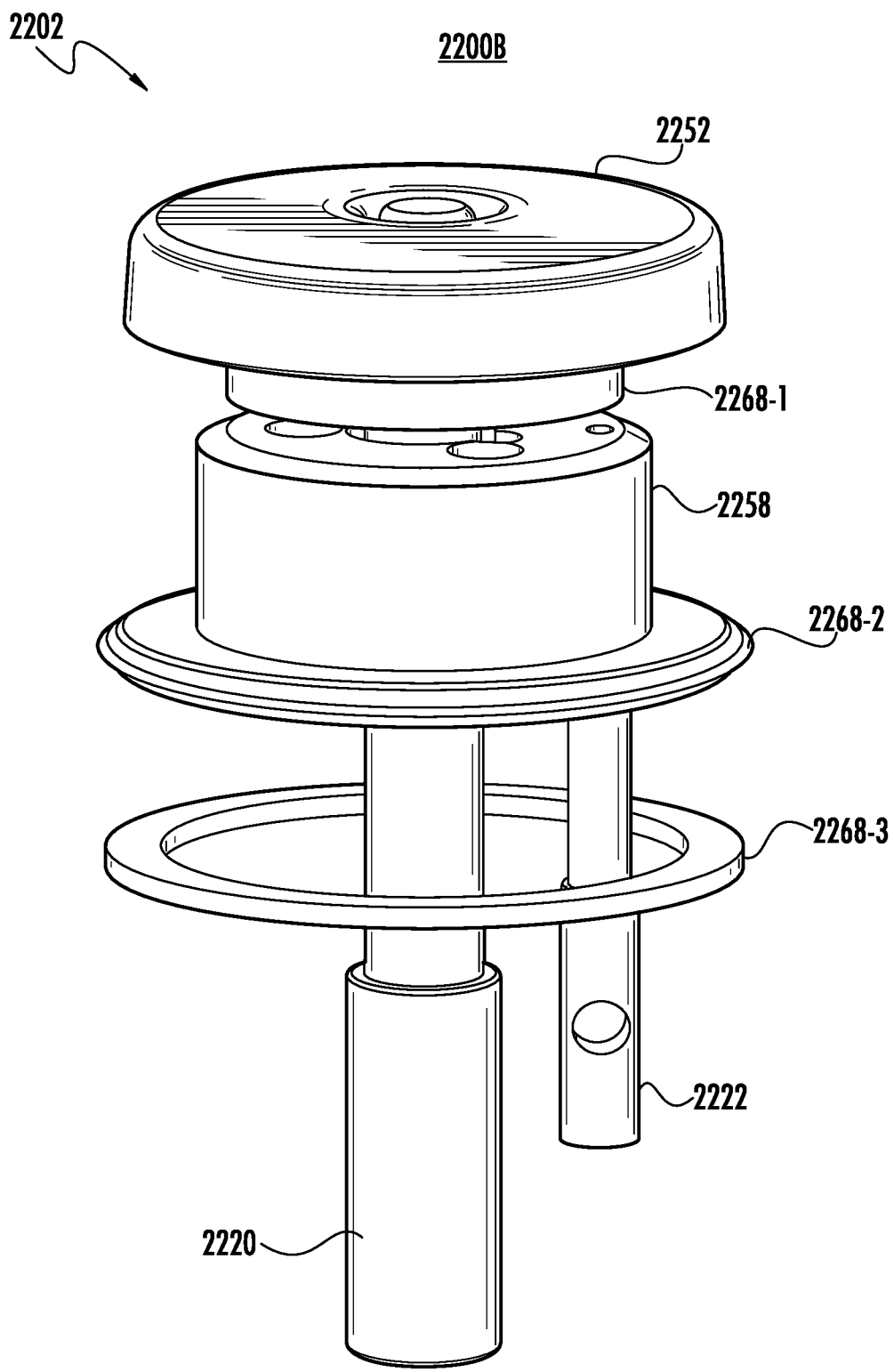

Referring to FIG. 22B, environment 2200B illustrates an assembly stage of the suction valve assembly 2202. The illustrated embodiment may include interface member 2252, seal 2268-1, hat 2258, seal 2268-2, seal 2268-3, working channel valve 2220, and balloon valve 2222. One or more of the interface member 2252, hat 2258, seal 2268-1, seal 2268-2, seal 2268-3, and working channel valve 2220 may be axially aligned and the balloon valve 2222 may be parallel to the axis of alignment for the other components. In one or more embodiments, the balloon valve 2222 may be disposed in the linkage 2256. These and other aspects of suction valve assembly 2202 will be described in more detail below.

Figure 22C:
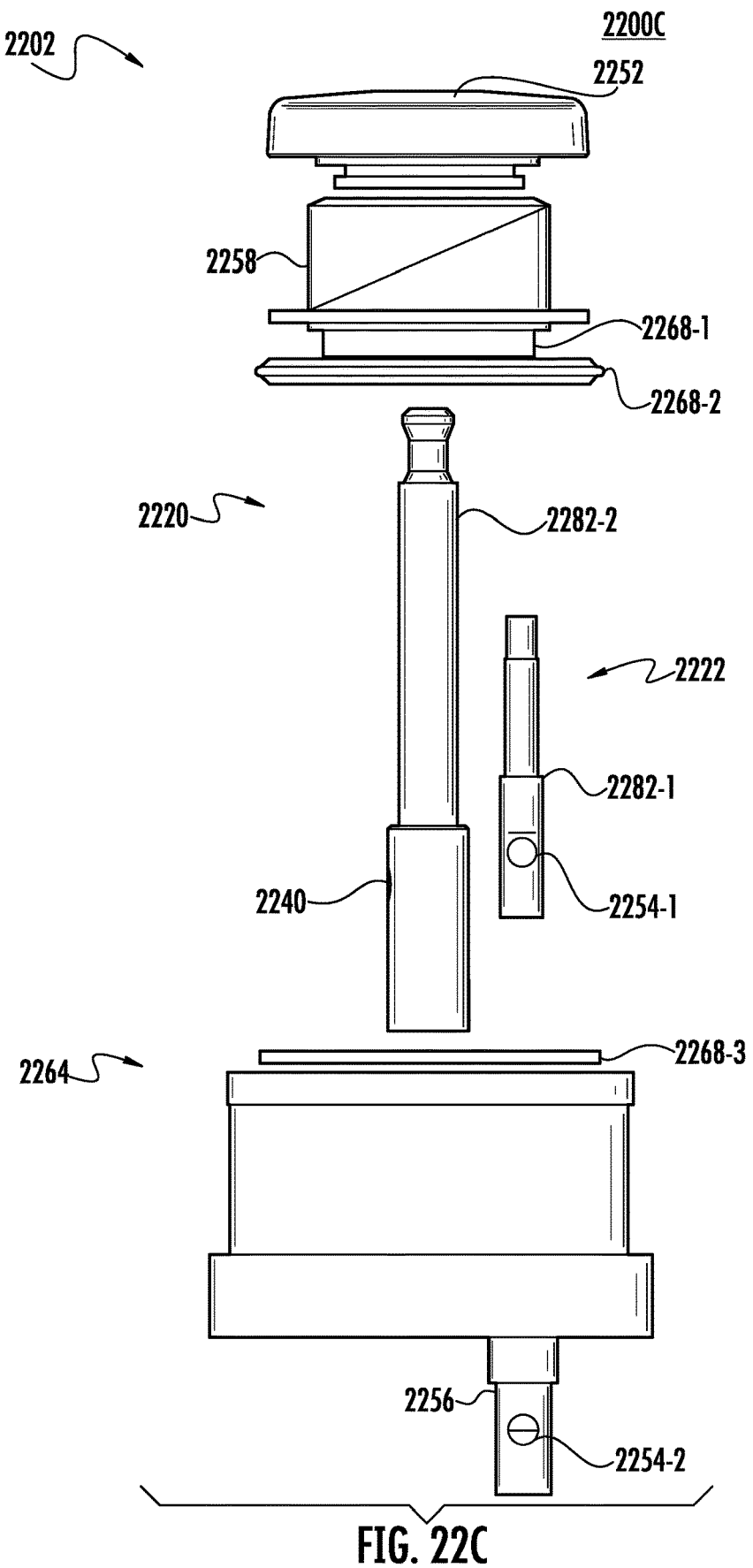

Referring to FIG. 22C, environment 2200C illustrates an exploded view of various components of suction valve assembly 2202. The illustrated embodiment may include interface member 2252, hat 2258, seal 2268-1, seal 2268-2, working channel valve 2220 with working channel valve radial hole 2240 and retention feature 2282-2, balloon valve 2222 with retention feature 2282-1 and one or more balloon valve radial holes 2254-1, seal 2268-3, and bowl 2264 with linkage 2256 and one or more linkage radial holes 2254-2. In the illustrated embodiment, the balloon valve 2222 may include two axially aligned balloon valve radial holes 2254-1 and the linkage 2256 may include two axially aligned linkage radial holes 2254. In various embodiments, suction of a balloon channel of a suction valve well, into which the suction valve assembly 2202 is installed, may be achieved by aligning the one or more balloon valve radial holes 2254-1 with the one or more linkage radial holes 2254-2. The assembled relationships between various components is illustrated in FIG. 22H.

Figure 22D:
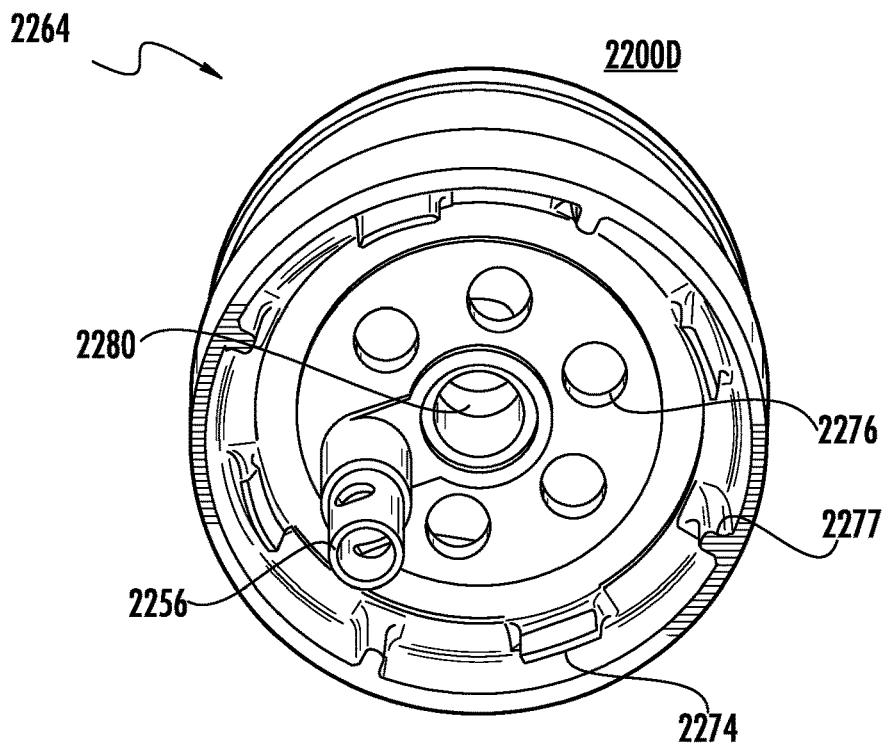
Figure 22E:
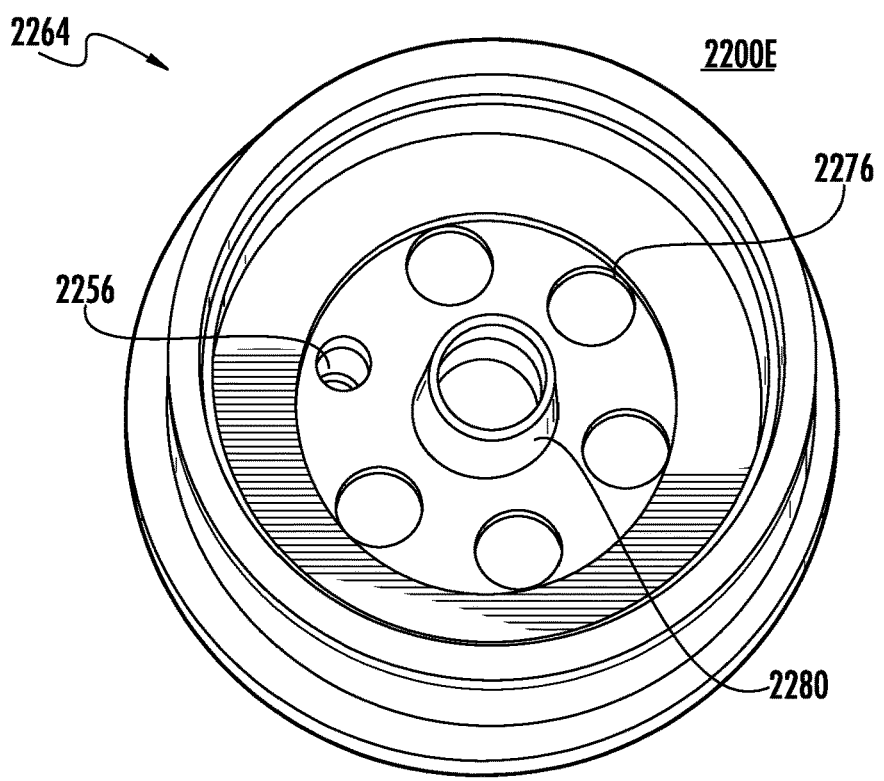

Referring to FIGS. 22D and 22E, environments 2200D, 2200E illustrate various aspects of bowl 2264. Environment 2200D includes a bottom perspective view of bowl 2264 with bowl stem 2280, linkage 2256, one or more vertical holes 2276, one or more alignment member 2277, and one or more retention member 2274. Environment 2200E includes a top perspective view of bowl 2264 with linkage 2256, bowl stem 2280, and one or more vertical holes 2276. In the illustrated embodiment, the one or more vertical holes 2276 includes five circumferentially aligned holes that are parallel to the bowl stem 2280. The linkage 2256 may include a circumferentially aligned hole that is parallel to the bowl stem 2280. In some embodiments, the one or more vertical holes 2276 and the hole of linkage 2256 may be aligned along a common circumference. In various embodiments, one or more portions of the linkage 2256 may comprise a hypo-tube.

In many embodiments, the bowl stem 2280 may taper towards the top of the bowl 2264. In many such embodiments, only the outer or inner surface of the bowl stem 2280 may be tapered. In various embodiments, bowl 2264 may include one or more alignment members 2277 to guide proper alignment of the suction valve assembly 2202 with a suction valve well. In many embodiments, the one or more alignment members 2277 may be received by a corresponding one or more slots in the suction valve well. The one or more retention members 2274 may secure the suction valve assembly 2202 to the suction valve well.

Figure 22F:
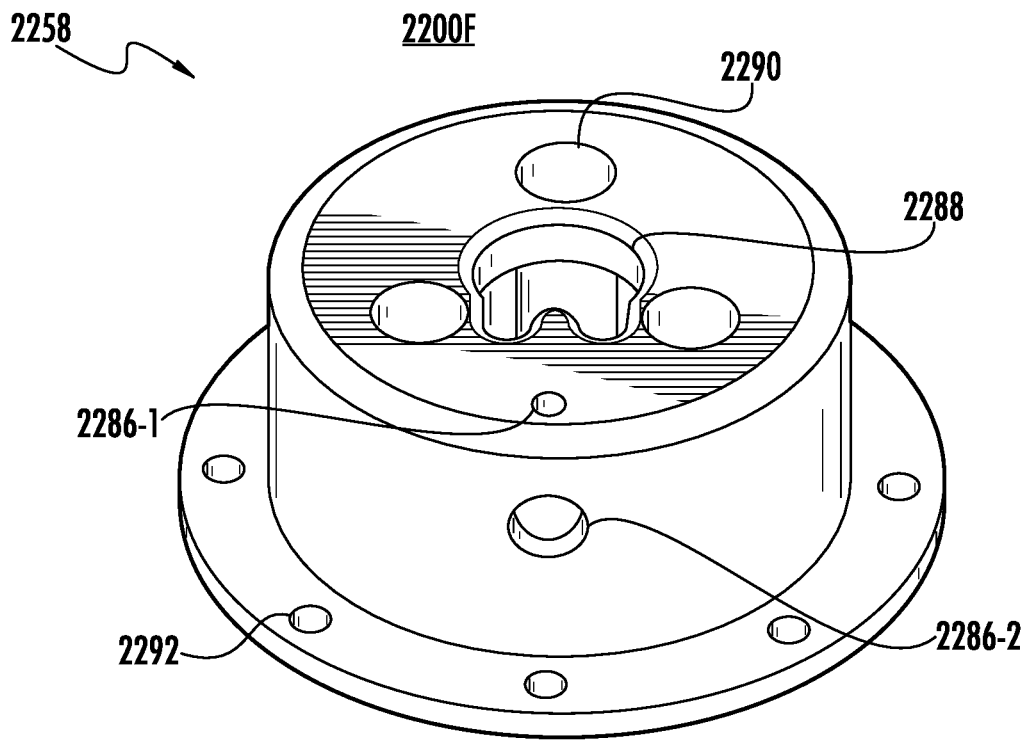
Figure 22G:
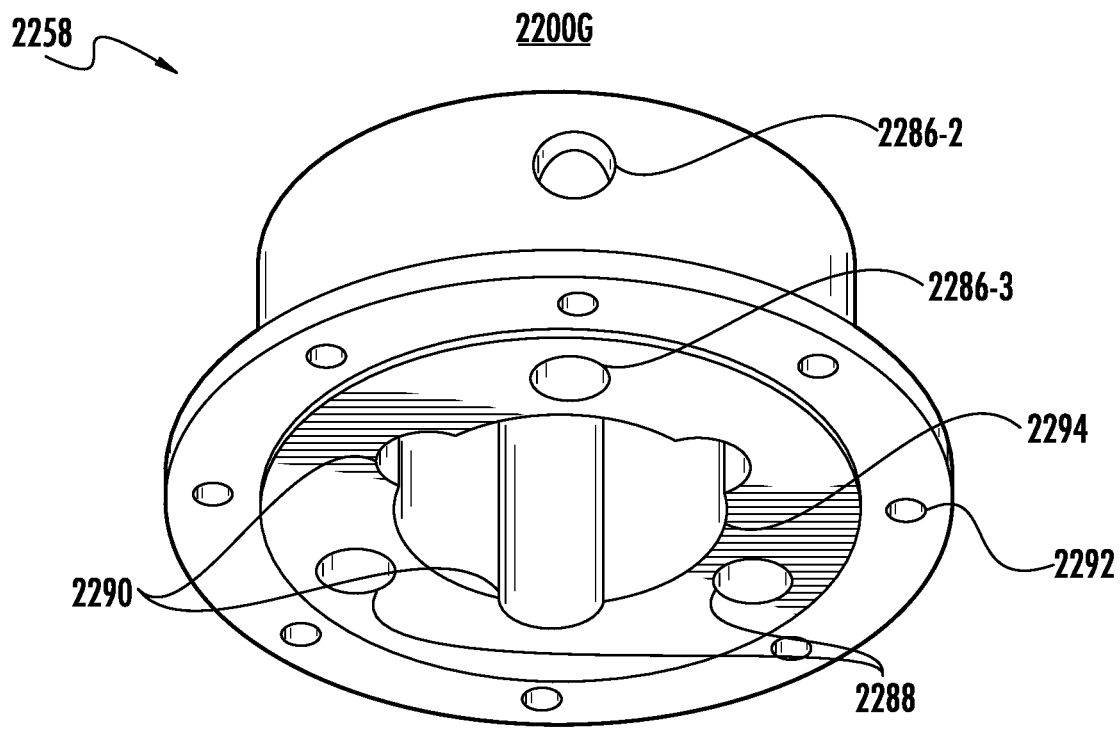
Figure 22H:
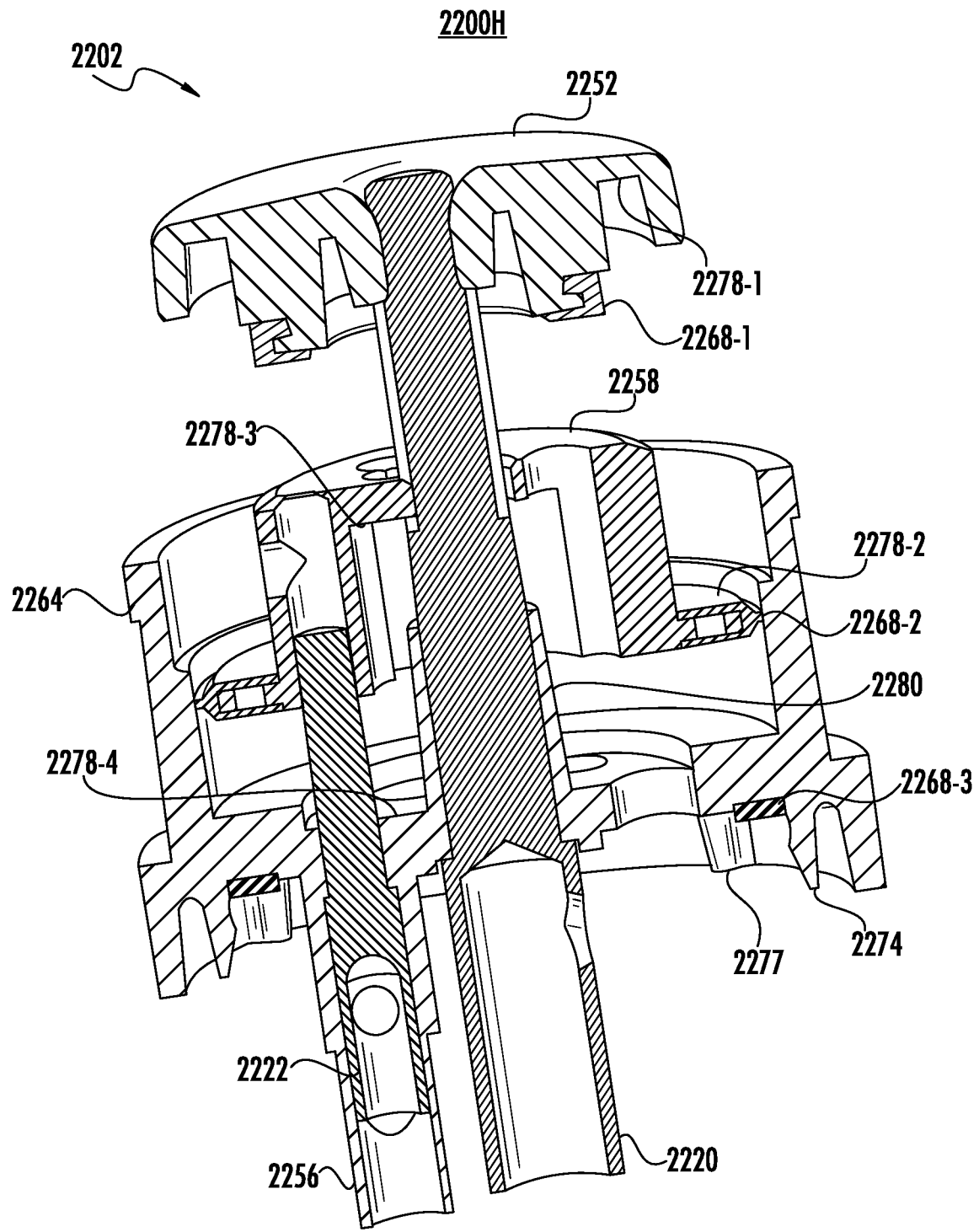

Referring to FIGS. 22F and 22G, environments 2200F, 2200G illustrate various aspects of hat 2258. Environment 2200F includes a top perspective view of hat 2258 with one or more atmospheric vertical passages 2290, working channel valve hole 2288, balloon valve recess top hole 2286-1, balloon valve recess radial hole 2286-2, and one or more flange vertical holes 2292. Environment 2200G includes a bottom perspective view of hat 2258 with balloon valve recess radial hole 2286-2, balloon valve recess bottom hole 2286-3, main channel 2294, one or more flange vertical holes 2292, vertical recesses 2288, and one or more atmospheric vertical passages 2290. In some embodiments, one or more of the holes/recesses may be used to secure pins (see e.g., pins 2168 of FIG. 21B). For example, vertical recesses 2288 may receive the pins and/or balloon valve. In various embodiments, the pins may be glued and/or welded. In many embodiments, one or more of the holes/recesses and pins may include numerous complimentary shapes. For example, one or more hexagonal, oblong, asymmetric shapes may be used. In one embodiment, the shapes may be configured for press fitting one or more components of valve assembly 2202. For instance, a hexagonal shape may be utilized to enable press fitting pins/balloon valves.

In the illustrated embodiment, the one or more flange vertical holes 2292 includes eight circumferentially aligned holes that are parallel to the main channel 2294. In many embodiments, the flange vertical holes 2292 may comprise features to retain a seal (e.g., seal 2168). In many such embodiments, the seal may be overmolded or otherwise assembled into the suction valve assembly 2202. In various embodiments herein, any number of seals may be overmolded. In various such embodiments, features such as recesses, channels, ridges, and the like may be incorporated into components to facilitate overmolding. The main channel 2294 may include a combined lumen for the atmospheric vertical passages 2290 and the working channel valve hole 2288 that enter from the top of hat 2258. In many embodiments, the hat 2258 may be constructed from a rigid material, such as plastic. In various embodiments, the top end of the balloon valve 2222 may be inserted into the balloon valve recess bottom hole 2286-3.

Referring to FIG. 22H, environment 2200H illustrates a cross-sectional view of suction valve assembly 2202. In the illustrated embodiment, the assembled relationships between components of the suction valve assembly 2202 is shown. In many embodiments, a first biasing member may be disposed between biasing member seats 2278-1, 2278-2 and a second biasing member may be disposed between biasing member seats 2278-3, 2278-4. In many embodiments, the interface member 2252, hat 2258, working channel valve 2220 and/or balloon valve 2222 may move up and down with respect to bowl 2264 and a suction valve well to control fluid flow through the suction valve well. In various embodiments, the retention feature 2282-1 of balloon valve 2222 may limit upward motion of the balloon valve 2222.

In many embodiments, the retention feature 2282-2 may prevent rotation of the working channel valve relative to the balloon valve. In several embodiments, the retention feature 2282-2 may interface with a complimentary feature on the hat 2258. In various embodiments, the change in diameter of the working channel valve 2220 may limit upward motion of the working channel valve 2220. In some embodiments, the retention feature 2282-2 of working channel valve 2220 may limit upward motion of the working channel valve 2220.

As previously mentioned, and described, fluid control through the suction valve well may include an atmospheric suction state, a working channel suction state, and a balloon channel suction state (see e.g., FIGS. 3A-3D). In the atmospheric suction state, air may enter the suction valve assembly 2202 via atmospheric vertical passages 2290 of the hat 2258 into the main channel 2294, pass through the vertical holes 2276 of bowl 2264, and exit via a suction channel of a suction valve well. In the working channel suction state, seal 2268-1 may move downward and seal against the atmospheric vertical passages 2290 of hat 2258. Further, the working channel valve 2220 may move downward such that the working channel valve radial hole 2240 aligns with a well radial hole of the suction valve well. Accordingly, fluid may enter the bottom of the working channel valve 2220, pass through the aligned working channel valve radial hole 2240 and well radial hole, and exit via the suction channel of the suction valve well.

In the balloon channel suction state, the hat 2258 may move downward and push the balloon valve 2222 downward such that the balloon valve radial hole 2254-1 aligns with the linkage radial hole 2254-2 of linkage 2256. Seal 2268-1 may continue to seal flow through the atmospheric vertical passages 2290 of hat 2258 by moving downward along with the hat 2258. Further, working channel valve 2220 may move downward such that the working channel valve radial hole 2240 moves below the well radial hole of the suction valve well fluid to prevent flow through the working channel valve radial hole 2240. Accordingly, fluid may enter the bottom of the linkage 2256, pass through the aligned balloon valve radial hole 2254-1 and linkage radial hole 2254-2, and exit via the suction channel of the suction valve well. In some embodiments, the linkage 2256 may include one or more seals (e.g., O-ring) to enable the linkage 2256 to create a seal with the balloon channel of the suction valve well.

FIGS. 23A-23G illustrate various aspects of an exemplary suction valve assembly 2302 in environments 2300A-2300G, according to one or more embodiments described herein. In many embodiments, a cross section of one or more components may be illustrated in environments 2300A-2300G. In some embodiments, one or more components of FIGS. 23A-23G may be the same or similar to one or more other components described herein. For instance, suction valve assembly 2302 may be the same or similar to suction valve assembly 2102 and/or suction valve assembly 2202. Environments 2300A-2300G may include one or more portions of the suction valve assembly 2302. In one or more embodiments described herein, suction valve assembly 2302 may include a set of components to control fluid flow (e.g., suction flow) through a suction valve well when assembled into the valve well. In one or more such embodiments, utilization of the set of components may provide reliable, intuitive, and ergonomic control of fluid through a suction valve well (e.g., suction valve well 2104). Additionally, or alternatively, utilization of suction valve assembly, or one or more components thereof, to control fluid flow through the valve well may simplify manufacturing and/or assembly. Embodiments are not limited in this context.

Figure 23A:
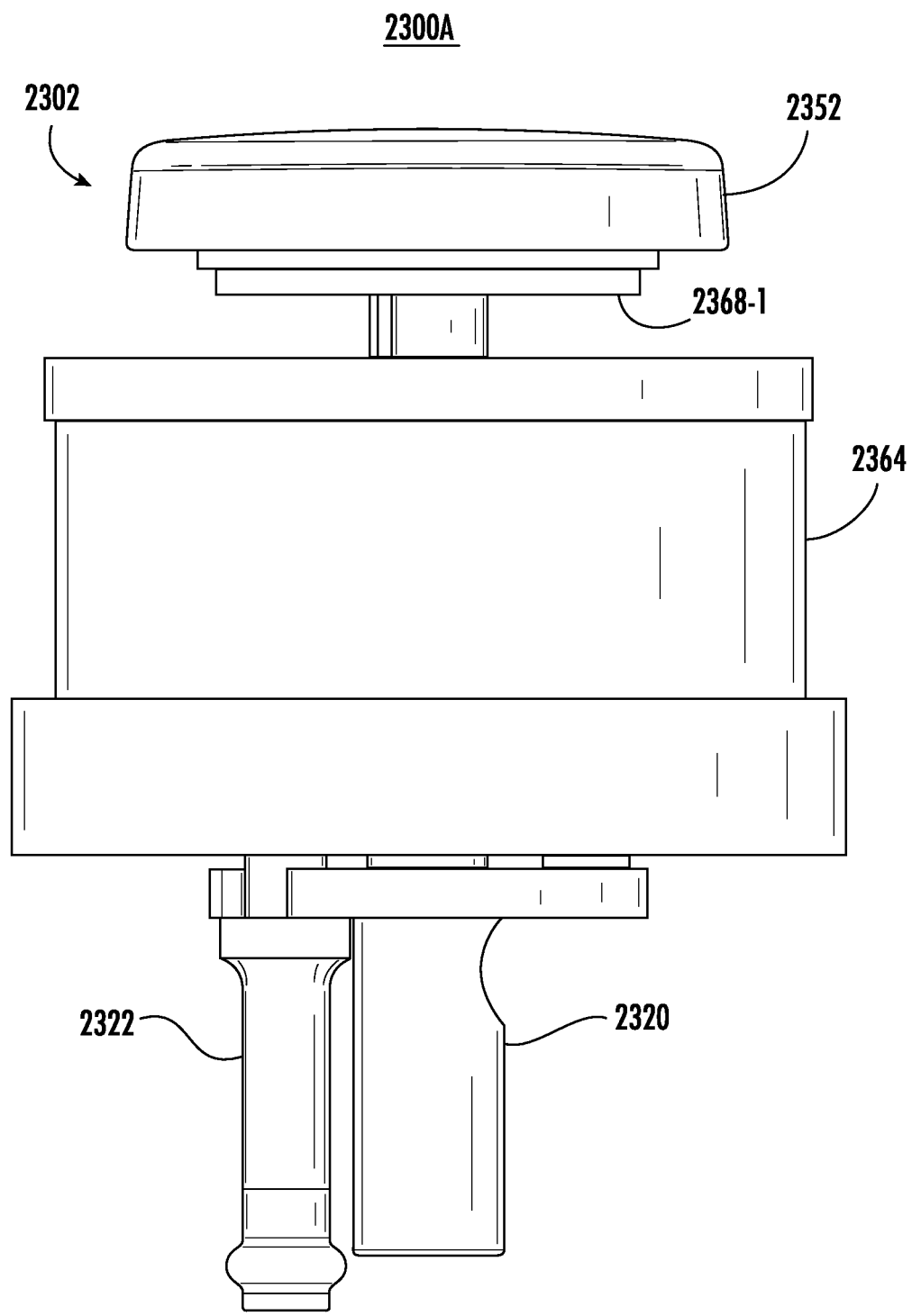
FIGS. 23A-23G illustrate various aspects of an exemplary suction valve assembly, according to one or more embodiments described herein.

Referring to FIG. 23A, environment 2300A illustrates a front view of suction valve assembly 2302. In the illustrated embodiment, suction valve assembly 2302 may include an interface member 2352, seal 2368-1, bowl 2364, working channel valve 2320, and balloon valve 2322. In various embodiments, the suction valve assembly 2302 may be inserted into a suction valve well (e.g., suction valve well 1504). In various such embodiments, the working channel valve 2320 may extend into the working channel of the suction valve well and/or the balloon valve 2322 may extend into the balloon channel of the suction valve well when the suction valve assembly 2302 is inserted into the suction valve well. In many embodiments, the suction valve assembly 2302 may be operated via interface member 2352 to control fluid flow through the suction valve well. Operation of the suction valve assembly 2302 via interface member 2352 may move the working channel valve 2320 up and/or down to control fluid flow through the suction valve well. In many embodiments, the interface member 2352 may be press-fit to the top of the working channel valve 2320. In many embodiments, the suction valve assembly 2302 may include the suction valve well. In some embodiments, bowl 2364 may comprise a housing for one or more components of the suction valve assembly 2302. As will be discussed in more detail below, in many embodiments, the bowl 2364 may include one or more features to align and/or attach the suction valve assembly to a suction valve well.

Figure 23B:
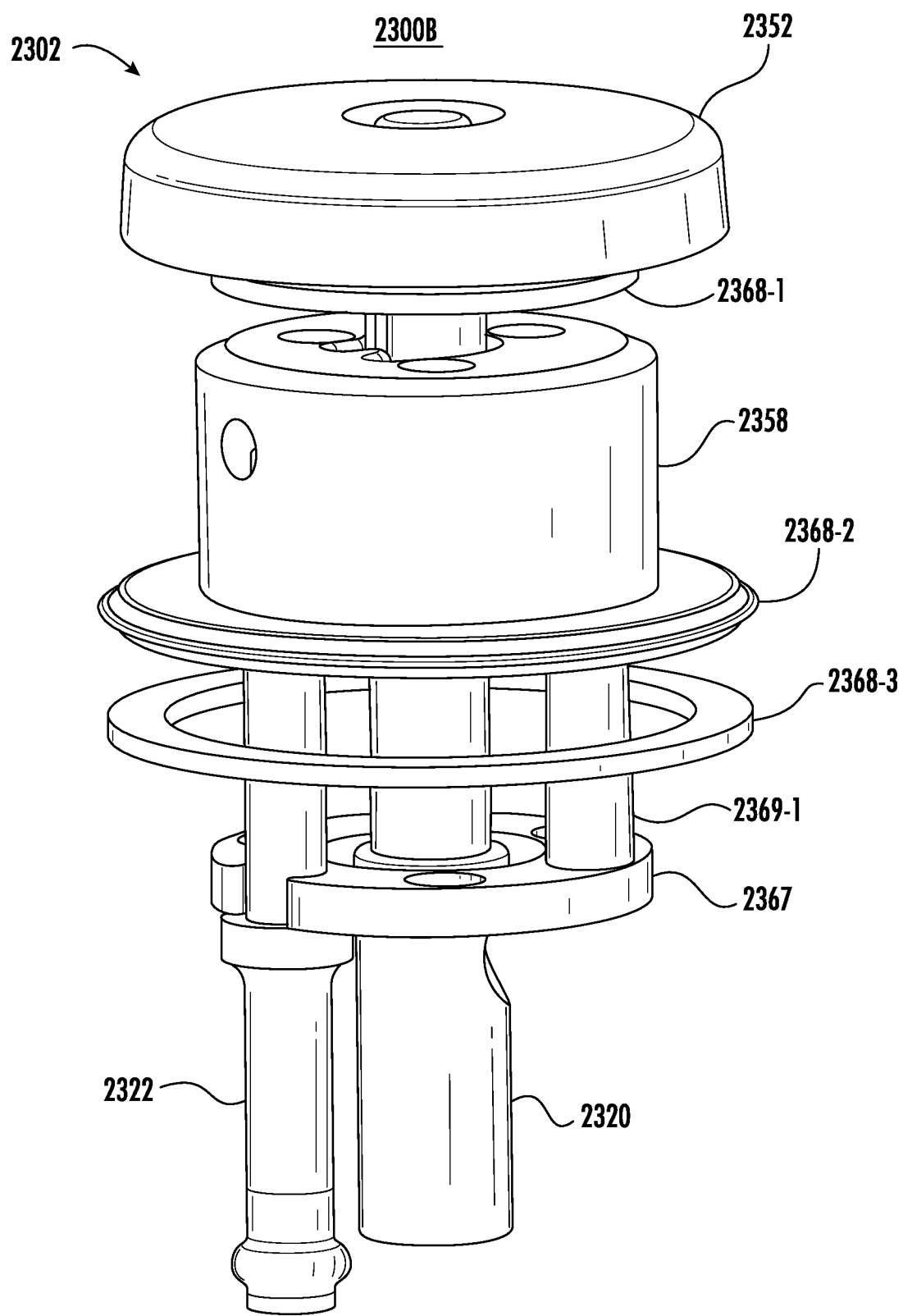

Referring to FIG. 23B, environment 2300B illustrates an assembly stage of the suction valve assembly 2302. The illustrated embodiment may include interface member 2352, seal 2368-1, hat 2358, seal 2368-2, seal 2368-3, working channel valve 2320, pin 2369-1, alignment feature 2367, and balloon valve 2322. One or more of the interface member 2352, hat 2358, seal 2368-1, seal 2368-2, seal 2368-3, and working channel valve 2320 may be axially aligned and the balloon valve 2322 may be parallel to the axis of alignment for the other components. In one or more embodiments, the balloon valve 2322 may be disposed in the linkage 2356. These and other aspects of suction valve assembly 2302 will be described in more detail below.

Figure 23C:
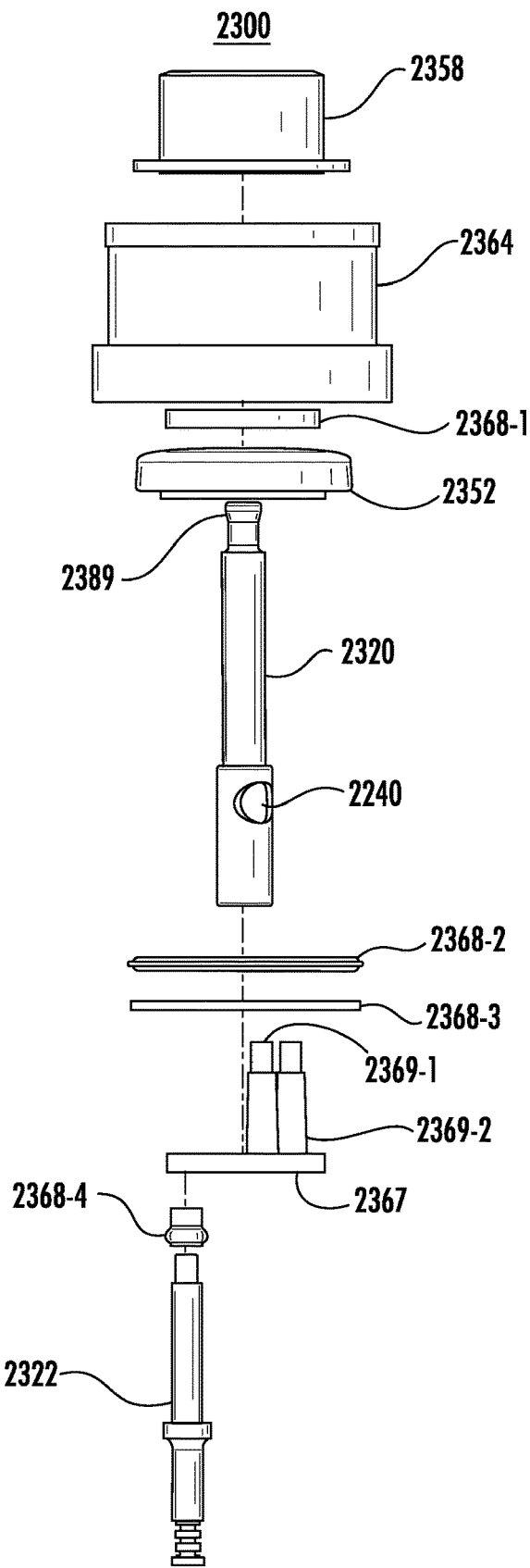

Referring to FIG. 23C, environment 2300C illustrates an exploded view of various components of suction valve assembly 2302. The illustrated embodiment may include hat 2358, bowl 2364, seal 2368-1, interface member 2352, working channel valve 2320 with coupler 2389 and working channel valve radial hole 2240, seals 2368-2, 2368-3, pins 2369-1, 2369-2, alignment feature 2367, and balloon valve 2322 with seal 2368-4. In some embodiments, one or more components of suction valve assembly 2302 may include a spring stanchion that comprises one or more biasing member seats. Various embodiments may include a biopsy port interface. In various such embodiments, the biopsy port interface may be press-fit.

Figure 23D:
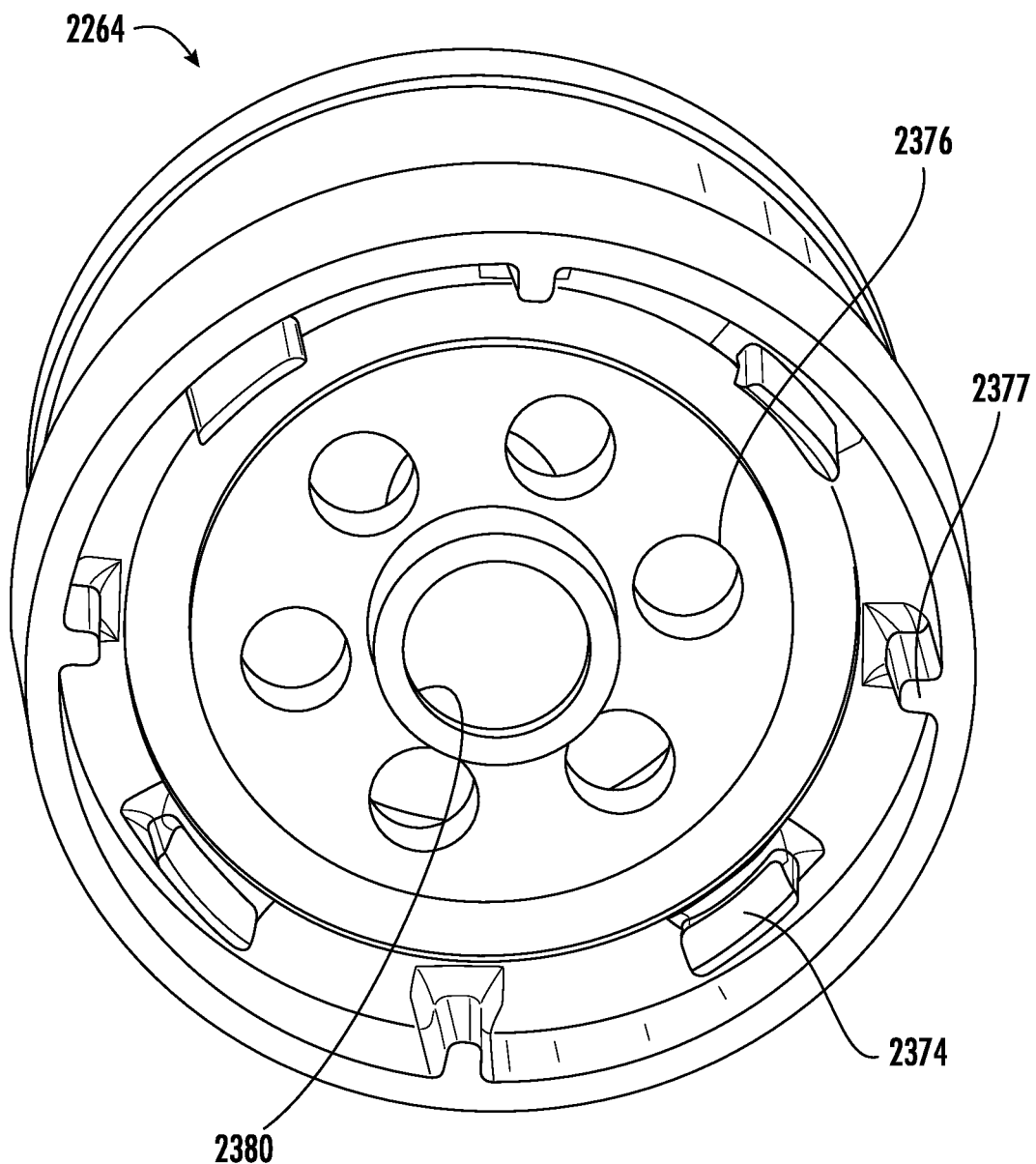
Figure 23E:
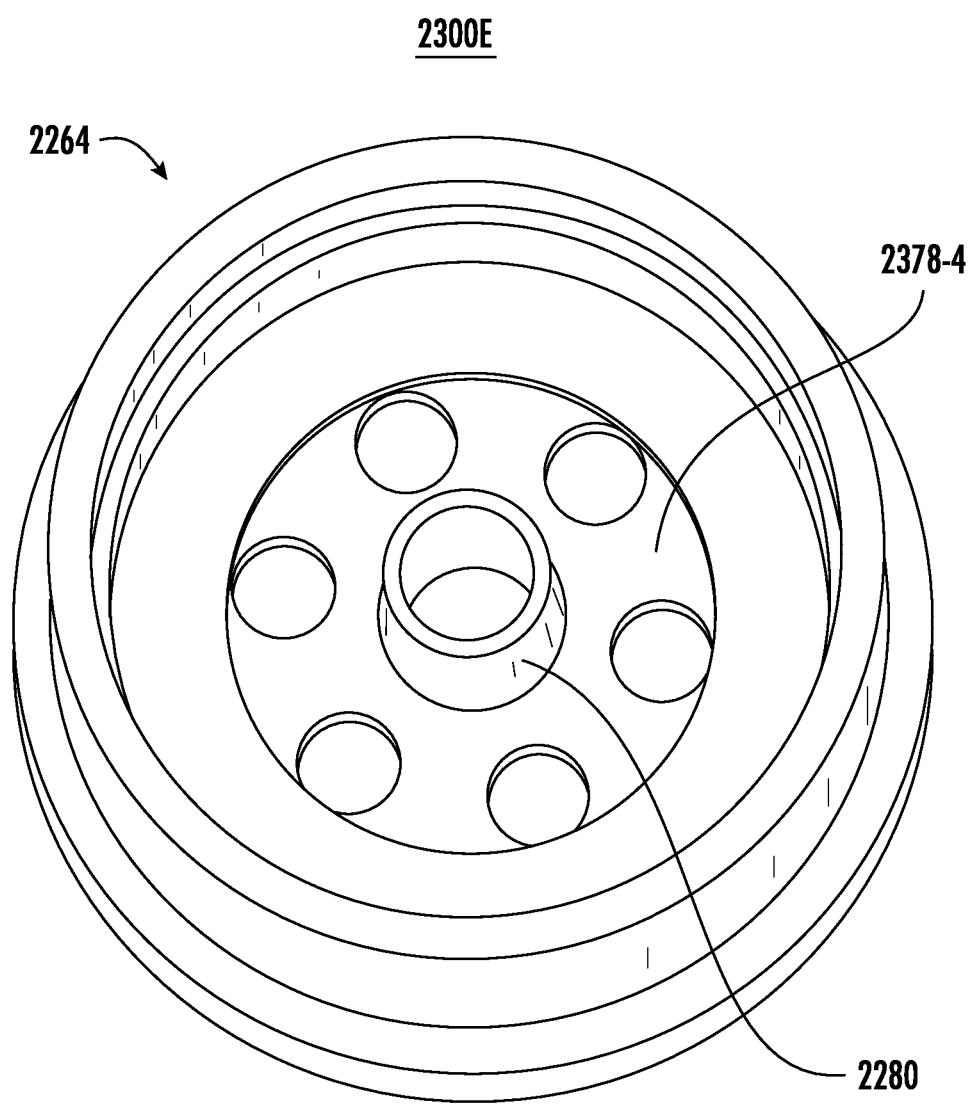

Referring to FIGS. 23D and 23E, environments 2300D, 2300E illustrate various aspects of bowl 2364. Environment 2300D includes a bottom perspective view of bowl 2364 with bowl stem 2380, linkage 2356, one or more vertical holes 2376, one or more alignment member 2377, and one or more retention member 2374. Environment 2300E includes a top perspective view of bowl 2364 with linkage 2356, bowl stem 2380, and one or more vertical holes 2376. In the illustrated embodiment, the one or more vertical holes 2376 includes six circumferentially aligned holes that are parallel to the bowl stem 2380.

In many embodiments, the bowl stem 2380 may taper towards the top of the bowl 2364. In many such embodiments, only the outer or inner surface of the bowl stem 2380 may be tapered. In various embodiments, bowl 2364 may include one or more alignment members 2377 to guide proper alignment of the suction valve assembly 2302 with a suction valve well. In many embodiments, the one or more alignment members 2377 may be received by a corresponding one or more slots in the suction valve well. The one or more retention members 2374 may secure the suction valve assembly 2302 to the suction valve well. The biasing member seat 2378-4 may provide a point of contact for a biasing member.

Figure 23F:
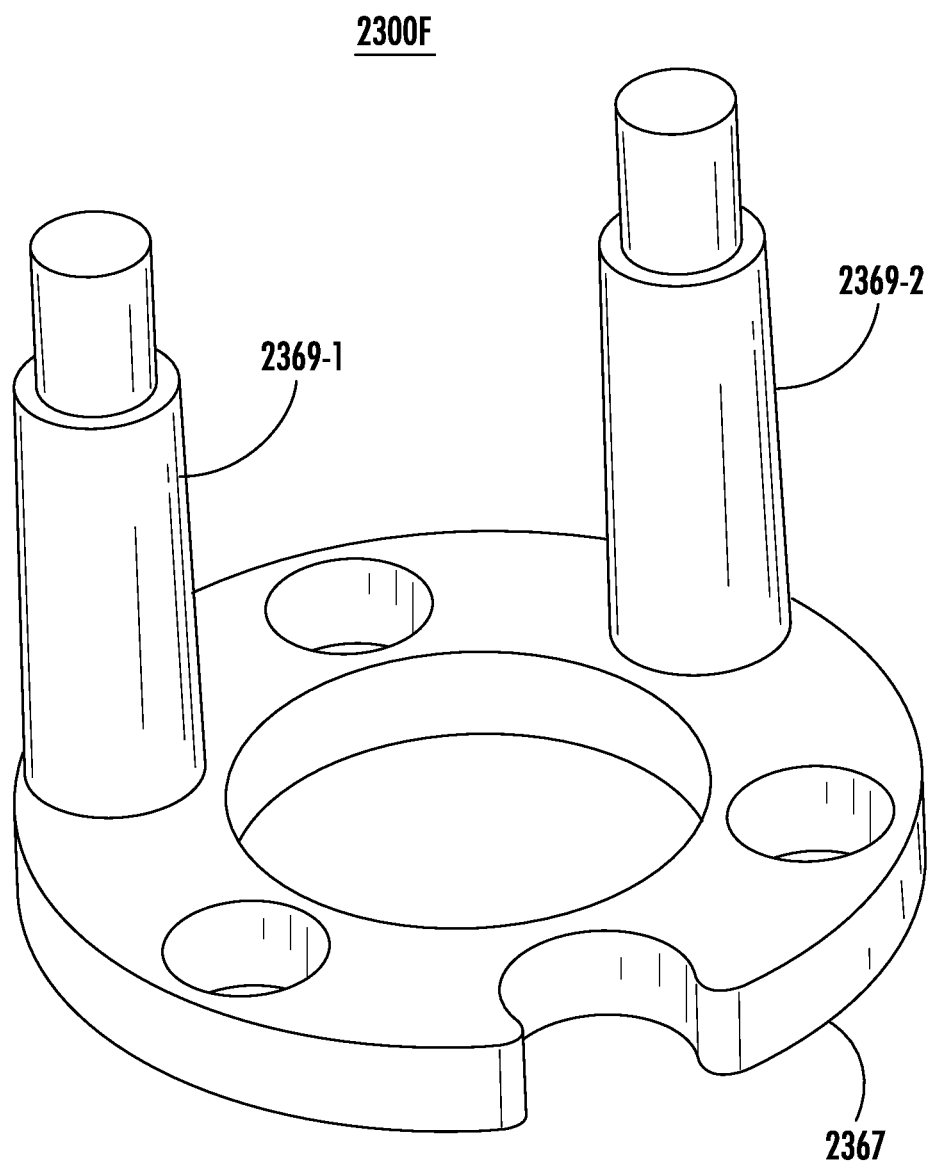

Referring to FIG. 23F, environment 2300F illustrates pins 2369-1, 2369-2 in conjunction with alignment feature 2367. The alignment feature 2367 and pins 2369 may maintain alignment and/or spacing among different components of the suction valve assembly 2302. The tops of pins 2369 may be inserted into corresponding recesses in hat 2358.

Figure 23G:
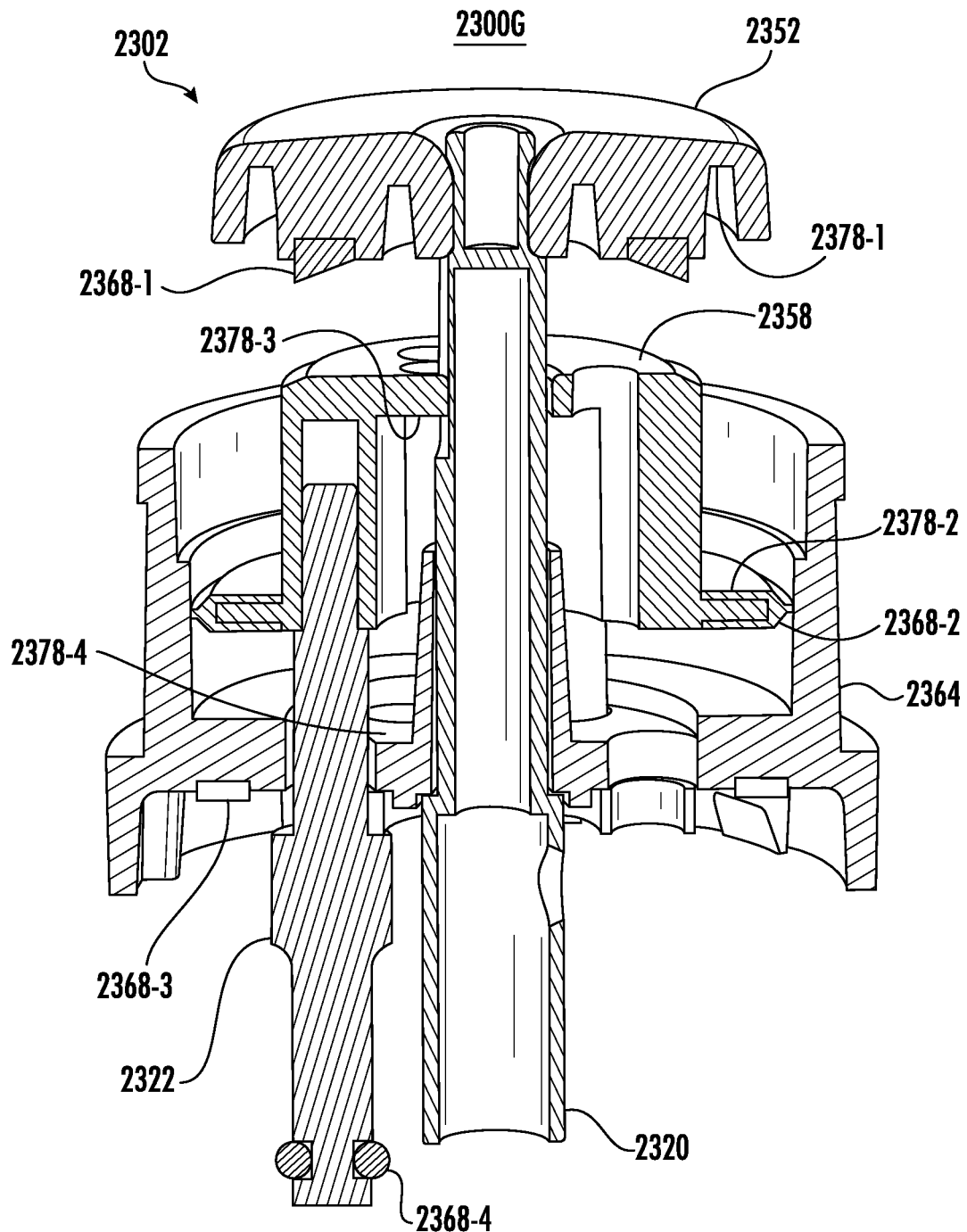

Referring to FIG. 23G, environment 2300G illustrates a cross-sectional view of suction valve assembly 2302. In the illustrated embodiment, the assembled relationships between components of the suction valve assembly 2302 is shown. In many embodiments, a first biasing member may be disposed between biasing member seats 2378-1, 2378-2 and a second biasing member may be disposed between biasing member seats 2378-3, 2378-4. In many embodiments, the interface member 2352, hat 2358, working channel valve 2320 and/or balloon valve 2322 may move up and down with respect to bowl 2364 and a suction valve well to control fluid flow through the suction valve well.

As previously mentioned, and described, fluid control through the suction valve well may include an atmospheric suction state, a working channel suction state, and a balloon channel suction state (see e.g., FIGS. 3A-3D). Suction valve assembly 2302 may operate in the same or similar manner as other suction valve assemblies described herein. The balloon valve 2322 may extend into the balloon channel of a suction valve well when the suction valve assembly 2302 is inserted into the suction valve well (see e.g., FIGS. 6A and 6B). Further, seal 2368-1 may be coupled to interface member 2352 and create a seal with hat 2358, seal 2368-3 may be coupled with bowl 2364 and create a seal with a suction valve well, and seal 2368-4 may be coupled to balloon valve 2322 and create a seal with a balloon channel of the suction valve well.

The medical devices of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
a suction valve set including a working channel valve, a balloon valve, and an atmospheric valve, the working channel valve to control flow through a working channel of a valve well, the balloon valve to control flow through a balloon channel of the valve well, and the atmospheric valve to control flow through an atmospheric channel of the valve well, the suction valve set configurable between a first state, a second state, and a third state, the first state to place the suction channel in fluid communication with the atmospheric channel, the second state to place the suction channel in fluid communication with the working channel, and the third state to place the suction channel in fluid communication with the balloon channel; and
a valve interface mechanism including a set of one or more biasing members, a bowl formed of a single unitary material with a top, a bottom, and a cylindrical portion with an interior, and a linkage extending from the bottom of the bowl, the linkage comprising a top, a bottom, and a tubular structure with an interior, wherein at least a portion of the tubular structure of the linkage is configured for insertion into the balloon channel of the valve well, wherein the balloon valve is configured to extend through at least a portion of the interior of the bowl and at least a portion of the interior of the linkage.

2. The medical device of claim 1, the valve interface mechanism configured to displace at least a portion of the balloon valve toward the bottom of the linkage to place the suction channel in fluid communication with the balloon channel.

3. The medical device of claim 1, the balloon valve comprising a first radial hole and the linkage comprising a second radial hole.

4. The medical device of claim 3, the valve interface mechanism configured to align the first radial hole and the second radial hole to place the suction channel in fluid communication with the balloon channel.

5. The medical device of claim 3, the valve interface mechanism configured to misalign the first radial hole and the second radial hole to block flow through the balloon channel.

6. The medical device of claim 3, the set of one or more biasing members configured to bias the first radial hole out of alignment with the second radial hole.

7. The medical device of claim 1, wherein the tubular structure of the linkage is nonconcentric with the cylindrical portion of the bowl.

8. The medical device of claim 1, wherein the balloon valve is concentric with the linkage and nonconcentric with the bowl when extended through at least a portion of the interior of the bowl and at least a portion of the interior of the linkage.

9. The medical device of claim 1, the set of one or more biasing members configured to bias the balloon valve to block flow through the balloon channel.

10. The medical device of claim 1, the linkage comprising at least a portion of the balloon channel.

11. The medical device of claim 1, the valve interface mechanism configured to displace at least a portion of the balloon valve out of the bottom of the linkage to place the suction channel in fluid communication with the balloon channel.

12. The medical device of claim 1, the valve interface mechanism configured to displace at least a portion of the balloon valve toward the top of the bowl to place the suction channel in fluid communication with the balloon channel.

13. The medical device of claim 1, wherein the bottom of the bowl defines an entirety of each opening of a plurality of openings.

* * * * *